United States Patent
Grillari et al.

(10) Patent No.: US 10,526,657 B2
(45) Date of Patent: Jan. 7, 2020

(54) COMPOSITIONS AND METHODS FOR THE DIAGNOSIS AND TREATMENT OF BONE FRACTURES AND DISORDERS

(71) Applicant: Universität für Bodenkultur Wien, Vienna (AT)

(72) Inventors: Johannes Grillari, Bisamberg (AT); Regina Grillari, Bisamberg (AT); Matthias Hackl, Vienna (AT); Sylvia Weilner, Perzendorf (AT)

(73) Assignee: Universitat fur Bodenkultur Wien, Vienna (AT)

( * ) Notice: Subject to any disclaimer, the term of this patent is extended or adjusted under 35 U.S.C. 154(b) by 0 days.

(21) Appl. No.: 16/060,919

(22) PCT Filed: Dec. 12, 2016

(86) PCT No.: PCT/EP2016/080674
§ 371 (c)(1),
(2) Date: Jun. 8, 2018

(87) PCT Pub. No.: WO2017/098052
PCT Pub. Date: Jun. 15, 2017

(65) Prior Publication Data
US 2018/0363061 A1    Dec. 20, 2018

(30) Foreign Application Priority Data

Dec. 10, 2015 (EP) .................................. 15199413

(51) Int. Cl.
| | | |
|---|---|---|
| A61K 48/00 | (2006.01) | |
| C07H 21/02 | (2006.01) | |
| C07H 21/04 | (2006.01) | |
| C12Q 1/6883 | (2018.01) | |
| A61P 19/10 | (2006.01) | |
| A61K 31/7105 | (2006.01) | |

(52) U.S. Cl.
CPC ........ *C12Q 1/6883* (2013.01); *A61K 31/7105* (2013.01); *A61P 19/10* (2018.01); *C12Q 2600/118* (2013.01); *C12Q 2600/158* (2013.01); *C12Q 2600/178* (2013.01)

(58) Field of Classification Search
CPC .. C12N 2310/11; C12N 15/111; A61K 31/713
See application file for complete search history.

(56) References Cited

U.S. PATENT DOCUMENTS

| | | | |
|---|---|---|---|
| 2007/0037162 A1 | 2/2007 | Venter et al. | |
| 2013/0303591 A1* | 11/2013 | Brown ................. | C12N 15/111 514/44 A |
| 2013/0317007 A1* | 11/2013 | Anderson ............ | C07J 63/008 514/212.05 |

FOREIGN PATENT DOCUMENTS

| | | |
|---|---|---|
| WO | 2007023306 A1 | 3/2007 |
| WO | 2007092433 A1 | 8/2007 |
| WO | 2011014476 A1 | 2/2011 |
| WO | 2013155085 A1 | 10/2013 |

OTHER PUBLICATIONS

Zhao et al., MicroRNAs Regulate Bone Metabolism, Japanese Society for Bone and Mineral Research, 2013, pp. 221-231, vol. 32 (3).
Anastas et al., WNT Signalling Pathways as Therapeutic Targets in Cancer, Nature Reviews Cancer, 2013, pp. 11-26, vol. 13.
Augustine et al., Parathyroid Hormone and Parathyroid Hormone-related Protein Analogs as Therapies for Osteoporosis, Current Osteoporosis Reports, 2013, pp. 1-11, vol. 11 (4).
David P. Bartel, MicroRNA Target Recognition and Regulatory Functions, Cell, 2009, pp. 215-233, vol. 136 (2).
Boeckel et al., Heparin Selectively Affects the Quantification of MicroRNAs in Human Blood Samples, Clinc. Chem., 2013, pp. 1125-1127, vol. 59 (7).
Chen et al., Characterization of MicroRNAs in Serum: a Novel Class of Biomarkers for Diagnosis of Cancer and other Diseases, Cell Research, 2008, pp. 997-1006, vol. 18 (10).
Cheng et al., Plasma Processing Conditions Substantially Influence Circulating microRNA Biomarker Levels, PLoS one, 2013, pp. e64795, vol. 8 (6).
Cosman et al., Romosozumab Treatment in Postmenopausal Women with Osteoporosis, New England Journal of Medicine, 2016, pp. 1532-1543, vol. 375 (16).
Cummings et al., Denosumab for Prevention of Fractures in Postmenopausal Women with Osteoporosis, New England Journal of Medicine, 2009, pp. 756-765, vol. 361 (8).
Deng et al., Repair of Critcal-Sized Bond Defects with Anti-Mir-31-Expressing Bone Marrow Stromal Stem Cells and Poly(Gylcerol Sebacate) Scaffolds, European Cells & Materials, 2014, pp. 13-25, vol. 27.
Ebert et al., MicroRNA Sponges: Competitive Inhibitors of Small RNAs in Mammalian Cells, Nat Methods, 2007, pp. 721-726, vol. 4 (9).
Fang et al., Stimulation of New Bone Formation by Direct Transfer of Osteogenic Plasmid Genes, Proc. Natl. Acad. Sci. USA, 1996, pp. 5753-5758, vol. 93 (12).
Garcia et al., Anticoagulants Interfere with PCR Used to Diagnose Invasive Aspergillosis, J. Clin. Microbiol, 2002, pp. 1567-1568, vol. 40 (4).
M. Jill Gronholz, Prevention, Diagnosis, and Management of Osteoporosis-Related Fracture: A Multifactoral Osteopathic Approach, The Journal of the American Osteopathic Association, 2008, pp. 575-585, vol. 108 (10).

(Continued)

*Primary Examiner* — Amy H Bowman
(74) *Attorney, Agent, or Firm* — Loza & Loza, LLP; Michael Fedrick

(57) ABSTRACT

The present invention relates to the therapy, prophylaxis and diagnosis of disorders that are associated with aberrant bone mineral density, in particular osteoporosis; wherein the level of selected microRNAs in samples of patients are detected and wherein an increase or decrease of said level compared to the level of healthy individuals is indicative of the disorder.

Figure 1:
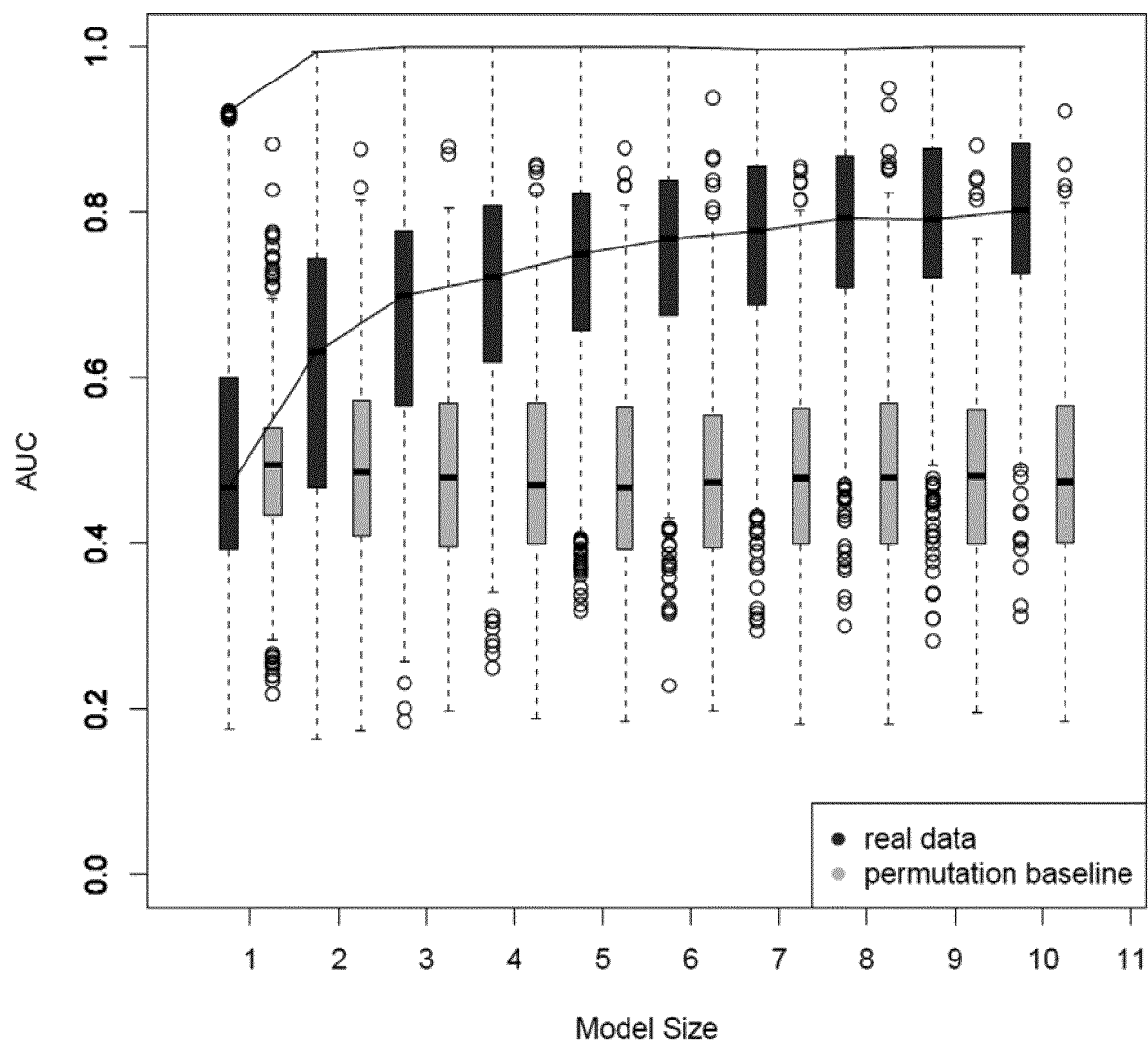

9 Claims, 10 Drawing Sheets
Specification includes a Sequence Listing.

(56) References Cited

OTHER PUBLICATIONS

Kanis et al., European Guidance for the Diagnosis and Management of Osteoporosis in Postmenopausal Women, Osteoporosis Internatational, 2013, pp. 23-57, vol. 24 (1).
Kapinas et al., miR-29 Suppression of Osteonectin in Osteoblasts: Regulation During Differentiation and by Canonical Wnt Signaling, Journal of Cellular Biochemistry, 2009, pp. 216-224, vol. 108 (1).
Kim et al., Plasma Components Affect Accuracy of Circulating Cancer-Related MicroRNA Quantitation, J. Mol. Diagn., 2012, pp. 71-80, vol. 14 (1).
Krutzfeldt et al., Silencing of microRNAs in Vivo with 'Antagomirs', Nature, 2005, pp. 685-689, vol. 438(7068).
Li et al., A microRNA Signature for a BMP2-Induced Osteoblast Lineage Commitment Program, Proc. Nat. Acad. of Sciences of USA, 2008, pp. 13906-13911, vol. 105 (37).
PCT International Application No. PCT/EP2016/080674, Int'l Written Opinion dated Apr. 17, 2017.
Obad et al., Silencing of microRNA Families by Seed-Targeting Tiny LNAs, Nat Genet, 2011, pp. 371-378, vol. 43 (4).
Panach et al., Serum Circulating MicroRNAs as Biomarkers of Osteoporotic Fracture, Calcified Tissue Intern, 2015, pp. 495-505, vol. 97 (5).
Pelled et al., Direct Gene Therapy for Bone Regeneration: Gene Delivery, Animal Models, and Outcome Measures, Tissue Eng. Part B Rev., 2010, pp. 13-20, vol. 16 (1).
Rubin et al., Comparison of Different Screening Tools (FRAX®, OST, ORAI, OSIRIS, SCORE and Age Alone) to Identify Women with Increased Risk of Fracture. A Population-Based Prospective Study, Bone, 2013, pp. 16-22, vol. 56 (1).
Schmittgen et al., Real-time PCR Quantification of Precursor and Mature microRNA, Methods, 2008, pp. 31-38, vol. 44 (1).
Seeliger et al., Five Freely Circulating miRNAs and Bone Tissue miRNAs Are Associated With Osteoporotic Fractures, Journal of Bone and Mineral Res, 2014, pp. 1718-1728, vol. 29 (8), American Society for Bone and Mineral Research.
Trompeter et al., MicroRNAsmiR-26a,miR-26b, and miR-29b Accelerate Osteogenic Differentiation of Unrestricted Somatic Stem Cells from Human Cord Blood, BMC Genomics, 2013, pp. 1-13, vol. 14 (1).
Van Wijnen et al., MicroRNA Functions in Osteogenesis and Dysfunctions in Osteoporosis, Curr. Osteoporosis Reports, 2013, pp. 72-82, vol. 11 (2).
Weilner et al., Secretion of Microvesicular miRNAs in Cellular and Organismal Aging, Experimental Gerontology, 2013, pp. 626-633, vol. 48 (7).
Wolbank et al., Telomerase Immortalized Human Amnion- and Adipose-Derived Mesenchymal Stem Cells: Maintenance of Differentiation and Immunomodulatory Characteristics, Tissue Eng Part A, 2009, pp. 2009, vol. 15 (7).
American Diabetes Association, Diagnosis and Classification of Diabetes Mellitus, Diabetes Care, 2014, pp. 81-90, vol. 37 (1).
Bonci et al., The miR-15a—miR-16-1 Cluster Controls Prostate Cancer by Targeting Multiple Oncogenic Activities, Nature Medicine, 2008, pp. 1271-1277, vol. 14 (11).
Ernesto Canalis, Wnt Signalling in Osteoporosis: Mechanisms and Novel Therapeutic Approaches, Nature Reviews, 2013, pp. 1-9.
Charles A. Cefalu, Is Bone Mineral Density Predictive of Fracture Risk Reduction?, Current Medical Research and Opinion, 2004, pp. 341-349, vol. 20 (3).
Chatterjee et al., Active Turnover Modulates Mature microRNA Activity in Caenorhabditis Elegans, Nature, 2009, pp. 546-551, vol. 461.
Dong et al., MicroRNAs Regulate Osteogenesis and Chondrogenesis, Biochemical and Biophysical Research Communications, 2012, pp. 587-591, vol. 418.
Egermann et al., Direct Adenoviral Transfer of Bone Morphogenetic Protein-2 cDNA Enhances Fracture Healing in Osteoporotic Sheep, Human Gene Therapy, 2006, pp. 507-517, vol. 17.
Harvey et al., Osteoporosis: Impact on Health and Economics, Nature Reviews, 2010, pp. 99-105, vol. 6.
Jadhav et al., Antagomirzymes: Oligonucleotide Enzymes That Specifically Silence MicroRNA Function, Angew. Chem. Int. Ed., 2009, pp. 2557-2560, vol. 48.
Keller et al., Toward the Blood-borne miRNRNome of Human Diseases, Nature Methods, 2011, pp. 841-845, vol. 8 (10).
Li et al, MicroRNA-188 Regulates Age-related Switch Between Osteoblast and Adipocyte Differentiation, The Journal of Clinical Investigation, 2015, pp. 1509-1522, vol. 125 (4).
Luginbuehl et al., Localized Delivery of Growth Factors for Bone Repair, European Journal of Pharmaceutics and Biopharmaceutics, 2004, pp. 197-208, vol. 58.
P.J. Marie, Cell and Gene Therapy for Bone Repair, Osteoporos International, 2011, pp. 2023-2026, vol. 22.
Mitchell et al., Circulating microRNAs as Stable Blood-based Markers for Cancer Detection, Proceedings of the National Academy of Sciences, 2008, pp. 10513-10518, vol. 105 (30).
Tedeschi et al., Hammerhead Ribozymes in Therapeutic Target Discovery and Validation, Drug Discovery Today, 2009, vol. 14 (15).
Vasikaran et al., Markers of Bone Turnover for the Prediction of Fracture Risk and Monitoring of Osteoporosis Treatment: a Need for International Reference Standards, Osteoporos International, 2011, pp. 391-420, vol. 22.
Wolbank et al., Labelling of Human Adipose-Derived Stem Cells for Non-invasive in Vivo Cell Tracking, Cell Tissue Banking, 2007, pp. 163-177, vol. 8.
Wolbank et al., Impact of Human Amniotic Membrane Preparation on Release of Angiogenic Factors, Journal of Tissue Engineering and Regenerative Medicine, 2009, pp. 651-654, vol. 3.
Wolbank et al., Dose-Dependent Immunomodulatory Effect of Human Stem Cells from Amniotic Membrane: A Comparison with Human Mesenchymal Stem Cells from Adipose Tissue, Tissue Engineering, 2007, pp. 1173-1183, vol. 13 (6).
Wolbank et al., Telomerase Immortalized Human Amnion- and Adipose-Derived Mesenchymal Stem Cells: Maintenance of Differentiation and Immunomodulatory Characteristics, Tissue Engineering, 2009, pp. 1843-1854, vol. 15 (7).
Zampetaki et al., MicroRNAs in Vascular and Metabolic Disease, Circulation Research, 2012, pp. 508-522, vol. 110.

* cited by examiner

A

B

C

D

COMPOSITIONS AND METHODS FOR THE DIAGNOSIS AND TREATMENT OF BONE FRACTURES AND DISORDERS

CROSS-REFERENCE TO RELATED APPLICATIONS

This application is the U.S. national stage of International Patent Application No. PCT/EP2016/080674, filed on Dec. 12, 2016 and entitled COMPOSITIONS AND METHODS FOR THE DIAGNOSIS AND TREATMENT OF BONE FRACTURES AND DISORDERS, which claims the benefit of priority under 35 U.S.C. § 119 from European Patent Application No. 15199413.4, filed Dec. 10, 2015. The disclosures of the foregoing applications are incorporated herein by reference in their entirety.

SEQUENCE LISTING

The entire content of a Sequence Listing titled "Sequence_Listing.txt," created on Jun. 4, 2018 and having a size of 22 kilobytes, which has been submitted in electronic form in connection with the present application, is hereby incorporated by reference herein in its entirety.

FIELD OF THE INVENTION

The present invention relates to the therapy, prophylaxis and diagnosis of disorders that are associated with aberrant bone mineral density, in particular osteoporosis.

BACKGROUND OF THE INVENTION

Osteoporosis is characterized by a systemic reduction in bone mass leading to increased bone fragility and an increased risk of bone fracture. Osteoporosis is an asymptomatic disease, which means that patients do not exhibit clear symptoms at the onset or during progression. Consequently, the diagnosis of osteoporosis frequently is made after a patient has sustained a fragility (osteoporotic) fracture. Osteoporotic fractures occur most frequently at the femoral neck, hip, spine or forearm. Osteoporotic fractures are critical outcomes, because they create significant socioeconomic burden (Harvey et al., 2010). The risk of osteoporotic fractures can, however, be reduced by therapeutic treatment. Today, two forms of treatment have been shown to reduce fracture-risk by up to 75% during 1-3 years of treatment: i) anti-resorptive treatments using bisphosphonates or monoclonal antibodies against RANKL impair bone resorption and therefore stabilize bone mass and reduce the risk of fractures (Gronholz et al., 2008, Cummings et al., 2009). ii) anabolic treatments using tropic hormones such as parathyroid hormone or monoclonal antibodies against Sclerostin have been shown to increase bone mass and reduce the risk of fractures (Augustine et al., 2013, Cosman et al., 2016).

These methods of treatments are frequently used to counteract fracture risk in various forms of osteoporosis including type-I postmenopausal osteoporosis, type-II osteoporosis, idiopathic or male osteoporosis. In addition, primary bone cancer or bone metastases will impact bone metabolism and result in bone lesions. Examples are osteosarcoma, and multiple myeloma.

Accurate tools for early diagnosis and fracture-risk assessment are critical to target the right method of treatment to the patient in need of treatment.

Current methods for the assessment of fracture risk as well as treatment response include non-invasive imaging techniques as well as the analysis of clinical parameters and biochemical markers of bone turnover. Recently, microRNAs have been identified to be secreted into the bloodstream from cells of various tissues, possibly indicating pathological processes in different parts of the body. There is evidence that microRNAs play an important role in the development and function of bone forming and bone resorbing cells, specifically osteoblasts and osteoclasts. Both cell types control the homeostasis between bone anabolism and catabolism, and therefore microRNAs play a pivotal physiological role in bone metabolism. To this day, however, little is known whether an imbalance in bone metabolism, which causes bone diseases, may be reflected in the levels of circulating microRNAs.

Osteoporotic fractures are caused by an increase in bone fragility, which can occur due to low bone mass and microarchitectural changes in bone tissue. Such fractures are the critical hard outcome of osteoporosis, which affects more than 75 million people in the United States, Europe and Japan (Kanis et al., 2013). With a lifetime risk of 30%-40% to be affected by vertebral or non-vertebral fractures in developed countries, osteoporosis has an incidence rate similar to that of coronary heart disease. Furthermore, with the exception of forearm fractures, osteoporotic fractures are associated with increased mortality. Most fractures cause acute pain and lead to patient hospitalization, immobilization and often slow recovery.

In addition, osteoporotic symptoms are frequently observed in patients with type 2 diabetes, who overall suffer from an elevated risk of fragility fractures. Diabetes mellitus refers to a group of metabolic diseases in which a subject has high blood sugar. Type 2 diabetes results from insulin resistance, a condition in which cells fail to use insulin properly, sometimes also with an absolute insulin deficiency. This form was previously referred to as non insulin-dependent diabetes mellitus (NIDDM) or "adult-onset diabetes".

In the prophylaxis, diagnosis and management of osteoporosis, the assessment of fracture risk and monitoring of treatment response are two of the most important aspects. Therefore, analysis of bone mass by measuring bone mineral density (BMD) is currently the only clinical parameter of the skeleton that is routinely analyzed in clinical practice and part of the WHO FRAX questionnaire (Kanis et al., 2013). However, due to the lacking correlation with bone strength and bone metabolism (Cefalu, 2004), age- and site-dependent differences in bone density, the assessment of the T-Score (i.e. a comparison of a patient's BMD to that of a healthy thirty-year-old) in combination with other established clinical scores of fracture risk (Rubin et al., 2013) often does not improve the prediction of fracture risk. Particularly in case of patients suffering from type-2 diabetes there is no evidence for correlation between BMD and fracture risk, which demonstrates the need for alternative markers of fracture risk.

In order to estimate the rate of bone formation, bone resorption and therapeutic treatment response, few biochemical bone turnover markers (BTM) have been identified (Vasikaran et al., 2011), such as serum procollagen type I N propeptide (s-PINP), serum C-terminal telopeptide of type I collagen (s-CTX). While the correlation of these markers with bone metabolism has been established, their specificity and sensitivity for fracture risk prediction needs to be further validated. Therefore, only few countries have recommended to incorporate these biochemical markers into clinical practice (Vasikaran et al., 2011).

Other potential markers of bone metabolism may be derived from the signaling pathways that are known to play a major role in bone formation and resorption, such as WNT, BMP-2 or RANKL. For example, proteins derived from Dickkopf-1 (DKK-1) or Sclerostin (SOST) genes can act as binding partners of WNT and WNT-receptors, thereby regulating its activity and subsequently bone formation (Canalis, 2013). However, the pre-analytical stability of these proteins in serum/plasma in response to diet, exercise and circadian rhythm is questionable, and so is the general significance for bone metabolism due to the fact that these proteins are produced in other tissues as well and might be regulated in response to other diseases. Especially in respect to certain types of cancer, WNT-signalling has been shown to drive the progression of disease (Anastas & Moon, 2013).

Recently, increased attention has been attributed to the importance of microRNAs (miRNAs), small non-coding RNAs that regulate gene expression (Bartel, 2009), in the control of bone metabolism (Dong, Yang, Guo, & Kang, 2012; Zhao et al., 2013). Several miRNAs have been shown to silence osteogenic inhibitors during stem cell differentiation into osteocytes (Trompeter et al., 2013), to regulate BMP2-mediated osteoblast proliferation and differentiation (Li et al., 2008), or to orchestrate the activity of WNT-signalling (Kapinas, Kessler, & Delany, 2009). Therefore, the potential of miRNAs as therapeutic agents for accelerating bone regeneration and/or as diagnostic tools for evaluating bone metabolism and fracture risk has recently been acknowledged (van Wijnen et al., 2013). The impressive stability of miRNA in serum and plasma even after being subjected to harsh conditions, the limited number of miRNAs (<500 found secreted in plasma/serum), their simple chemical composition, the lack of posttranscriptional modification and the availability of advanced and well established, highly sensitive screening techniques define miRNAs as excellent candidates for biomarkers. In fact, blood-circulating miRNAs have already been analyzed in the context of disease (Keller et al., 2011), especially cancer and cardiovascular disease, or non-pathological processes such as ageing (Weiner et al., 2013). A combination of miRNAs that can control the onset and progression of osteoporosis or can serve as surrogate markers for this pathological process, is a specific osteoporosis signature whose use would represent a non-invasive approach to predict the fracture risk as well as targets for therapeutic control of the progression of osteoporosis.

Recently, five freely circulating miRNAs and bone tissue miRNAs have been identified and implicated with osteoporotic fractures (Seeliger et al., 2014).

Recently, miR-188-5p was found to be up-regulated in the bone of aged mice, to induce adipogenic differentiation, and to inhibit osteogenic differentiation (Li et al., 2015).

SUMMARY OF THE INVENTION

It is the objective of the present invention, to broaden the scope, specificity and validity in diagnosing osteoporosis or osteopenia and predicting fractures, and to provide novel agents for the therapy of osteoporosis by stabilizing bone homeostasis and accelerating fracture healing.

The problem is solved by the present invention.

The inventors have detected specific miRNAs that are up- or down-regulated in blood samples derived from patients with recent as well as non-recent osteoporotic fractures.

The present invention specifically provides a selected set of miRNAs that are specifically up- or down-regulated and are thus useful as valuable biomarkers and represent a diagnostic signature applicable both over a broad range of bone disease stages and age groups.

According to the invention there is provided an in vitro method of diagnosing osteoporosis, determining the risk of osteoporotic fractures or monitoring of treatment success in a subject, which can be, but is not limited to a post-menopausal female or an osteoporosis or osteopenia patient, suffering from or being at risk of developing bone fractures, comprising the steps of:

a) providing a sample, specifically a blood sample, from said subject, b) measuring the level of two or more miRNAs, specifically 3, 4, 5, 6, 7, 8, 9, 10, 11, 12, 13, 14, 15, 16, 17, 18, 19, 20, 21, 22, 23, 24, 25, 26, 27, 28, 29 or 30 mRNAs, selected from any of miRNAs consisting of hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-31-5p, hsa-miR-335-5p, hsa-let-7b-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d or isoforms or variants thereof, and c) comparing the level of said miRNAs to a reference level, wherein the magnitude of difference in said level when compared to the reference level is indicative of osteoporosis or the risk of fractures.

According to an alternative embodiment, there is provided an in vitro method of diagnosing osteoporosis or determining the risk of osteoporotic fractures or monitoring of treatment in a subject, comprising the steps of:

a) providing a sample from said subject, b) measuring the level of one, 2, 3, 4, 5, 6, or 7 miRNAs selected from any of miRNAs consisting of hsa-miR-144-3p, hsa-miR-214-3p, hsa-miR-29b-3p, hsa-miR-335-5p, hsa-miR-31-5p, hsa-let-7b-5p and hsa-miR-181d or isoforms or variants thereof, and c) measuring the level of one, 2, 3, 4, 5, 6, 7, 8, 9, 10, 11, 12, 13, 14, 15, 16, 17, 18, 19, 20, 21, 22, or 23 miRNAs selected from any of miRNAs consisting of hsa-miR-188-3p, hsa-miR-382-3p, hsa-miR-127-3p, hsa-miR-155-5p, hsa-miR-181a-3p, hsa-miR-1908, hsa-miR-190a, hsa-miR-199b-5p hsa-miR-203a, hsa-miR-330-3p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p and hsa-miR-942, or isoforms or variants thereof, and d) comparing the level of said miRNAs to a reference level, wherein the magnitude of difference in said level when compared to the reference level is indicative of osteoporosis or the risk of fractures.

According to a specific embodiment, the level of 3, 4, 5, 6, 7, 8 miRNAs selected from the group consisting of hsa-miR-203a, hsa-miR-330-3p, hsa-miR-188-3p, hsa-miR-550a-5p, hsa-miR-335-5p, hsa-miR-29b-3p, hsa-miR-214-3p and hsa-miR-31-5p is measured.

According to a specific embodiment, the level of all of hsa-miR-203a, hsa-miR-330-3p, hsa-miR-188-3p, hsa-miR-550a-5p, hsa-miR-335-5p, hsa-miR-29b-3p, hsa-miR-214-3p and hsa-miR-31-5p is measured.

According to a specific embodiment of the invention there is provided a method wherein at least one, 2, 3, 4, 5, 6, 7, 8 miRNA selected from the group consisting of hsa-miR-188-3p, hsa-miR-382-3p, hsa-miR-203a, hsa-miR-181a-3p, hsa-miR-29b-3p, hsa-miR-330-3p, hsa-miR-335-5p and hsa-miR-369-3p and at least one, 2, 3, 4, 5, 6, 7, 8, 9, 10, 11, 12, 13, 14, 15, 16, 17, 18, 19, 20, 21, 22, 23, 24 miRNAs selected from the group consisting of hsa-miR-127-3p, hsa-miR-155-5p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, and hsa-miR-181d are measured.

According to a specific embodiment of the invention there is provided a method wherein 1 or 2 miRNAs selected from the group consisting of hsa-miR-29b-3p, hsa-miR-335-5p and at least one, 2, 3, 4, 5, 6, 7, 8, 9, 10, 11, 12, 13, 14, 15, 16, 17, 18, 19, 20, 21, 22, 23, 24, 25, 26, 27, 28, 29 or 30 miRNAs selected from the group consisting of hsa-miR-188-3p, hsa-miR-382-3p, hsa-miR-203a, hsa-miR-127-3p, hsa-miR-155-5p, hsa-miR-181a-3p, hsa-miR-1908, hsa-miR-190a, hsa-miR-199b-5p, hsa-miR-144-3p, hsa-miR-330-3p, hsa-miR-335-5p, hsa-miR-31-5p, hsa-miR-214-3p, hsa-miR-29b-4p, hsa-let-7b-5p, hsa-miR-342-5p, hsa-miR-369-3p hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, and hsa-miR-181d are measured.

According to a further embodiment, a method for determining whether a therapeutic amount of a pharmaceutical reduces the risk of developing bone fractures is also provided, comprising
 a) providing a sample, specifically a blood sample, from said subject,
 b) measuring the level of two or more miRNAs, specifically of 3, 4, 5, 6, 7, 8, 9, 10, 11, 12, 13, 14, 15, 16, 17, 18, 19, 20, 21, 22, 23, 24, 25, 26, 27, 28, 29, 30 miRNAs selected from any of miRNAs consisting of hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-335-5p, hsa-miR-31-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and has-miR-181d or isoforms or variants thereof, or
 measuring the level of two or more miRNAs, specifically of 3, 4, 5, 6, 7, 8, 9, 10, 11, 12, 13, 14, 15, 16, 17, 18, 19, 20, 21, 22, 23, 24, 25, 26 miRNAs selected from any of miRNAs consisting of hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-550a-5p, hsa-miR-7-5p, hsa-miR-92a-3p, hsa-miR-942, hsa-miR-96-5p, hsa-miR-330-3p, hsa-miR-31-5p, hsa-miR-144-3p and hsa-miR-382-3p, and
 c) comparing the level of said miRNAs to a reference level, which optionally may be the miRNA level measured before treatment,
 wherein the magnitude of difference in said level when compared to the reference level is indicative of treatment success.

According to a further embodiment, a method for determining whether a therapeutic amount of a pharmaceutical reduces the risk of developing bone fractures is also provided, comprising
 a) providing a sample, specifically a blood sample, from said subject,
 b) measuring the level of one, 2, 3, 4, 5, 6, or 7 miRNAs selected from any of miRNAs consisting of hsa-miR-144-3p, hsa-miR-214-3p, hsa-miR-29b-3p, hsa-miR-335-5p, hsa-miR-31-5p, hsa-let-7b-5p and hsa-miR-181d or isoforms or variants thereof, and
 c) measuring the level of one, 2, 3, 4, 5, 6, 7, 8, 9, 10, 11, 12, 13, 14, 15, 16, 17, 18, 19, 20, 21, 22, or 23 miRNAs selected from any of miRNAs consisting of hsa-miR-188-3p, hsa-miR-382-3p, hsa-miR-127-3p, hsa-miR-155-5p, hsa-miR-181a-3p, hsa-miR-1908, hsa-miR-190a, hsa-miR-199b-5p hsa-miR-203a, hsa-miR-330-3p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p and hsa-miR-942, or isoforms or variants thereof, and
 d) comparing the level of said miRNAs to a reference level, which optionally may be the miRNA level measured before treatment,
 wherein the magnitude of difference in said level when compared to the reference level is indicative of treatment success. According to a further specific embodiment of the invention, 1, 2, 3, 4, 5, 6 or 7 of hsa-miR-188-3p, hsa-miR-382-3p, hsa-miR-181a-3p, has-miR-29b-3p, hsa-miR-330-3p, has-miR-335-5p and hsa-miR-369-3p are measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26 miRNAs, selected from hsa-miR-127-3p, hsa-miR-155-5p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, hsa-miR-330-3p, and hsa-miR-181d.

According to a specific embodiment, the level of all of or 2, 3, 4, 5, 6 or 7 of hsa-miR-203a, hsa-miR-330-3p, hsa-miR-188-3p, hsa-miR-550a-5p, hsa-miR-335-5p, hsa-miR-29b-3p, hsa-miR-214-3p and hsa-miR-31-5p is measured for determining whether a therapeutic amount of a pharmaceutical reduces the risk of developing bone fractures.

According to a specific embodiment of the invention there is provided a method, wherein hsa-miR-188-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27 miRNAs, selected from the group consisting of hsa-miR-127-3p, hsa-miR-155-5p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, hsa-miR-330-3p, and hsa-miR-181d.

According to a specific embodiment of the invention there is provided a method, wherein hsa-miR-188-3p is measured in combination with at least one miRNA, specifically 2, 3, 4 miRNAs, selected from the group consisting of hsa-miR-335-5p, hsa-miR-31-5p, hsa-miR-29b-4p, and hsa-miR-181d, and optionally with at least one miRNA, specifically 2, 3, 4, 5, 6, 7, 8, 9, 10, 11, 12, 13, 14, 15, 16, 17, 18, 19, 20, 21, 22, 23, 24, 25, 26, 27 miRNAs, selected from the group consisting of hsa-miR-127-3p, hsa-miR-155-5p, hsa-miR-1908, hsa-miR-190a, hsa-miR-199b-5p, hsa-miR-144-3p, hsa-miR-214-3p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, hsa-miR-330-3p.

According to a specific embodiment of the invention there is provided a method, wherein hsa-miR-188-3p is measured in combination with at least one miRNA. specifically 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 miRNAs, selected from the group consisting of hsa-miR-382-3p, hsa-miR-203a, hsa-miR-181a-3p, hsa-miR-29b-3p, hsa-miR-330-3p, hsa-miR-335-5p, hsa-miR-369-3p, hsa-miR-127-3p, hsa-miR-155-5phsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, and hsa-miR-181d.

According to a specific embodiment of the invention there is provided a method, wherein hsa-miR-188-3p is measured in combination with at least one miRNA, specifically 2, 3, 4, 5, 6, 7 miRNAs, selected from the group consisting of hsa-miR-29b-3p, hsa-miR-335-5p, hsa-miR-144-3p, hsa-miR-31-5p, hsa-miR-29b-4p, and hsa-miR-181d. and optionally with at least 1, 2, 3, 4, 5, 6, 7, 89, 10, 11, 12, 13, 14, 15, 16, 17, 18, 19, 20, 21, 22, 23, 24, 25, 26 miRNAs, selected from the group consisting of hsa-miR-382-3p, hsa-miR-203a, hsa-miR-181a-3p, hsa-miR-330-3p, hsa-miR-369-3p, hsa-miR-127-3p, hsa-miR-155-5p, hsa-miR-1908, hsa-miR-190a, hsa-miR-199b-5p, hsa-miR-214-3p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, and hsa-miR-181d.

According to a specific embodiment of the invention there is provided a method, wherein hsa-miR-382-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28 miRNAs, selected from the group consisting of hsa-miR-127-3p, hsa-miR-155-5p, hsa-miR-188-3p, hsa-miR-1908, hsa-miR-190a, hsa-miR-199b-5p, hsa-miR-335-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, hsa-miR-330-3p, hsa-miR-31-5p, hsa-miR-144-3p and hsa-miR-181d.

According to a specific embodiment of the invention there is provided a method, wherein hsa-miR-382-3p is measured in combination with at least one miRNA, specifically 2, 3, 4, 5 miRNAs, selected from the group consisting of hsa-miR-188-3p, hsa-miR-335-5p, hsa-miR-29b-4p, hsa-miR-31-5p, and hsa-miR-181d and optionally in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28 miRNAs, selected from the group consisting of hsa-miR-127-3p, hsa-miR-155-5p, hsa-miR-1908, hsa-miR-190a, hsa-miR-199b-5p, hsa-miR-214-3p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-miR-96-5p, hsa-miR-330-3p, hsa-miR-144-3p and hsa-miR-181d.

According to a specific embodiment of the invention there is provided a method, wherein hsa-miR-382-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-181a-3p, hsa-miR-330-3p, hsa-miR-369-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-29b-3p, hsa-miR-342-5p, hsa-miR-335-5p, hsa-miR-31-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and hsa-miR-181d.

According to a specific embodiment of the invention there is provided a method, wherein hsa-miR-382-3p is measured in combination with at least one miRNA, specifically 2, 3, 4, 5 miRNAs, selected from the group consisting of hsa-miR-181a-3p, hsa-miR-29b-3p, hsa-miR-335-5p, hsa-miR-31-5p, and hsa-miR-181d, optionally in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-144-3p, hsa-miR-188-3p, hsa-miR-330-3p, hsa-miR-369-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p.

According to a specific embodiment of the invention there is provided a method, wherein hsa-miR-181a-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27 miRNAs, selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

According to a specific embodiment of the invention there is provided a method, wherein hsa-miR-181a-3p is measured in combination with at least one miRNA, specifically 2, 3, 4, 5 miRNAs, selected from the group consisting of, hsa-miR-144-3p, hsa-miR-335-5p, hsa-miR-31-5p, hsa-miR-29b-4p and hsa-miR-181d, and optionally in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-miR-188-3p hsa-miR-127-3p, hsa-miR-155-5p, hsa-miR-1908, hsa-miR-190a, hsa-miR-199b-5p, hsa-miR-214-3p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-

5p, hsa-miR-542-5p, hsa-miR-550a-5p, hsa-miR-576-3p, hsa-miR-582-3p, hsa-miR-642a-5p and hsa-miR-942.

According to a specific embodiment of the invention there is provided a method, wherein hsa-miR-181a-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-382-3p, hsa-miR-330-3p, hsa-miR-369-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-29b-3p, hsa-miR-342-5p, hsa-miR-335-5p, hsa-miR-31-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p, and hsa-miR-181d.

According to a specific embodiment of the invention there is provided a method, wherein hsa-miR-181a-3p is measured in combination with at least one miRNA, specifically 2, 3, 4, 5, 6 miRNAs, selected from the group consisting of hsa-miR-144-3p, hsa-miR-199b-5p, hsa-miR-29b-3p, hsa-miR-335-5p, hsa-miR-31-5p, and hsa-miR-181d, and optionally in combination with at least one miRNA, specifically 2, 3, 4, 5, 6, 7, 8, 9, 10, 11, 12, 13, 14, 15, 16, 17, 18, 19, 20, 21, 22, 23 miRNAs, selected from the group consisting of hsa-miR-188-3p, hsa-miR-382-3p, hsa-miR-330-3p, hsa-miR-369-3p, hsa-miR-127-3p, hsa-miR-155-5p, hsa-miR-1908, hsa-miR-190a, hsa-miR-203a, hsa-miR-214-3p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-let-7b-5p.

According to a specific embodiment of the invention there is provided a method, wherein hsa-miR-330-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27 miRNAs, selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

According to a specific embodiment of the invention there is provided a method, wherein hsa-miR-330-3p is measured in combination with at least one miRNA, specifically 2, 3, 4, 5, 6 miRNAs, selected from the group consisting of hsa-miR-188-3p, hsa-miR-144-3p, hsa-miR-335-5p, hsa-miR-31-5p, hsa-miR-29b-4p, and hsa-miR-181d and optionally in combination with at least one miRNA, specifically 2, 3, 4, 5, 6, 7, 8, 9, 10, 11, 12, 13, 14, 15, 16, 17, 18, 19, 20 miRNAs, selected from the group consisting of hsa-miR-127-3p, hsa-miR-155-5p, hsa-miR-1908, hsa-miR-190a, hsa-miR-199b-5p, hsa-miR-214-3p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p and hsa-miR-942.

According to a specific embodiment of the invention there is provided a method, wherein hsa-miR-330-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-382-3p, hsa-miR-181a-3p, hsa-miR-369-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-29b-3p, hsa-miR-342-5p, hsa-miR-335-5p, hsa-miR-31-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p, and hsa-miR-181d.

According to a specific embodiment of the invention there is provided a method, wherein hsa-miR-330-3p is measured in combination with at least one miRNA, specifically 2, 3, 4, miRNAs, selected from the group consisting of hsa-miR-144-3p, hsa-miR-29b-3p, hsa-miR-335-5p and hsa-miR-31-5p, and hsa-miR-181d and optionally in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-188-3p, hsa-miR-382-3p, hsa-miR-181a-3p, hsa-miR-369-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-let-7b-5p.

According to a specific embodiment of the invention there is provided a method, wherein hsa-miR-369-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26 miRNAs, selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

According to a specific embodiment of the invention there is provided a method, wherein hsa-miR-369-3p is measured in combination with at least one miRNA, specifically 2, 3, 4, 5 miRNAs, selected from the group consisting of hsa-miR-144-3p, hsa-miR-335-5p, hsa-miR-31-5p, hsa-miR-29b-4p and hsa-miR-181d and optionally in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-miR-127-3p, hsa-miR-155-5p, hsa-miR-188-3p, hsa-miR-1908, hsa-miR-190a, hsa-miR-199b-5p, hsa-miR-214-3p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p and hsa-miR-942.

According to a specific embodiment of the invention there is provided a method, wherein hsa-miR-369-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-382-3p, hsa-miR-181a-3p, hsa-miR-330-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-29b-3p, hsa-miR-342-5p, hsa-miR-335-5p, hsa-miR-31-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p, and hsa-miR-181d.

According to a specific embodiment of the invention there is provided a method, wherein hsa-miR-369-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25 miRNAs, selected from the group consisting of hsa-miR-144-3p, hsa-miR-29b-3p, hsa-miR-335-5p, hsa-miR-31-5p and hsa-miR-181d and in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-382-3p, hsa-miR-181a-3p, hsa-miR-330-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-let-7b-5p.

According to a specific embodiment of the invention there is provided a method, wherein hsa-miR-203a is measured in combination with at least one miRNA, specifically 2, 3, 4, 5, 6, 7, 8, 9, 10, 11, 12, 13, 14, 15, 16, 17, 18, 19, 20, 21, 22, 23 miRNAs, selected from the group consisting of hsa-miR-127-3p, hsa-miR-155-5p, hsa-miR-188-3p, hsa-miR-1908, hsa-miR-190a, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and miR-181d.

According to a specific embodiment of the invention there is provided a method, wherein hsa-miR-203a is measured in combination with at least one miRNA, specifically 2, 3, 4 miRNAs, selected from the group consisting of hsa-miR-335-5p, hsa-miR-31-5p, hsa-miR-29b-4p and miR-181d and optionally in combination with at least one miRNA, specifically 2, 3, 4, 5, 6, 7, 8, 9, 10, 11, 12, 13, 14, 15, 16, 17, 18, 19 miRNAs, selected from the group consisting of hsa-miR-127-3p, hsa-miR-155-5p, hsa-miR-188-3p, hsa-miR-1908, hsa-miR-190a, hsa-miR-214-3p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p and hsa-miR-942.

According to a specific embodiment of the invention there is provided a method, wherein hsa-miR-203a is measured in combination with at least one miRNA, specifically 2, 3, 4, 5, 6, 7, 8, 9, 10, 11, 12, 13, 14, 15, 16, 17, 18, 19, 20, 21, 22, 23, 24, 25, 26, 27, 28, 29 miRNAs, selected from the group consisting of hsa-miR-144-3p, hsa-miR-188-3p, hsa-miR-382-3p, hsa-miR-181a-3p, hsa-miR-330-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-29b-3p, hsa-miR-342-5p, hsa-miR-335-5p, hsa-miR-31-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p, and hsa-miR-181d.

According to a specific embodiment of the invention there is provided a method, wherein hsa-miR-203a is measured in combination with at least one miRNA, specifically 2, 3, 4miRNAs, selected from the group consisting of hsa-miR-144-3p, hsa-miR-29b-3p, hsa-miR-335-5p, hsa-miR-31-5p and optionally in combination with at least one miRNA, specifically 2, 3, 4, 5, 6, 7, 8, 9, 10, 11, 12, 13, 14, 15, 16, 17, 18, 19, 20, 21, 22, 23, 24, 25 miRNAs, selected from the group consisting of hsa-miR-188-3p, hsa-miR-382-3p, hsa-miR-181a-3p, hsa-miR-330-3p, hsa-miR-127-3p, hsa-miR-155-5p, hsa-miR-1908, hsa-miR-190a, hsa-miR-199b-5p, hsa-miR-203a, hsa-miR-214-3p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p, and hsa-miR-181d.

According to a further embodiment of the invention there is provided an in vitro method of diagnosing osteoporosis or determining the risk of osteoporotic fractures or monitoring of treatment in a subject, which can be but is not limited to a patient being at risk of or suffering from type 2 diabetes mellitus, comprising the steps of:

a) providing a sample, specifically a blood sample, from said subject, b) measuring the level of two or more miRNAs, specifically 2, 3, 4, 5, 6, 7, 8, 9, 10, 11, 12, 13, 14, 15, 16, 17, 18, 19, 20, 21, 22, 23, 24, 25, 26 miRNAs, selected from any of miRNAs consisting of hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-550a-5p, hsa-miR-7-5p, hsa-miR-92a-3p, hsa-miR-942, hsa-miR-96-5p hsa-miR-330-3p, hsa-miR-31-5p, hsa-miR-144-3p, and hsa-miR-382-3p, and c) comparing the level of said miRNAs to a reference level, wherein the magnitude of difference in said level when compared to the reference level is indicative of osteoporosis or the risk of fractures.

According to a further embodiment of the invention there is provided an in vitro method of diagnosing osteoporosis or determining the risk of osteoporotic fractures or monitoring of treatment in a subject, comprising the steps of:

a) providing a sample from said subject, b) measuring the level of 1, 2, 3, 4 or 5 miRNAs selected from any of miRNAs consisting of hsa-miR-486-5p, hsa-miR-330-3p, hsa-miR-31-5p, hsa-miR-144-3p, and hsa-miR-382-3p, and c) measuring the level of 1, 2, 3, 4, 5, 6, 7, 8, 9, 10, 11, 12, 13, 14, 15, 16, 17, 18, 19, 20, 21 miRNAs selected from any of miRNAs consisting of miRNAs consisting of hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-500a-5p, hsa-miR-550a-5p, hsa-miR-7-5p, hsa-miR-92a-3p, hsa-miR-942, hsa-miR-96-5p, and d) comparing the level of said miRNAs to a reference level, wherein the magnitude of difference in said levels when compared to the reference levels is indicative of osteoporosis or the risk of fractures.

According to a specific embodiment of the invention there is provided a method, wherein at least one miRNA selected from the group consisting of hsa-miR-32-3p, hsa-miR-181c-3p, hsa-miR-323a-3p, hsa-miR-550a-5p and hsa-miR-96-5p and at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-let-7b-5p, hsa-let-7g-5p, hsa-let-7i-5p, hsa-miR-141-3p, hsa-miR-143-5p, hsa-miR- 16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p are measured.

According to a further specific embodiment of the invention, 2, 3, 4 or 5 of hsa-miR-32-3p, hsa-miR-181c-3p, hsa-miR-323a-3p, hsa-miR-550a-5p and hsa-miR-96-5p can be measured in combination with at least one miRNA, specifically 2, 3, 4, 5, 6, 7, 8, 9, 10, 11, 12, 13, 14, 15, 16, 17, 18, 19, 20, 21 miRNAs, selected from hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-32-3p is measured in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-32-3p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p. According to a specific embodiment of the invention there is provided a method, wherein hsa-miR-32-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25 miRNAs, selected from the group consisting of hsa-miR-181c-3p, hsa-miR-323a-3p, hsa-miR-550a-5p, hsa-miR-96-5p hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-32-3p is measured in combination with hsa-miR-31-5p, and optionally in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-181c-3p, hsa-miR-323a-3p, hsa-miR-550a-5p, hsa-miR-96-5p hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p. According to a specific embodiment of the invention there is provided a method, wherein hsa-miR-181c-3p is measured in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-181c-3p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-181c-3p is measured in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-323a-3p, hsa-miR-550a-5p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-181c-3p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20, 21, 22, 23 miRNAs, selected from the group consisting of hsa-miR-323a-3p, hsa-miR-550a-5p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-323a-3p is measured in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-323a-3p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-323a-3p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25 miRNAs, selected from the group consisting of hsa-miR-32-3p, hsa-miR-323a-3p, hsa-miR-550a-5p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-323a-3p is measured in combination with hsa-miR-31-5p, and optionally in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-32-3p, hsa-miR-323a-3p, hsa-miR-550a-5p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-550a-5p is measured in combination with at least one miRNA, specifically 2, 3, 4, 5, 6, 7, 8, 9, 10, 11, 12, 13, 14, 15, 16, 17, 18, 19, 20, 21 miRNAs, selected from the group consisting, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-550a-5p is measured in combination with hsa-miR-31-5p, and optionally in combination with at least one miRNA, specifically 2, 3, 4, 5, 6, 7, 8, 9, 10, 11, 12, 13, 14, 15, 16, 17, 18, 19, 20, 21 miRNAs, selected from the group consisting, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-550a-5p is measured in combination with at least one miRNA, specifically 2, 3, 4, 5, 6, 7, 8, 9, 10, 11, 12, 13, 14, 15, 16, 17, 18, 19, 20, 21, 23, 24, 25 miRNAs, selected from the group consisting of hsa-miR-32-3p, hsa-miR-181c-3p, hsa-miR-323a-3p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-550a-5p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20, 21, 23, 24 miRNAs, selected from the group consisting of hsa-miR-32-3p, hsa-miR-181c-3p, hsa-miR-323a-3p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-96-5p is measured in combination with at least one miRNA, specifically 2, 3, 4, 5, 6, 7, 8, 9, 10, 11, 12, 13, 14, 15, 16, 17, 18, 19, 20, 21 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-96-5p is measured in combination with hsa-miR-31-5p, and optionally in combination with at least one miRNA, specifically 2, 3, 4, 5, 6, 7, 8, 9, 10, 11, 12, 13, 14, 15, 16, 17, 18, 19, 20 miRNAs, selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

According to a specific embodiment of the invention there is provided a method, wherein hsa-miR-96-5p is measured in combination with at least one miRNA, specifically 2, 3, 4, 5, 6, 7, 8, 9, 10, 11, 12, 13, 14, 15, 16, 17, 18, 19, 20, 21, 22, 23, 24, 25 miRNAs, selected from the group consisting of hsa-miR-32-3p, hsa-miR-181c-3p, hsa-miR-323a-3p, hsa-miR-550a-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

According to a specific embodiment of the invention there is provided a method, wherein hsa-miR-96-5p is measured in combination with hsa-miR-31-5p and optionally in combination with at least one miRNA, specifically 2, 3, 4, 5, 6, 7, 8, 9, 10, 11, 12, 13, 14, 15, 16, 17, 18, 19, 20, 21, 22, 23, 24 miRNAs, selected from the group consisting of hsa-miR-32-3p, hsa-miR-181c-3p, hsa-miR-323a-3p, hsa-miR-550a-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-144-3p and hsa-miR-382-3p.

In case the present invention is used for monitoring the treatment of a subject, the treatment may be adjusted respectively.

In an alternative embodiment of the invention, the level of said miRNAs can be compared with the average level of corresponding miRNAs in healthy subjects, specifically in a pool of samples derived from healthy subjects, wherein a difference by more than one standard deviations, specifically by about 1.5, 1.6, 1.7, 1.8, 1.9, specifically about 2 standard deviations or more is indicative of osteoporosis with increased risk of future fractures, specifically of osteoporotic fractures.

According to a further embodiment, a difference by more than 2.5 standard deviations, specifically about 3, specifically about 3.5, specifically more than 3.5 standard deviations is indicative of osteoporosis with high risk of future fractures, specifically of osteoporotic fractures.

Thus it is within the embodiment of the invention to use either a single reference sample from a healthy subject or a pool of samples derived from healthy subjects for comparison with the respective sample from a subject to be diagnosed. Said pool can consist of 2, 3, 4, 5, 6, 7, or more samples, specifically up to 10, 100 or more than 100 samples from different individuals.

According to a further embodiment a method is provided, wherein the level of said miRNAs is compared with the average level of corresponding miRNAs in healthy subjects, wherein a difference by more than one standard deviation is indicative of osteoporosis with increased risk of future fractures.

According to a specific embodiment, a method is provided, wherein the level of at least 3, preferably at least 4, preferably at least 5, specifically up to 30 miRNAs of hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-335-5p, hsa-miR-31-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and hsa-miR-181d are measured, specifically for diagnosing non-diabetic subjects.

According to a specific embodiment a method is provided, wherein the level of at least 3, preferably at least 4, preferably at least 5, specifically up to 26 miRNAs of hsa-miR-32-3p, hsa-miR-181c-3p, hsa-miR-323a-3p, hsa-miR-550a-5p, hsa-miR-96-5p, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and miR-382-3p are measured, specifically for diagnosing Type II-diabetic subjects.

According to a specific embodiment, a single diagnostic assay is provided for diagnosing post-menopausal females, osteoporosis or osteopenia patients, suffering from or being at risk of developing bone fractures, ad patients being at risk or suffering from diabetes mellitus Type 2 wherein more than one and up to 30hsa-miRNAs of the inventive list of miRNAs are measured according to the present invention.

Specifically, at least one of hsa-miR-188-3p, hsa-miR-382-3p, hsa-miR-181a-3p, hsa-miR-330-3p and hsa-miR-369-3p, hsa-miR-32-3p, hsa-miR-181c-3p, hsa-miR-323a-3p, hsa-miR-550a-5p and hsa-miR-96-5p is measured together with at least one of hsa-miR-127-3p, hsa-miR-155-5p, hsa-miR-1908, hsa-miR-190a, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-576-3p, hsa-miR-582-3p, hsa-miR-642a-5p, hsa-miR-94, miR181d, hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-31-5p, hsa-miR-144-3p and hsa-miR-382-3p According to a specific embodiment a method is provided, wherein the level of 24, 25, 26, 27, 28, 29, 30, 31, 32, 33, 34, 35, 36, 37, 38, 39, 40, 41, 42, 43, 45, 46 miRNAs is measured, specifically for providing a diagnostic system wherein non-diabetic and diabetic subjects can be diagnosed according to the invention.

According to a specific embodiment a method is provided, wherein one or more further miRNAs are detected, wherein said miRNAs are
a) differentially regulated in osteoporotic individuals as compared to healthy individuals and are
b) involved in osteogenic differentiation and/or in osteoclastogenic activation.

According to a specific embodiment of the invention, there is provided the use of the inventive method for monitoring a subject, specifically for the prognosis of bone fraction.

According to a specific embodiment of the invention, there is provided the use of the inventive method for monitoring a subject, specifically for measuring the response of a subject to anti-osteoporotic treatments.

According to a specific embodiment a method is provided, wherein the difference in miRNA levels is determined by quantitative or digital PCR, sequencing, microarray, Luminex nucleic acid assays, or other hybridization-based techniques.

The present invention also provides a composition for use in treating or preventing osteoporosis or fractures comprising
a) at least two synthetic human miRNAs from miRNAs as described above, and/or
b) an antagonist/inhibitor of at least two of miRNAs as described above, that
i. decreases the level of said miRNAs; and/or
ii. inhibits or down-regulates expression of the sequences coding for said miRNAs or degrades or cleaves said miRNAs.

The present invention also provides a composition for use in treating or preventing osteoporosis or fractures comprising
a) at least one synthetic human miRNA selected from hsa-miR-188-3p, hsa-miR-382-3p und hsa-miR-550a-5p and/or
b) an antagonist/inhibitor of at least one of miRNAs hsa-miR-188-3p, hsa-miR-382-3p und hsa-miR-550a-5p, that
i. decreases the level of said miRNAs; and/or
ii. inhibits or down-regulates expression of the sequences coding for said miRNAs or degrades or cleaves said miRNAs.

According to an embodiment of the invention, the use of a composition comprising at least one, specifically at least two synthetic human miRNAs as specified above and/or an antagonist/inhibitor of at least two of miRNAs as specified above that decreases the level of said miRNAs; and/or inhibits or down-regulates expression of the sequences coding for said miRNAs or degrades or cleaves said miRNAs for preparing a medicament.

In a further embodiment, the present invention provides a method for treating a subject which was diagnosed osteoporosis or the risk of osteoporotic fractures using any one of the in vitro methods as described herein, wherein the treatment comprises administering a drug to said subject, said drug being known by the skilled artisan for treating osteoporosis or prophylactic treatment of bone fractures. Said drugs can be, but are not limited to calcium (calcitonin, Fortical®, Miacalcin®, Calcichew®, Osteofos®, Caltrate Plus®), vitamin D, bisphosphonates like alendronate (Fosamax®, Reclast®), etidronate, risedronate (Actonel®), ibandronate (Boniva®), zoledronic acid (Reclast), hormones, such as estrogen, and hormone-like medications approved for preventing and treating osteoporosis, such as estrogen agonists/antagonists, raloxifene (Evista®), strontium ranelate, monoclonal antibodies, e.g. monoclonal antibodies against RANKL or Sclerostin, like e.g. denosumab (Prolia®), teriparatide (Forteo®), bazedoxifine acetate (Combriza®).

FIGURES

FIG. 1: Multi-parameter models for the classification of post-menopausal women with osteoporosis. A classification of osteoporotic cases versus controls was performed by testing any possible combination of at least 2 up to 10 microRNAs (red boxplots) selected from 23 microRNAs against a negative control data set (grey boxplots). The data clearly show, that the combinations of at least 2 microRNAs yield significantly better results for the classification of post-menopausal women with fractures than random.

Figure 2:
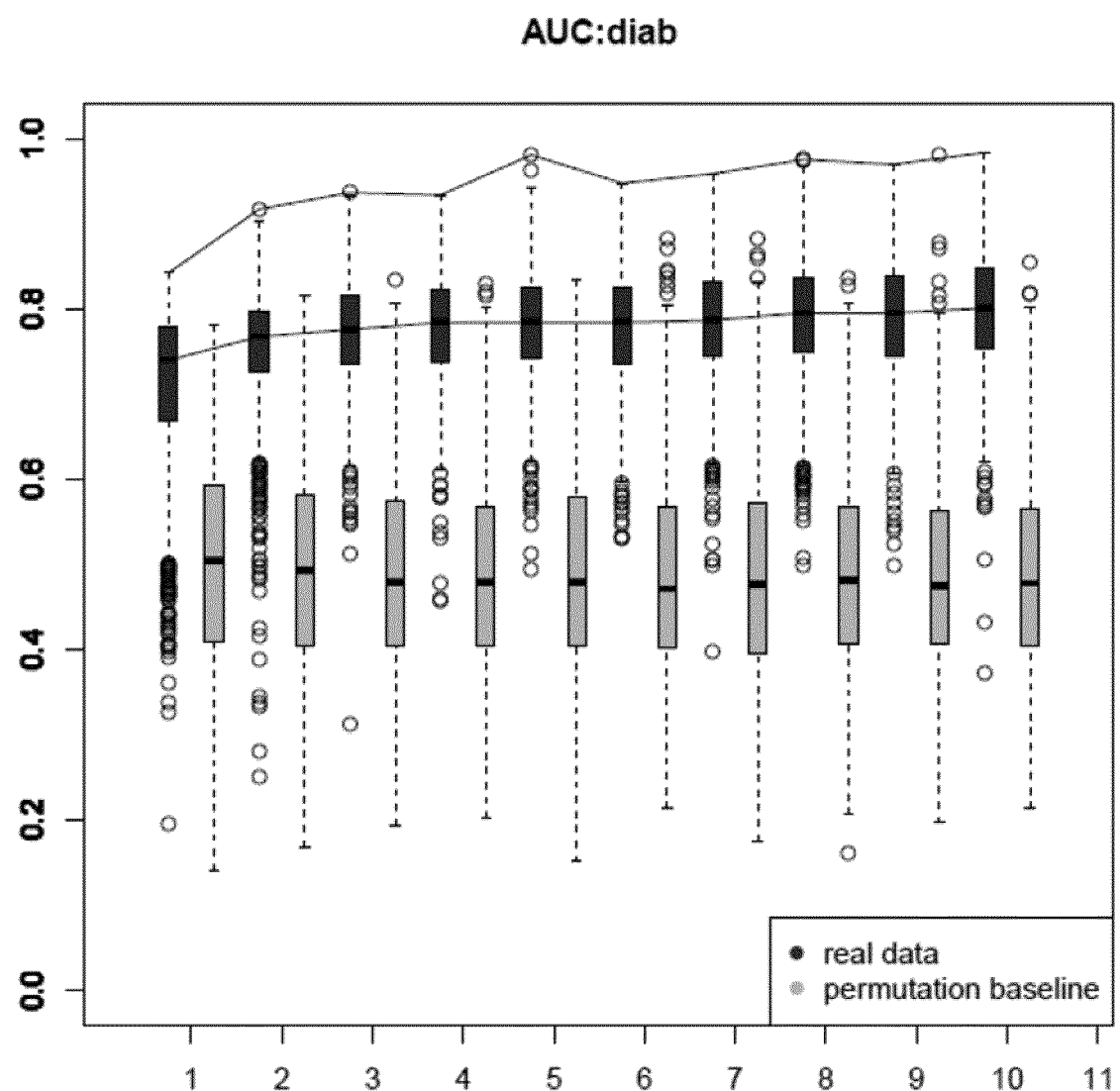

FIG. 2: Multi-parameter models for the classification of diabetic post-menopausal women with osteoporosis. A classification of diabetic osteoporotic cases versus controls was performed by testing any possible combination of at least 2 up to 10 microRNAs (black boxplots) selected from 23 microRNAs against a negative control data set (grey boxplots). The data clearly show, that the combinations of at least 2 microRNAs yield significantly better results for the classification of diabetic post-menopausal women with fractures than random.

Figure 3:
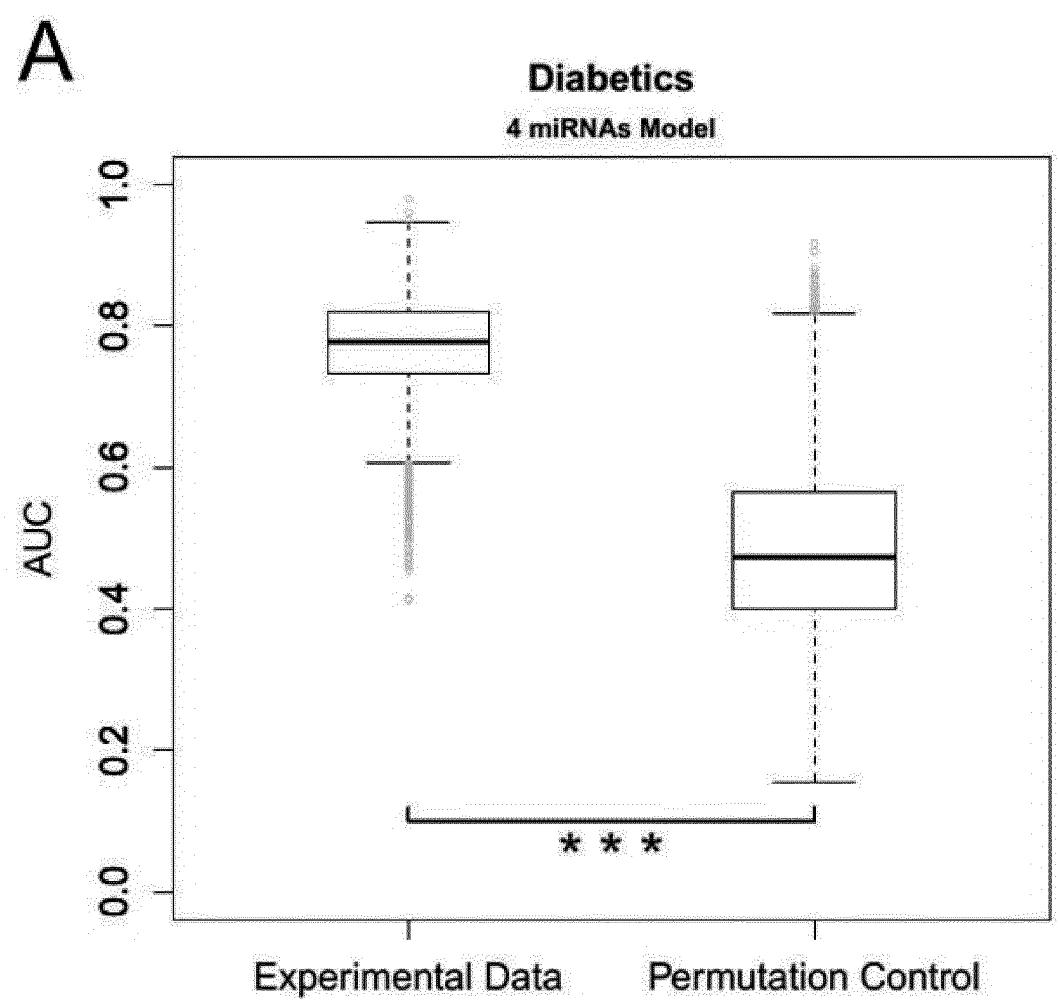
Figure 3:
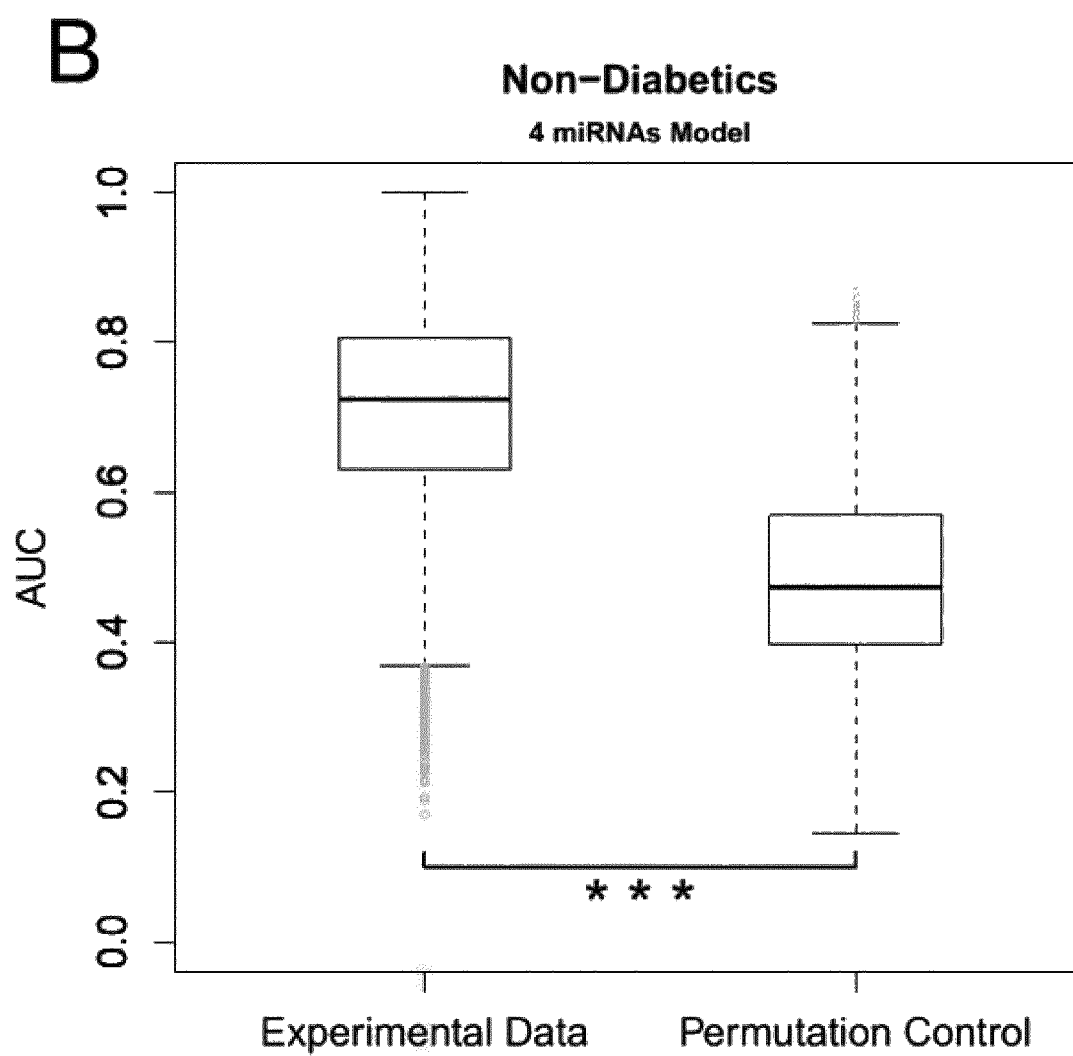

FIG. 3: Four-parameter models for the classification of diabetic (A) and non-diabetic (B) post-menopausal women with osteoporosis. The data show the results from testing any combination of four microRNAs out of the list of 23 pre-selected microRNAs for the classification of diabetic (A) and non-diabetic (B) patients with osteoporosis.

Figure 4:
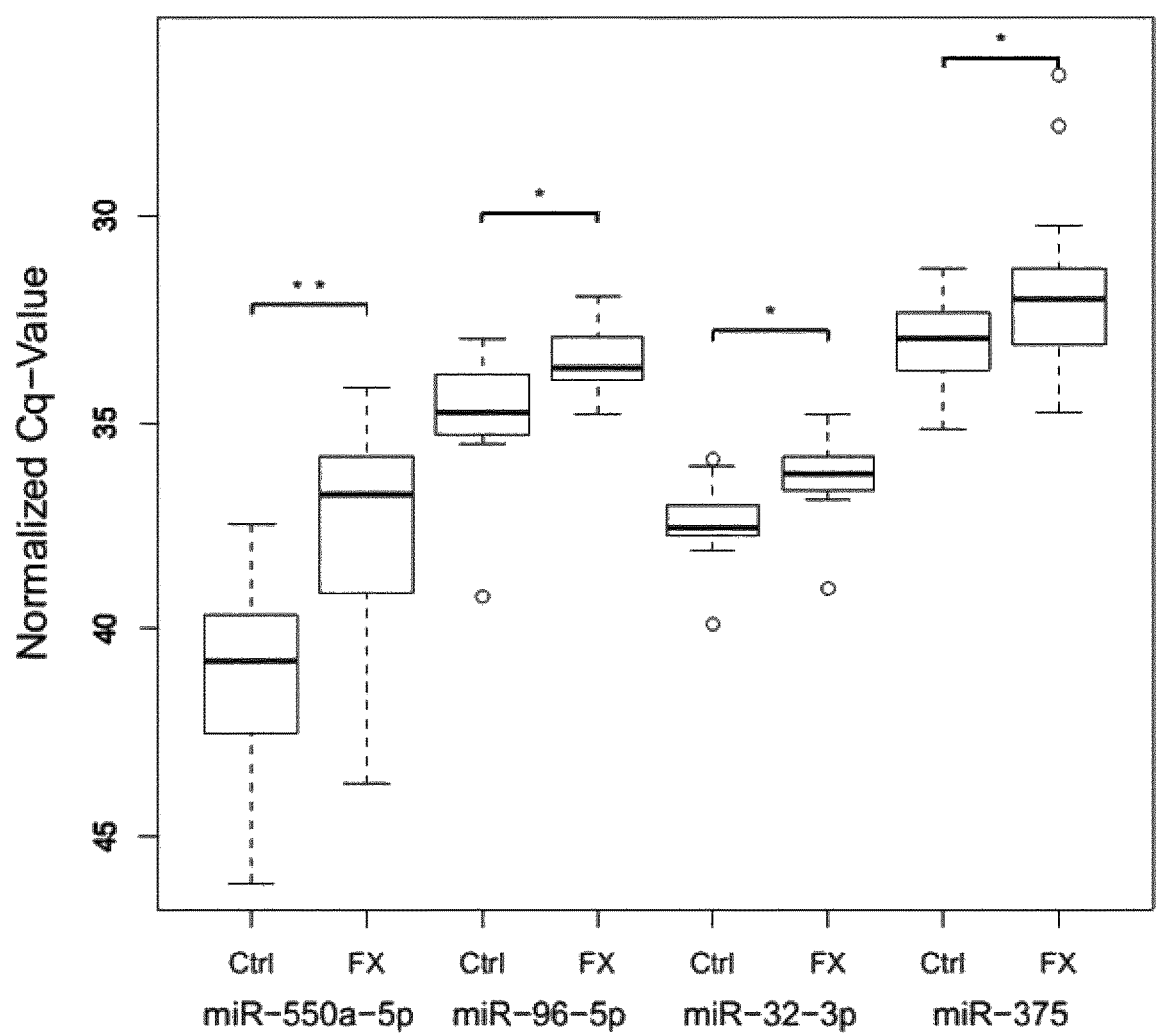
Figure 4:
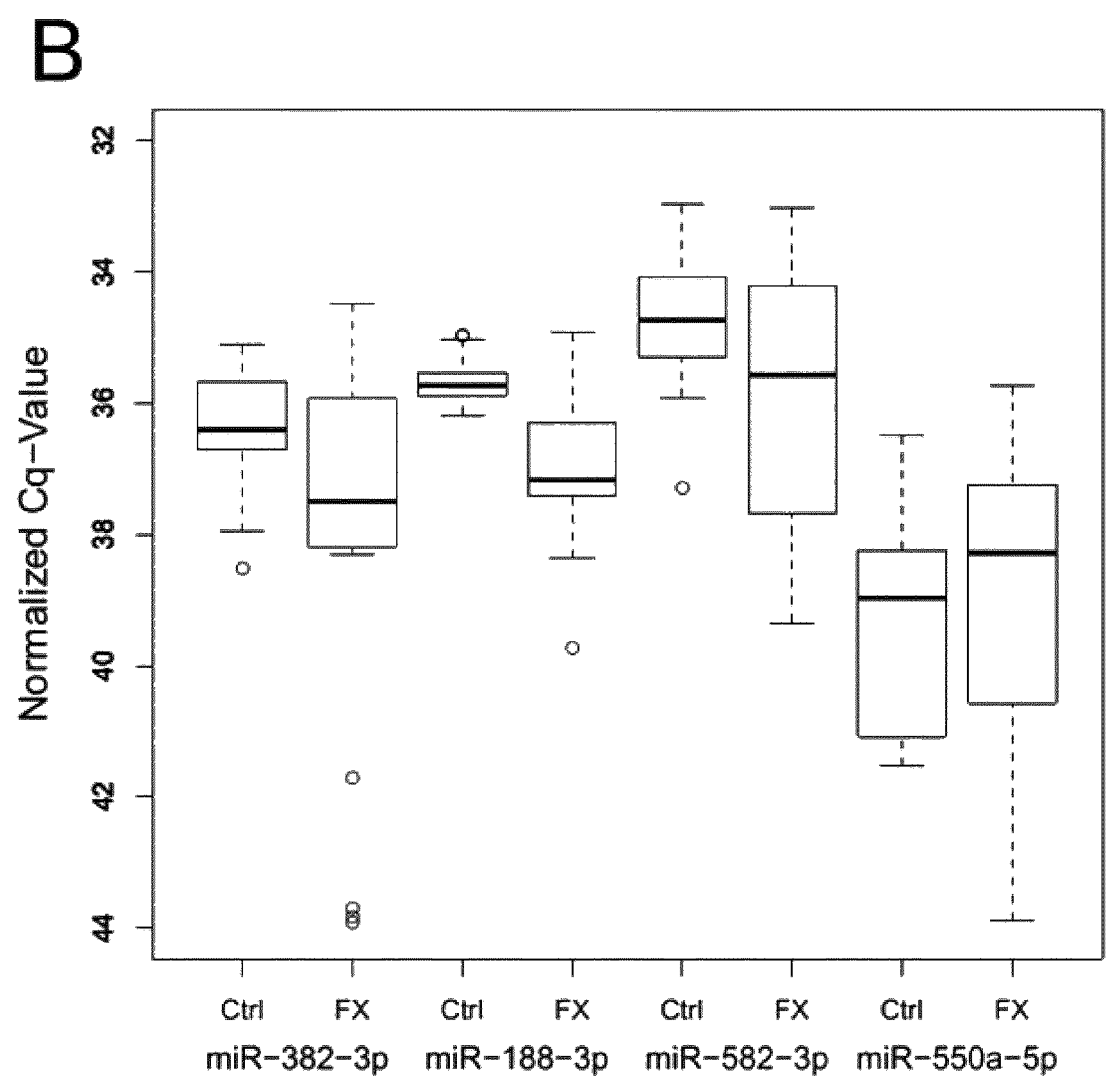

FIG. 4: Serum levels of microRNAs in diabetic (A) and non-diabetic (B) osteoporotic cases and controls. Shown are the Cq levels of microRNAs, which were determined by quantitative PCR, that were part of the top-performing classification model for diabetic (A) or non-diabetic (B) osteoporosis, respectively.

Figure 5:
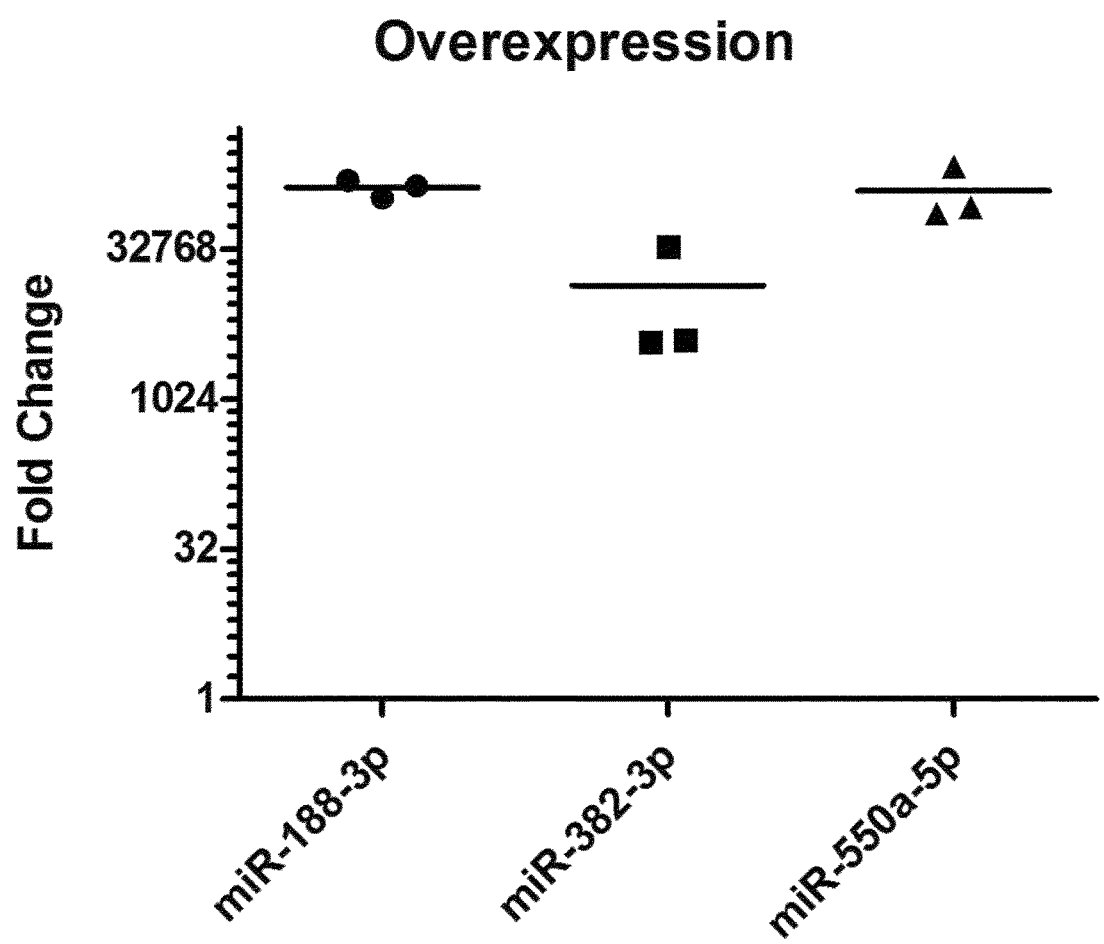
Figure 5:
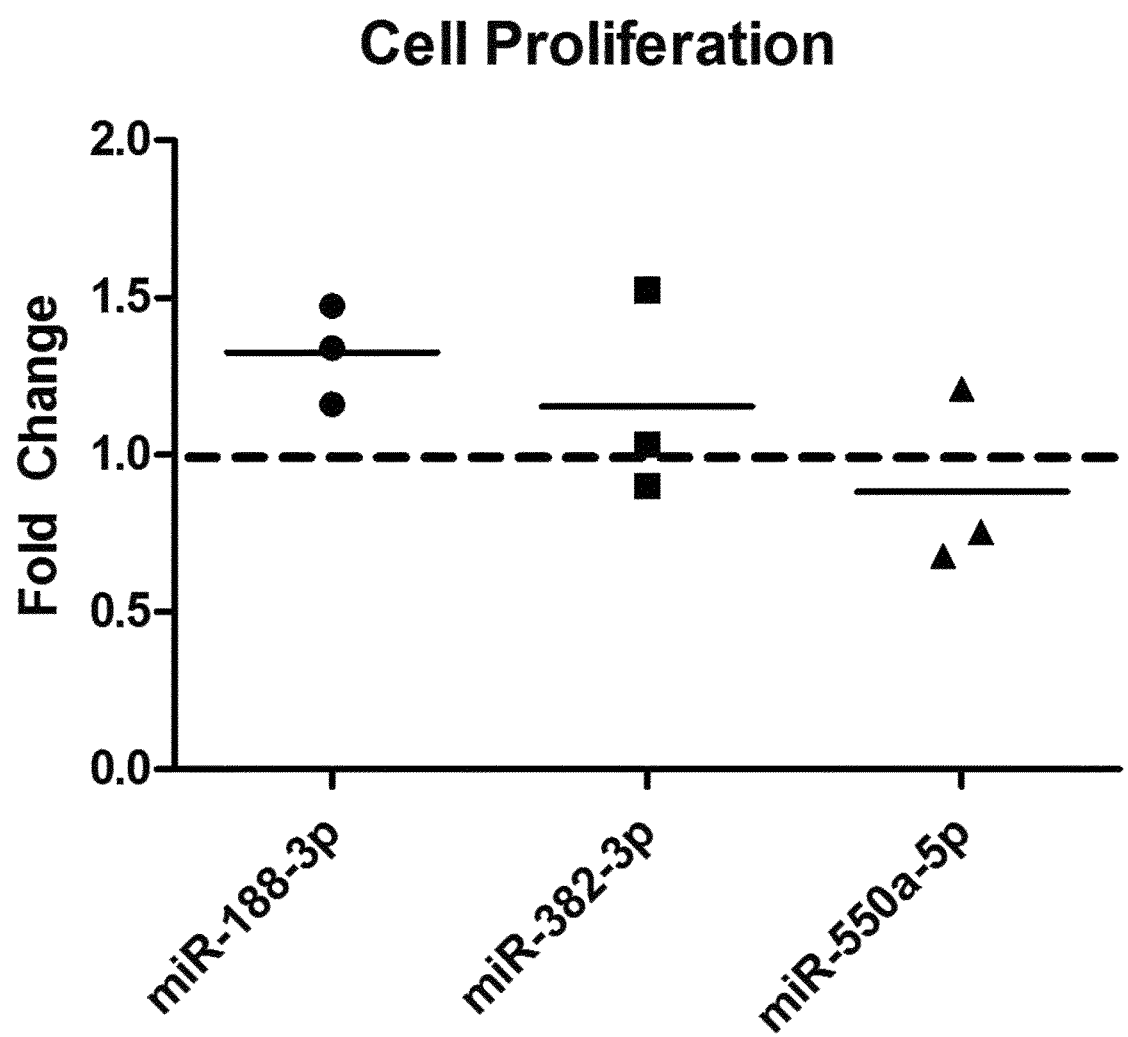
Figure 5:
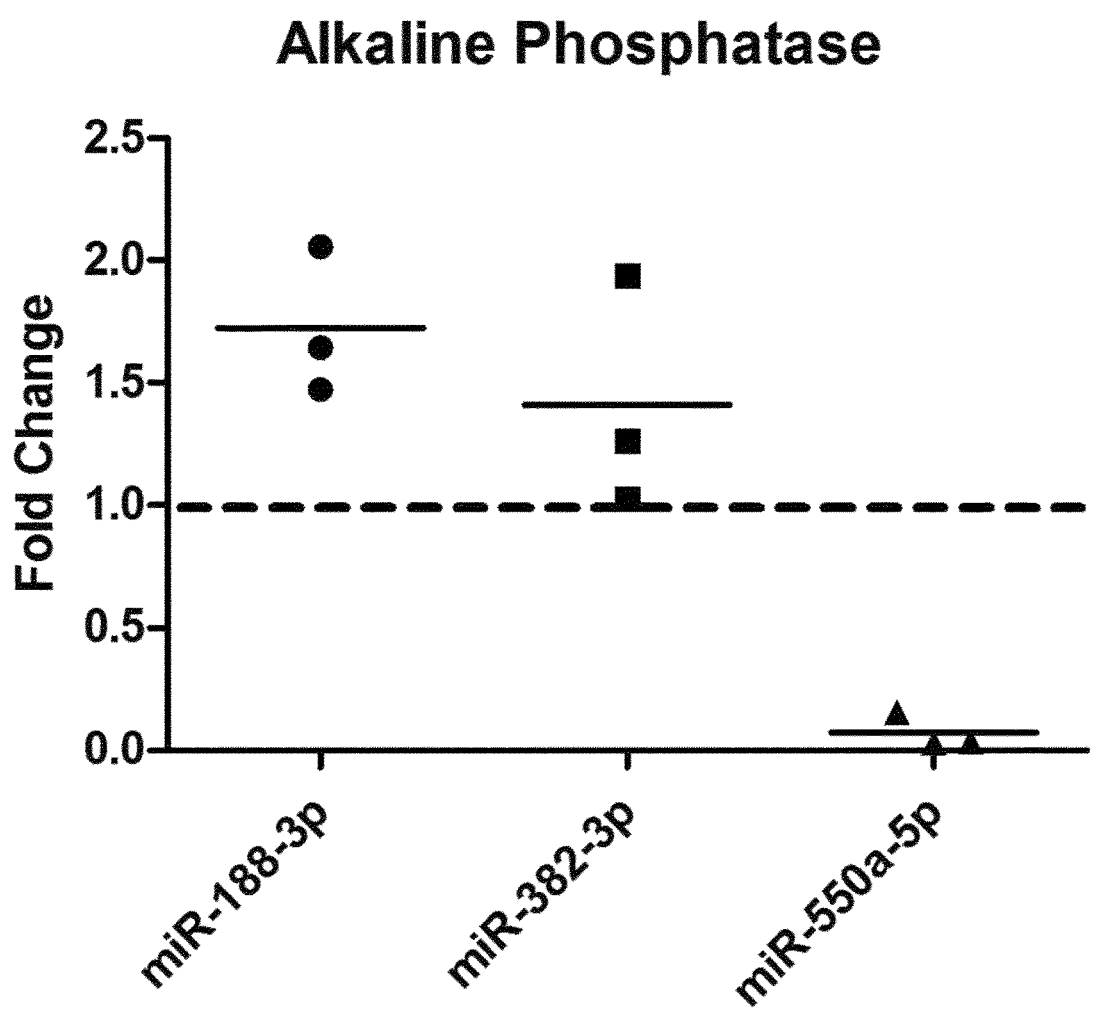
Figure 5:
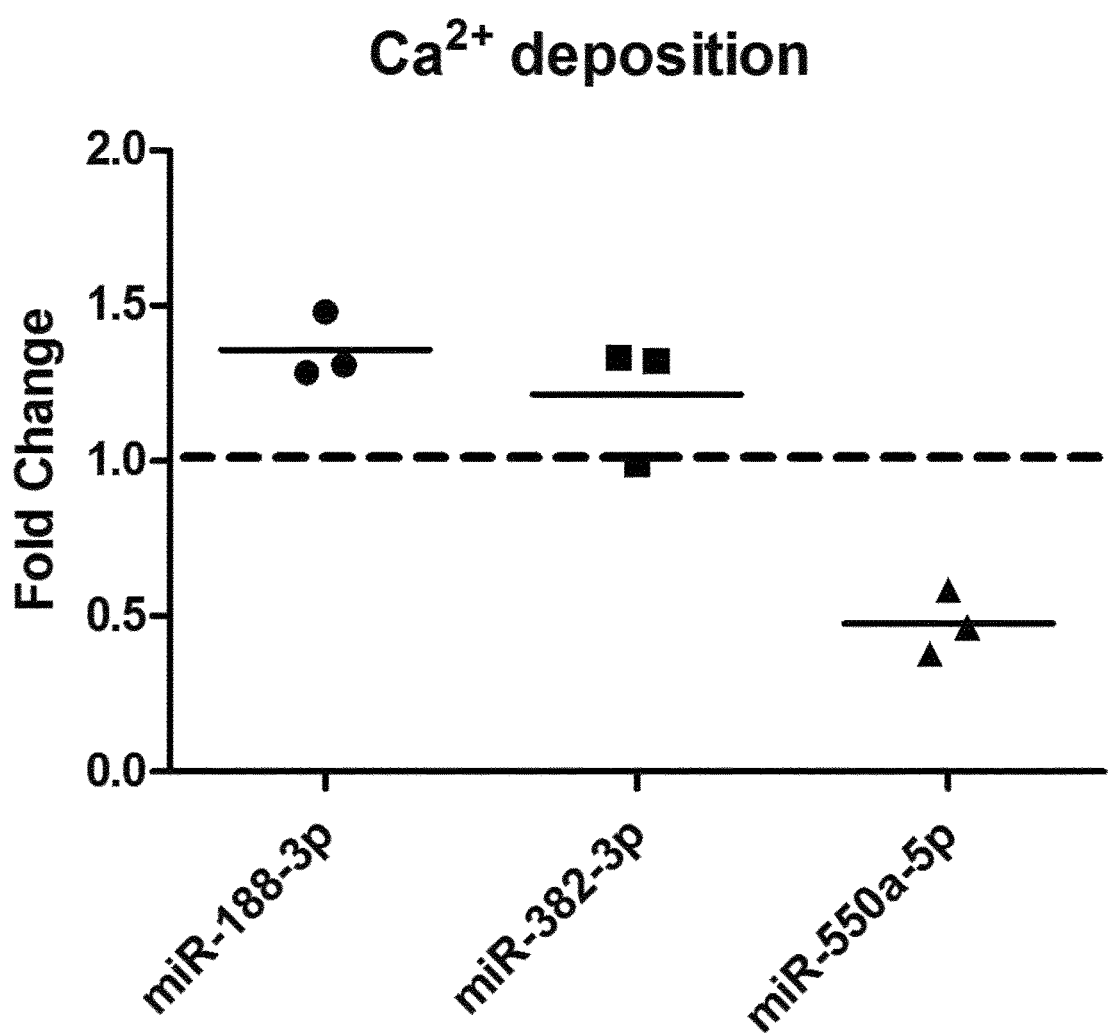

FIG. 5: Therapeutic efficacy of three selected microRNAs: miR-188-3p, miR-382-3p, miR-550a-5p. (A) microRNAs were overexpressed in mesenchymal stem cells through electroporation. High levels of overexpression were achieved for all three microRNAs. (B) The impact of microRNA overexpression on cell proliferation. (C) The impact of microRNA overexpression on Alkaline Phosphatase activity, which is indicative of bone formation, was tested. miR-188-3p and miR-382-3p significantly improved osteogenic differentiation, while miR-550a-5p inhibited osteogenic differentiation. (D) Effects on Calcium deposition are shown, which is another important characteristic of stem cells undergoing osteogenic differentiation.

DETAILED DESCRIPTION OF THE INVENTION

Osteogenic differentiation is defined as the process during which a mesenchymal stem cell or adipose tissue derived stem cell becomes activated to proliferate and differentiate into an osteoblast. This process is characterized by secretion of alkaline phosphatase (ALP), changes in gene expression such as Osteocalcin, RUNX2, ALP, and elevated calcium incorporation.

Osteoclastogenic formation is defined as the process during which monocytes (i.e. macrophages) are activated by RANKL and M-CSF to form osteoclasts, which are characterized by release of $H^+$, specific proteases and other enzymes such as tartrate resistant acidic phosphatase (TRAP), Cathepsin K, which assist in bone resorption.

As used in this specification and the appended claims, the singular forms "a", "an", and "the" include plural referents, unless the content clearly dictates otherwise.

As used herein, the term "blood sample" refers to serum, plasma, whole blood and its components, blood derived products or preparations. Plasma and serum are very useful as shown in the examples.

The term "sample" generally refers to blood sample and urine, saliva and cerebrospinal fluid.

As used herein, the term "subject" or "individual" or "patient" shall refer to a warm-blooded mammalian, particularly a human being.

The term "patient" includes human and other mammalian subjects that receive either prophylactic or therapeutic treatment or are diagnosed of a specific disease, like but not limited to osteoporosis or diabetes mellitus.

Specifically, a change in the level of miRNAs selected from of hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-31-5p, hsa-miR-335-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and miR181d compared to the level of these miRNAs in healthy subjects are highly indicative for the risk of osteoporotic fractures in post-menopausal women or osteoporosis or osteopenia patients, suffering from or being at risk of developing bone fractures.

Specifically, a change in the level of miRNAs selected from hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-550a-5p, hsa-miR-7-5p, hsa-miR-92a-3p, hsa-miR-942, hsa-miR-96-5p, hsa-miR-330-3p, hsa-miR-31-5p, hsa-miR-144-3p, and miR382-3p compared to the level of these miRNAs in healthy subjects are highly indicative for the risk of osteoporotic fractures in patients being at risk of or suffering from type 2 diabetes mellitus.

The term "treatment" relates to any treatment which improves the health status, reduces or inhibits unwanted weight loss and/or prolongs and/or increases the lifespan of an individual. Said treatment may eliminate the disorder in an individual, arrest or slow the development of a disease in an individual, inhibit or slow the development of a disease in an individual, decrease the frequency or severity of symptoms in an individual, and/or decrease the recurrence in an individual who currently has or who previously has had a disorder. The terms "prophylactic treatment" or "preventive treatment" can be used interchangeably and relate to any treatment that is intended to prevent a disease from occurring in a subject.

As used herein, "preventing" or "prevention" of a disease, disorder or condition refers to the reduction of the occurrence of the disorder or condition in a treated subject relative to an untreated control subject, or delays the onset or reduces the severity of one or more symptoms of the disorder or condition relative to the untreated control subject. The terms "protect", "prevent", "prophylactic", "preventive", or "protective" relate to the prevention and/or treatment of the occurrence and/or the propagation of a disease.

The term "post-menopausal" women refer to women who had not had their period for at least one year. The term "type-II diabetic" refers to individuals who have received antidiabetic medication for at least 3 years in the form of oral medication and/or insulin, and/or who fulfil the diagnostic criteria of the American Diabetes Association (American Diabetes Association, Diagnosis and classification of diabetes mellitus, Diabetes Care. 2014; 37 Suppl 1:S81-90).

As used therein, the term "cohort of individuals" or "pool of individuals" shall refer to a group of healthy individuals and may specifically refer to the samples received from said individuals. The number of individuals of a cohort can vary, i.e. it may comprise 2, 3, 4, 5, 6, 7 or more individuals, however it also may be a larger group of subjects, like for example but not limited to 10, 50, 100 or more individuals. According to the embodiment of the invention the cohort may also comprise large cohorts of 500 or more individuals.

According to the invention, the term "about" encompasses the explicitly recited values as well as small deviations therefrom. Accordingly, a deviation from a recited value for 10%, preferably 5%, preferably 1% is encompassed by the term "about".

According to the invention, subjects with primary osteoporosis (post-menopausal) with mean ages of about 60 years were assessed, which stands in contrast to bone loss and fracture risk due to senile osteoporosis, which affects subjects of about 70 years or older.

The term "treatment success" as used herein is defined as maintaining the bone density or delaying the process of osteoporosis and decreasing the risk of breaking a bone (osteoporotic fracture) as a result of osteoporosis. Hence, a marker that predicts treatment success should be preferentially related to the clinical outcome for a patient, i.e. the reduction in fracture risk. Moderate treatment success reduces fracture risk by about 25% up to about 50%. High treatment success results in a risk reduction by more than 50%.

A "control", "control sample", or "reference value" are terms which can be used interchangeably herein, and are to be understand as a sample or standard used for comparison with the experimental sample. The control may include a sample obtained from a healthy subject or a subject, which is not at risk of or suffering from developing bone fracture or type 2 diabetes mellitus. Additionally, a control may also be a standard reference value or range of values, i.e. such as stable expressed miRNAs in the samples, for example the endogenous control cel-miR-39.

The present invention provides selected miRNAs for use in a method for diagnosing osteoporosis, determining the risk of developing osteoporotic lessons or fractures or monitoring the treatment in subjects undergoing therapy, specifically osteoporosis or diabetes treatment.

Said first group of miRNAs are, preferably for diagnosing osteoporosis or determining the risk of osteoporotic fractures or monitoring of treatment in post-menopausal females or osteoporosis or osteopenia patients, suffering from or being at risk of developing bone fractures, hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-31-5p, hsa-miR-335-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and hsa-miR181d or isoforms or variants thereof.

Said second group of miRNAs are, preferably for diagnosing osteoporosis or determining the risk of osteoporotic fractures or monitoring of treatment in patients being at risk of or suffering from type 2 diabetes mellitus, hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-550a-5p, hsa-miR-7-5p, hsa-miR-92a-3p, hsa-miR-942, hsa-miR-96-5p, hsa-miR-330-3p, hsa-miR-31-5p, hsa-miR-144-3p, and miR-382-3p or isoforms or variants thereof.

According to the inventive method, the magnitude of difference in the respective circulating miRNA level in a body fluid, specifically in blood serum or plasma when compared to the reference or control level is indicative of osteoporosis or the risk of fractures.

The detection of an increase or decrease of the level of two or more of said miRNAs compared to the level in healthy subjects can be for example used for predicting a risk of osteoporosis or fractures in a subject.

Alternatively, as a read out, the level of miRNAs in a sample to determine the selected miRNAs may be measured and correlated to the risk of said patients, which can be low, medium or high, or else prediction rules established in order to discriminate between the binary outcome stable or progressive disease. For example, the ability of a prediction rule can be assessed by calculating the area under the ROC curve (AUC) using the Sommer's D statistic. The relation between the area under the ROC and Sommer's D is the following:

$$AUC=(1+Sommer's\ D)/2.$$

It is preferred to employ a miRNA marker according to the invention either as single predictor of progression with an AUC value of at least 0.5, preferably at least 0.6, more preferred 0.7, 0.8 or even at least 0.9. Preferred marker combinations reach AUC values of at least 0.6, preferably at least 0.7, 0.8 or even at least 0.9, up to 1.0.

With reference to a healthy subject, the preferred method according to the invention qualifies a significant risk when an increase of the amount of two or more miRNAs according to the invention by at least 50%, preferably at least 60%, more preferred at least 70%, more preferably at least 80%, more preferably at least 100% is determined.

The high risk for osteoporosis or risk of fractures is preferably indicated, if the amount of at least two miRNAs or the combination of more miRNAs as indicated in above lists is increased at least 1.5 times the reference value of subjects not suffering from the disease, preferably being healthy subjects or subjects suffering from a different disease not correlated to increased risk of osteoporosis or bone fracture.

As used herein, the term "microRNA" or "miRNA" or "miR" designates a non-coding RNA molecule having a length of about 17 to 25 nucleotides, specifically having a length of 17, 18, 19, 20, 21, 22, 23, 24 or 25 nucleotides which hybridizes to and regulates the expression of a coding messenger RNA. The term "miRNA molecule" refers to any nucleic acid molecule representing the miRNA, including natural miRNA molecules, i.e. the mature miRNA, pre-miRNA, pri-miRNA.

"miR precursor", "pre-miRNA" or "pre-miR" designates a non-coding RNA having a hairpin structure, which contains a miRNA. A pre-miRNA is the product of cleavage of a primary mi-RNA transcript, or "pri-miR" by the double-stranded RNA-specific ribonuclease known as Drosha. The precursors may be forms of the respective polynucleotides as they occur during maturation of the respective polynucleotides. Specifically, examples of said precursors are listed in tables 3 and 4 specifically they are of SEQ ID Nos 24 to 46, 48 and 72 to 94.

Nucleotide sequences of mature miRNAs and their respective precursors are known in the art and available from the database miRBase at http://www.mirbase.org/index.shtml or from Sanger database at http://microrna.sanger.ac.uk/sequences/ftp.shtml. The nucleotide sequences are also specifically disclosed in tables 3 and 4 including reference to the respective gene bank accession numbers.

Identical polynucleotides as used herein in the context of a polynucleotide to be detected or inhibited in confect of the present invention may have a nucleic acid sequence with an identity of at least 90%, 95%, 97%, 98% or 99% to a polynucleotide comprising or consisting of the nucleotide sequence of any one of SEQ ID Nos. 1 to 23, 47 and 49 to 71.

Furthermore, identical polynucleotides as used herein in the context of a polynucleotide to be detected or inhibited in context of the present invention may have a nucleic acid sequence with an identity of at least 90%, 95%, 97%, 98% or 99% to a polynucleotide comprising or consisting of the nucleotide sequence of any one of SEQ ID Nos. 24 to 46, 48 and 72 to 94 including one, two, three or more nucleotides of the corresponding pre-miRNA sequence at the 5"end and/or the Tend of the respective seed sequence.

All of the specified miRNAs used according to the invention also encompass isoforms and variants thereof.

For the purpose of the invention, the terms "isoforms and variants" (which have also be termed "isomirs") of a reference miRNA include trimming variants (5' trimming variants in which the 5' dicing site is upstream or downstream from the reference miRNA sequence; 3' trimming variants: the 3' dicing site is upstream or downstream from the reference miRNA sequence), or variants having one or more nucleotide modifications (3' nucleotide addition to the 3' end of the reference miRNA; nucleotide substitution by changing nucleotides from the miRNA precursor), or the complementary mature microRNA strand including its isoforms and variants (for example for a given 5' mature microRNA the complementary 3' mature microRNA and vice-versa). With regard to nucleotide modification, the nucleotides relevant for RNA/RNA binding, i.e. the 5'-seed region and nucleotides at the cleavage/anchor side are exempt from modification.

In the following, if not otherwise stated, the term "miRNA" encompasses 3p and 5p strands and also its isoforms and variants.

Specifically, the term "miR-respective_number-3p" as used herein in the specification also encompasses its complementary 5p miRNA and vice versa.

In specific embodiments, the miRNAs of interest are detected using a nucleotide that hybridizes, preferably under stringent conditions, with said miRNA of interest and measuring the hybridization signal.

Circulating microRNAs in cell-free blood such as serum or plasma are a minimal or non-invasive source of biomarkers allowing minimal-invasive detection and therefore a broad applicability in clinics and research repositories. This is especially advantageous for diseases affecting tissues that are not easily accessible for biopsies such as bone. Mitchell and others demonstrated that miRNA measurements in serum and plasma collected from the same healthy individuals from the same blood draw are highly correlated (Chen et al., 2008; Mitchell et al., 2008). However, the choice of anticoagulant (Heparin, EDTA, sodium citrate or Natriumfluorid/potassium oxalat (NaF/KOx)) for plasma sample collection is important, since heparin interferes with enzyme activity in PCR-based assays (Boeckel et al., 2013; Garcia et al., 2002). Similar to heparin, also citrate exhibits an inhibitory effect on qPCR and both are therefore not recommended for miRNA quantitation by qPCR. Unlike heparin, EDTA is removable from the PCR mastermix and is therefore considered the anticoagulant of choice for PCR-based miRNA profiling (Zampetaki & Mayr, 2012). The use of NaF/KOx as anticoagulant resulted in increased miRNA detection rates and may be a suitable alternative if serum or EDTA blood is not at disposition (Kim et al., 2012). The time to centrifugation as well as centrifugation speeds have been shown to critically impact the detection of miRNAs in EDTA plasma samples since it affects the contamination with platelet-derived miRNAs (Cheng et al., 2013). In contrast, miRNA detection in serum was shown to be less sensitive towards pre-processing variations. In view of the state of the art, selecting the appropriate conditions for mi-RNA diagnosis can be done by the skilled person without undue burden.

In a preferred embodiment, the level of the miRNAs of interest is determined by polymerase chain reaction (PCR). PCR methods are well known in the art and widely used, they include quantitative real time PCR, semi-quantitative PCR, multiplex PCR, digital PCR, or any combination thereof. In a particularly preferred embodiment, the levels of miRNAs are determined by quantitative real time PCR (qRT-PCR). Methods of determining the levels of miRNAs using qRT-PCR are known in the art, and are usually preceded by reverse transcription of a miRNA into a cDNA.

In the PCR methods useful in the present invention, the primers are usually based on the mature miRNA molecule, but may include chemical modifications to optimize hybridization behavior.

qRT-PCR methods may determine an absolute level of expression of a miRNA. Alternatively, qRT-PCR methods may determine the relative quantity of a miRNA. The relative quantity of a miRNA may be determined by normalizing the level of the miRNA to the level of one or more internal standard nucleic acid sequences. In general, such internal standard nucleic acid sequences should have a constant level in the analyzed blood or serum sample. For instance, internal standard nucleic acid sequences may be constitutively transcribed RNA nucleic acid sequences such as mRNAs like glyceraldehyde-3-phosphate-dehydrogenase (GAPDH), beta-actin (ACTB), or non-coding RNAs such as 5S and 18S ribosomal RNA, RNU48, RNU44, and RNU6. In addition, miRNAs that have constant and high levels in serum or plasma, such as miR-23a-3p, miR-23b-3p, miR- 15-5p or miR-16-5p can be used as references for relative quantification. In addition, synthetic RNA sequences added in an equimolar amount during RNA isolation or cDNA synthesis can be used as references for relative quantification of specific miRNAs.

An overview of real time PCR quantification methods useful in the present invention is given by Schmittgen et al., 2008, Methods. January; 44(1): 31-38. Primers for detection of miRNAs are commercially available, e.g. as microRNA LNA™ PCR primer sets from Exiqon.

Since miRNAs are relatively short molecules, it may be useful, as suggested, e.g. in WO2011/14476, to lengthen them by adding adenosine monomers to the strand (a technique known as polyadenylation) before reverse transcription and amplification. Briefly, the RNA may be extracted from the sample by a suitable reagent (e.g. Trizol reagent), polyadenylated in the presence of ATP and poly(A) polymerase, reverse transcribed into cDNA using a poly(T) adapter and 5' RACE sequence, and amplified using a forward primer derived from the 3' end of the miRNA and a reverse RACE primer. Improvements of this technique include designing the RACE primer with a nucleotide at its 3' end (constituting an A, C, or G, but not a T, so to exclude priming anywhere on the polyA sequence and enforce priming on the miRNA sequence) or RACE primers which are anchored at the 3' cDNA end of a specific microRNA using 2, 3, 4, or more nucleotides with or without chemical modification.

The detection of a miRNA may also be achieved by other methods known in the art, e.g. those described in WO2011/14476, like by the deep sequencing method, bead-based quantification, e.g. Illumina bead-arrays, hydrogel-particle based quantification, e.g. Firefly™, by microarray technology, e.g. the Ncode™ human miRNA array available from Invitrogen, chip arrays available from Affymetrix, Agilent, or microarrays which employ LNA-backbone capture probes (miRCURY LNA™ arrays), e.g., from Exiqon.

The difference in miRNA levels can also be determined using multiplex chemiluminescence-based nucleic acid assays such as Panomics, or reporter plasmid assays ("biosensors") containing reporter proteins with microRNA-complementary regulatory sites, or other hybridization-based techniques known in the art.

The use of miRNAs in a method of the invention is useful for diagnosing bone disorders associated with low bone mineral density (due to aberrant bone metabolism which is reflected in secreted miRNAs) like osteoporosis and, in particular, for assessing the risk of osteoporotic fractures.

The present invention specifically provides a set of miRNAs that represent a diagnostic signature applicable both over a broad range of bone disease stages and age groups. In particular, detection of miRNAs, a), which are differentially regulated in the blood or serum of younger patients than those recruited by Seeliger et al., supra, b), which are differentially regulated in patients with non-recent fractures, and/or c), which are differentially regulated in type-2 diabetes patients with non-recent fractures, provides a diagnostic and predictive tool that has a higher significance for early diagnosis, long-term prognosis, and screening of patients with high risk of fractures.

Biomarkers with prognostic value for disease progression are of utmost importance to minimize the occurrence of severe osteoporotic fractures. Currently, a high incidence in osteoporotic fractures can be attributed to unspecific diagnostic methods that are largely based on bone imaging and routine clinical parameters and overt characteristics such as sex, age, life style and family history and FRAX™ scores. Evaluation of these parameters are however, not directly relevant for bone metabolism and osteoblast/osteoclast activity. Therefore high variation in the individual fracture-risk persists, albeit general guidelines that involve FRAX™ and BMD. Early diagnosis using microRNAs relies on a read out of bone metabolism and thus the pathophysiology of the diseases itself. This analysis is therefore more specific to the individual patient.

According to another aspect, the invention relates to therapeutical compositions for the treatment of bone fractures and bone disorders like osteoporosis, or in the context of type-2 diabetes, in particular for the prevention or healing of fractures.

Specifically, a composition can comprise at least one, specifically at least two isolated or synthetic human miRNAs from miRNAs hsa-miR-188-3p, hsa-miR-382-3p, hsa-miR-127-3p, hsa-miR-144-3p, hsa-miR-155-5p, hsa-miR-181a-3p, hsa-miR-1908, hsa-miR-190a, hsa-miR-199b-5p, hsa-miR-203a, hsa-miR-214-3p, hsa-miR-29b-3p, hsa-miR-330-3p, hsa-miR-335-5p, hsa-miR-31-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, sa-let-7b-5p, hsa-miR181d, hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p, hsa-miR-96-5p and hsa-miR382-3p or isoforms or variants thereof.

According to a specific embodiment, the composition comprises at least one of specifically at least two isolated or synthetic human miRNAs from hsa-miR-188, hsa-miR-382 and hsa-miR-550a. These miRNAs or their inhibitors/antagonists respectively, may be used in combination with the miRNAs listed in the paragraph above or as single components or in any combination thereof.

Whether the miRNA itself or an inhibitor/antagonist thereof is incorporated as the active ingredient in the therapeutical composition not only depends on whether such miRNA is up- or down-regulated in a patient at risk of an osteoporotic fracture, but on its specific function in osteogenic differentiation or in osteoclastogenic activation. By way of example, if a miRNA, which functions as an inhibitor of osteogenic differentiation, is found upregulated in osteoporosis, as shown in tables 1 and 2 or specifically, as known for miR 31-5p, or if it functions as a promoter of osteoclastogenesis like miR-148a-5p, an inhibitor/antagonist of such miRNA will be the active ingredient in the composition of the invention.

In the following, if not otherwise stated, the term "miRNA therapeutic" is used for both the miRNA itself and the respective miRNA inhibitor/antagonist.

A miRNA therapeutic is generally based on the sequence of the targeted mature miRNA. Therapeutics for miRNA replacement therapies need to share most of the sequence of the mature miRNA which is substituted. Exact sequence homology is required in the 5' seed region of the miRNA. Therapeutics designed to specifically inhibit miRNA function (anti-microRNA oligonucleotides, AMO) need to be complementary to the targeted sequence so that a stable hybridization and hence sequestration of the miRNA is achieved. AMOs may contain chemical modifications which cause stable RNA duplex formation, such as a phosphorothioate backbone, or LNA and 2'OMe modifications of the sugar residues, respectively.

Whether a miRNA that is up- or downregulated in serum/plasma of subjects with bone disorders, may be causally related to the disease due to its function in bone formation, can be determined by assessing the effect of these miRNAs on osteogenic differentiation: synthetic microRNA transfection in mesenchymal stem cells is performed prior to the initiation of osteogenic differentiation. Using assays that quantitate the early osteogenic marker alkaline phosphatase (ALP), e.g. by qPCR, western blot, or enzymatically, or assays determining calcium deposition, e.g. by Alizarin staining, as described by Deng et al. (Deng et al., 2014), conclusions about the importance of a miRNA for bone formation can be drawn.

Alternatively, a miRNA therapeutic may be routinely tested for usefulness in the present invention by transfecting MSCs or, as a model for MSCs, adipose tissue-derived stem cells (ASCs), with mammalian vector constructs containing the DNA sequence encoding the miRNA therapeutic and determining its effect on osteogenic differentiation as described above.

MSCs and ASCs may be obtained by known methods, e.g. as described by Wolbank et al., 2007 (Tissue Eng 13, 1173-1183) and Wolbank et al., 2009 (Tissue Eng Part A 15, 1843-1854).

A miRNA that is confirmed to be involved in bone regeneration and thus to promote bone healing, is useful as the active ingredient in a pharmaceutical composition of the invention.

Whether a miRNA that is up- or downregulated in serum/plasma of subjects with bone disorders, may be causally related to the disease due to its function in bone resorption, can be determined by assessing the effect of these miRNAs on osteoclast formation: synthetic microRNA transfection in CD14+ peripheral blood mononuclear cells is performed prior to the initiation of osteoclast formation through RANKL and M-CSF. Using assays that quantitate osteoclast markers such as tartrate-resistant acid phosphatase (TRAP) activity, Calcitonin receptor and RANK expression, conclusions about the importance of a miRNA for bone resorption can be drawn. A miRNA can be obtained from a miR precursor using intact cells or cell lysates or it can be produced in vitro using isolated processing enzymes, such as isolated Drosha/Dgcr8 and Dicer. A miRNA may also be produced by chemical synthesis, without having been processed from a miR precursor.

Antagonists/inhibitors of miRNAs are well known in the art and customized miRNA inhibitors are commercially available. For example, antagonists/inhibitors of in context of the present invention may be nucleic acid molecules such as antagomiRs (Kriitzfeldt, Nature (2005), 438: 685-689) or any other T-O-methyl-RNA oligonucleotide having phosphorothioates bonds and a cholesterol tail, miRCURY LNA™ microRNA inhibitors (Exiqon), in vivo LNA™ miRNA inhibitors (Exiqon), tiny LNAs (Obad, Nat Genet (2011), 43(4): 371-378), miR-decoys or miR-sponges (Ebert, Nat Methods (2007), 4: 721-726; Bond, Nat Med (2008), 14: 1271-1277) or the like. An antagonist/inhibitor might also be or derived from miRNA degrading enzymes as described in Chatterjee, Nature (2009), 461: 546-9, hammerhead ribozymes as described in Tedeschi, Drug Discov Today (2009), 14: 776-783, or antogomirzymes as described in Jadhav, Angew Chem Int Ed Engl (2009), 48(14: 2557-2560. In context of the present invention, the antagmiRs, miCURY LNA™ microRNA inhibitors, in vivo LNA™ miR inhibitors, tiny LNAs, miR decoys or miR sponges.

In a further embodiment, the active ingredient of the pharmaceutical composition is selected according to the principles of so-called "personalized medicine", i.e. correlated with the results of the diagnostic method of the invention, which would, in this case, be a so-called "companion" diagnostic. This means that the decision over therapeutic administration of a miRNA with the aim to either substitute or inhibit a specific miRNA, is closely linked to an accompanying diagnostic procedure where the level of the specific miRNA is analyzed in an individual.

Osteoclast-specific promoters such as Calcitonin receptor (CalcR), RANK (receptor activator of NFkB), colony stimulating factor 1 receptor (c-Fms), and Cathepsin K (CathK) may be used.

In embodiments of local administration, e.g. for accelerating bone healing after a fracture, the nucleic acid molecule encoding the miRNA therapeutic may be delivered to the site of interest by means of viral or nonviral vectors or as naked DNA or RNA. As reviewed by Pelled et al., 2010 (Tissue Engineering: Part B, Volume 16, No. 1, 13-20), localization of the therapeutic molecule within the fracture site may be assured either by physical placement at the target site or by gene release from a three dimensional biomaterial implanted at or near the defect area, including biological glues such as polymers of fibrinogen and thrombin. Useful physical placement methods include direct injection of the miRNA, or lipid-microRNA complexes formed from agents such as Polyethylenimine (PEI) therapeutic into the fracture site. Preferably, in order for the nucleic acid molecule to penetrate cells in situ, it is delivered in complexed state using such as liposomes or PEI. Alternatively, the miRNA could be transcribed by a virus. Preferably, an adenoviral vector is used, as described for expressing bone morphogenetic protein (BMP) by Egermann et al., 2006 (Hum Gene Ther. May; 17 (5):507-17).

Alternatively to using a vector, in vivo electroporation or sonoporation may be used to deliver the therapeutic locally. Using these methods, the miRNA or the miRNA-encoding DNA molecule is directly injected into a fracture and an electric pulse or ultrasonic wave is applied to the site either trans- or percutaneously. Said miRNAs or antagonists/inhibitors thereof may also be part of fibrin sealants, specifically used for bone repair and regeneration.

In a further embodiment, mesenchymal stem cells derived from any source, including but not limited to bone marrow, adipose tissue, umbilical tissue, urine, or placenta, genetically engineered to overexpress or suppress the therapeutic miRNA may be implanted at the defect site (Marie, 2011, Osteoporos Int 22:2023-2026, Deng et al., supra).

In an alternative embodiment, localizing the miRNA therapeutic at the site of interest, e.g. the fracture site, e.g. by transgene expression, is achieved by first binding the miRNA therapeutic DNA or RNA to a delivery system (e.g. by adsorption, entrapment or immobilization, or by covalent binding; Luginbuehl et al., 2004, Eur J Pharm Biopharm 58:197-208) and then implanting the gene-activated matrix (GAM) into the defect site, e.g. as described by Fang et al., 1996 (Proc Natl Acad Sci USA 93, 5753).

Useful matrices (GAMs, "gene-activated matrices") have been described in the context with matrices for the delivery of the miRNA. Also when the therapeutically active miRNA or an inhibitor/antagonist thereof is administered locally, either as such or incorporated in a matrix, it may advantageously be linked to a bone-targeting molecule. This may be accomplished by linking the delivery vehicle, e.g. a liposome, which is used to complex the miRNA therapeutic, with the bone-targeting molecule. In the case that a nucleic acid molecule is to be administered locally, incorporation of the bone-targeting molecule is achieved by linking it to the surface of the delivery vehicle. The same applies for a CPP.

Any miRNA therapeutic of the invention, either containing the miRNA molecule or the nucleic acid molecule encoding it, or an antisense inhibitor, may be combined with one or more other agents e.g. teriparatide, denosumab, blosozumab, romosozumab, bisphosphonates such as alendronate, zolendronate, or one or more bone growth factors or the respective encoding nucleic acid molecules, e.g. a BMP like BMP-2 and/or BMP-7, or RNAs, like e.g. RNAs antagonizing miR-31.

The present invention also encompasses following items:

1. An in vitro method of diagnosing osteoporosis or determining the risk of osteoporotic fractures or monitoring of treatment in a subject, comprising the steps of:
   a) providing a sample from said subject,
   b) measuring the level of two or more miRNAs selected from any of miRNAs consisting of hsa-miR-144-3p, hsa-miR-188-3p, hsa-miR-382-3p, hsa-miR-127-3p, hsa-miR-155-5p, hsa-miR-181a-3p, hsa-miR-1908, hsa-miR-190a, hsa-miR-199b-5p hsa-miR-203a, hsa-miR-214-3p, hsa-miR-29b-3p, hsa-miR-330-3p, hsa-miR-335-5p, hsa-miR-31-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and hsa-miR-181d or isoforms or variants thereof, and
   c) comparing the level of said miRNAs to a reference level,
   wherein the magnitude of difference in said level when compared to the reference level is indicative of osteoporosis or the risk of fractures.

2. The method according to item 1, wherein the level of all of hsa-miR-203a, hsa-miR-330-3p, hsa-miR-188-3p, hsa-miR-550a-5p, hsa-miR-335-5p, hsa-miR-29b-3p, hsa-miR-214-3p and hsa-miR-31-5p is measured.

3. The method according to item 1, wherein at least one miRNA selected from the group consisting of hsa-miR-188-3p, hsa-miR-382-3p, hsa-miR-203a, hsa-miR-181a-3p, hsa-miR-330-3p and hsa-miR-369-3p and at least one miRNA selected from the group consisting of hsa-miR-127-3p, hsa-miR-155-5p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, and hsa-miR-181d are measured.

4. The method according to item 1 or 3, wherein hsa-miR-188-3p is measured in combination with at least one miRNA selected from the group consisting of hsa-miR-127-3p, hsa-miR-155-5p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

5. The method according to item 1 or 3, wherein hsa-miR-382-3p is measured in combination with at least one miRNA selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

6. The method according to item 1 or 3, wherein hsa-miR-181a-3p is measured in combination with at least one miRNA selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

7. The method according to item 1 or 3, wherein hsa-miR-330-3p is measured in combination with at least one miRNA selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

8. The method according to item 1 or 3, wherein hsa-miR-369-3p is measured in combination with at least one miRNA selected from the group consisting of hsa-miR-127-3p, hsa-miR-155-5p, hsa-miR-188-3p, hsa-miR-1908, hsa-miR-190a, hsa-miR-199b-5p, hsa-miR-144-3p, hsa-miR-335-5p, hsa-miR-31-5p, hsa-miR-214-3p, hsa-miR-29b-4p, hsa-let-7b-5p, hsa-miR-203a, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

9. The method according to item 1 or 3, wherein hsa-miR-203a is measured in combination with at least one miRNA selected from the group consisting of hsa-miR-127-3p, hsa-miR-155-5p, hsa-miR-188-3p, hsa-miR-1908, hsa-miR-190a, hsa-miR-335-5p, hsa-miR-31-5p, hsa-miR-214-3p, hsa-miR-29b-4p, hsa-let-7b-5p, hsa-miR-342-5p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942 and hsa-miR-181d.

10. The method according to any one of items 1 to 9, wherein the subject is a post.menopausal female or an osteoporosis or osteopenia patient, suffering from or being at risk of developing bone fractures.

11. The method according to any one of items 1 to 10, wherein the level of at least 3, preferably at least 4, preferably at least 5, specifically up to 30 miRNAs is measured.

12. An in vitro method of diagnosing osteoporosis or determining the risk of osteoporotic fractures or monitoring of treatment in a subject, comprising the steps of:
   a) providing a sample from said subject,
   b) measuring the level of two or more miRNAs selected from any of miRNAs consisting of hsa-miR-32-3p, hsa-let-7b-5p, hsa-let-7g-5p, hsa-let-7i-5p, hsa-miR-141-3p, hsa-miR-143-5p, hsa-miR-16-2-3p, hsa-miR-181c-3p, hsa-miR-181c-5p, hsa-miR-191-5p, hsa-miR-19b-1-5p, hsa-miR-203a, hsa-miR-21-3p, hsa-miR-323a-3p, hsa-miR-375, hsa-miR-486-5p, hsa-miR-500a-5p, hsa-miR-550a-5p, hsa-miR-7-5p, hsa-miR-92a-3p, hsa-miR-942, hsa-miR-96-5p, hsa-miR-330-3p, hsa-miR-31-5p, hsa-miR-144-3p, and hsa-miR-382-3p, and c) comparing the level of said miRNAs to a reference level, wherein the magnitude of difference in said level when compared to the reference level is indicative of osteoporosis or the risk of fractures.

13. The method according to item 12, wherein at least one miRNA selected from the group consisting of hsa-miR-32-3p, hsa-miR-181c-3p, hsa-miR-323a-3p, hsa-miR-550a-5p and hsa-miR-96-5p and at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p are measured.

14. The method according to item 12 or 13, wherein hsa-miR-32-3p is measured in combination with at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

15. The method according to item 12 or 13, wherein hsa-miR-181c-3p is measured in combination with at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

16. The method according to item 12 or 13, wherein hsa-miR-323a-3p is measured in combination with at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

17. The method according to item 12 or 13, wherein hsa-miR-550a-5p is measured in combination with at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR382-3p.

18. The method according to item 12 or 13, wherein hsa-miR-96-5p is measured in combination with at least one miRNA selected from the group consisting of hsa-let-7b-5p, hsa-let-7g-5p, hsa-let-7i-5p, hsa-miR-141-3p, hsa-miR-143-5p, hsa-miR-16-2-3p, hsa-miR-181c-5p, hsa-miR-191-5p, hsa-miR-19b-1-5p, hsa-miR-203a, hsa-miR-21-3p, hsa-miR-375, hsa-miR-486-5p, hsa-miR-500a-5p, hsa-miR-7-5p, hsa-miR-92a-3p, hsa-miR-942, hsa-miR-330-3p, hsa-miR-31-5p, hsa-miR-144-3p and hsa-miR-382-3p.

19. The method according to any one of items 12 to 18, wherein the subject is a patient being at risk of or suffering from type 2 diabetes mellitus.

20. The method according to any one of items 12 to 19, wherein the sample is a blood sample.

21. The method according to any one of items 12 to 20, wherein the level of at least 3, preferably at least 4, preferably at least 5, specifically up to 26 miRNAs is measured.

22. The method according to any one of items 1 to 21, wherein the level of said miRNAs is compared with the average level of corresponding miRNAs in healthy subjects, wherein a difference by more than one standard deviations is indicative of osteoporosis with increased risk of future fractures.

23. The method according to items 1 to 22, wherein the level of all miRNAs is measured.

24. The method according to items 1 to 23, wherein one or more further miRNAs are detected, wherein said miRNAs are a) differentially regulated in osteoporotic individuals as compared to healthy individuals and are b) involved in osteogenic differentiation and/or in osteoclastogenic activation.

25. Use of a method according to any one of claims 1 to 24 for monitoring a subject, specifically for the prognosis of bone fraction.

26. Use of a method according to any one of items 1 to 24 for monitoring a subject, specifically for measuring the response of a subject to anti-osteoporotic treatments.

27. The method according to any one of items 1 to 25, wherein the difference in miRNA levels is determined by quantitative or digital PCR, sequencing, microarray, Luminex nucleic acid assays, or other hybridization-based techniques.

28. Composition for use in treating or preventing osteoporosis or fractures comprising a) at least two synthetic human miRNAs from miRNAs of items 1 and/or 12 and/or b) an antagonist/inhibitor of at least two of miRNAs of items 1 and/or 12 that i. decreases the level of said miRNAs; and/or ii. inhibits or down-regulates expression of the sequences coding for said miRNAs or degrades or cleaves said miRNAs.

29. Use of a composition comprising at least one, specifically at least two synthetic human miRNAs of items 1 and/or 12 and/or an antagonist/inhibitor of at least two of miRNAs of claims 1 and/or 12 that decreases the level of said miRNAs; and/or inhibits or down-regulates expression of the sequences coding for said miRNAs or degrades or cleaves said miRNAs for preparing a medicament.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: Circulating microRNAs in Response to Recent Femoral-Neck Fractures

Study Design

For the analysis of miRNAs in recent fractures the focus was put on patients younger than those selected by Seeliger et al., 2014, supra, since diagnosis preferentially occurs early during disease development, i.e. at younger age.

Ethical approval was granted by the upper Austrian ethics committee for the collection of serum samples from 14 subjects by centrifugation at room temperature at 2000×g for 15 minutes after incubation at room temperature for 30 minutes. Subjects were classified into two groups (n=7) based on prior occurrence of osteoporotic femoral fractures (FIG. 1a). Of the analyzed characteristics such as age, body mass index (BMI), sampling interval after surgery, BMD T-Score, Vitamin D and PTH, only BMI showed significant differences.

RNA Isolation

Serum samples were frozen at −80° C. for long term storage. Upon RNA isolation, serum was thawed at 37° C., centrifuged at 12.000×g for 5 minutes to remove cellular debris and 200 µl serum were homogenized in 750 µl Qiazol containing 35 fmol synthetic cel-miR-39-3p spike-in control. RNA isolation was performed using chloroform and the miRNeasy isolation kit (Qiagen, Germany) for RNA precipitation and purification with the following deviations from the standard protocol: 200 µl plasma were homogenized in 750 µl Qiazol. Exactly 500 µl aqueous phase were taken, 1 µl Glycogen (Ambion, Tex.) was added to a final concentration of 50 µg/ml and precipitated with 750 µl 100% Ethanol. Columns were washed three times with RPE buffer and plasma-RNA was eluted once in 30 µl nuclease-free water and stored at −80° C. Quantitation of cel-miR-39-3p was performed in quadruplicates on a Qiagen Rotorgene using the respective Taqman microRNA Assay Kit and Mastermix (Applied Biosystems).

qPCR Analysis

Screening of miRNA expression was performed by Exiqon Inc. in Denmark using 384-well serum/plasma focus panels, which cover 175 distinct human miRNAs that have been repeatedly found to circulate in serum or plasma. First, 4 µl of isolated RNA were reverse transcribed in 20 µl reactions using the miRCURY LNA Universal RT reaction kit. UniSp3 and UniSp6 are synthetic controls that were added at this step and subsequently analyzed to detect presence of enzyme inhibitors. RT-reactions were diluted 50-fold prior to qPCR analysis and each miRNA was assayed once per sample in a 10 µl reaction using the Roche LC 480 Real-Time PCR System (Roche, Germany).

Data Analysis

Melting curve analysis was performed and miRNA PCR reactions with more than one peak were excluded from the analysis. Amplification efficiencies were calculated using algorithms similar to the linreg software package. Efficiencies ranged between 1.8 and 2.1 for most miRNAs. Individual reactions that gave efficiencies <1.6 were excluded from the dataset. Background levels for each miRNA were generated by assaying a "no template" cDNA synthesis control on a full serum/plasma focus panel plate. The majority of miRNA assays did not yield any signal and background Cp was set to 42. We required every miRNA assay to exhibit signals >5 Cps lower than the background value to be included in the analysis. Normalization of Cp-values was performed based on the average Cp of the miRNA assays detected across all 14 samples (124 assays). Normfinder software was used to confirm that the stability of the average Cp was higher than the stability of any individual miRNA assay in the data set. The following equation was used for normalization: normalized Cp (dCp)=average Cp (124 assays)−assay Cp (sample). This results in a delta Cp (dCp) value, which is a relative $\log_2$-transformed measure for expression where higher values indicate a higher concentration and lower dCp values indicate lower concentration in plasma.

Non-parametric t-statistics were calculated using the Mann-Whitney U test and fold changes between the average expression values for each group were calculated. In total, fifteen miRNAs showed a high difference (Fold Change>1.5) between recent fracture and control samples.

Example 2: Circulating microRNAs in Patients with Prevalent or Incident Non-Recent Osteoporotic Fractures with and without Type-2 Diabetes Study Design for Prevalent Osteoporotic Fractures Serum samples of 74 postmenopausal women (17 controls without fracture history (Co), 19 controls with history of fragility fractures (Fx), 19 type 2 diabetic women without fractures (DM) and 19 type 2 diabetic women with history of fragility fractures (DMFx)) have been collected during the study conduct. To be included in the study, all women had to be postmenopausal, aged 50-75 with a body mass index ranging from 18 to 37 kg/m2. All subjects were required to be mobile and able to move without walkers. For subjects enrolled in the diabetic group, a minimum of 3 years history of treatment for type 2 diabetes by oral medications and/or insulin was required. Caucasian, Asian and African-American women were included. Subjects with fractures were only included if the fractures were caused by a low energy trauma such as falls from standing height or less and if they were sustained after menopause. Patients with pathologic fractures of other origin such as local tumors, tumour-like lesions or focal demineralizations as visualized on radiographs were excluded from the study.

Exclusion criteria comprised all medical conditions that could affect bone metabolism such as severe neuropathic disease, juvenile or premenopausal idiopathic osteoporosis, hyperthyroidism, hyperparathyroidsm, a recent history of longer (>3 months) periods of immobilization, chronic drug use, alcoholism, chronic gastrointestinal disease, significant chronic renal impairment (CKD stages IV and V), significant chronic hepatic impairment, unstable cardiovascular disease or uncontrolled hypertension. In addition any chronic treatment over the last six months with adrenal or anabolic steroids, estrogens, antacids, anticonvulsants, anticoagulants, pharmacological doses of Vitamin A, fluorides, bisphosphonates, calcitonin, tamoxifen or parathyroid hormone (PTH) was considered a criterion for exclusion. Due to their proven impact on bone mass and bone structure subjects who were on anti-diabetic agents such as rosiglitazone or pioglitazone were also excluded from the study.

The study protocol was approved by the UCSF Committee of Human Research (CHR) and all patients gave written informed consent before participation. Blood specimens were collected between 8 and 11 am after 12 hours of overnight fasting according to the laboratory's handling instructions. For serum samples, blood was allowed to clot in an upright position for 40 minutes and then centrifuged at 2500 rpm for 15 min within one hour of collection. None of the samples showed signs of hemolysis on visual inspection. Serum was subsequently transferred to 1.5 ml plastic screw-cap vials and stored at −80° C. until further analysis.

Study Design for Incident Osteoporotic Fractures

A prospective nested case-control study-design with 443 postmenopausal women over age 66 from the AGES-Reykjavik cohort was generated. The aim of this study was the identification of circulating microRNAs for the prediction of first osteoporotic fractures (incident fracture) or additional osteoporotic fractures. For that purpose blood samples are analyzed at baseline for serum microRNA levels and correlated with the patient outcome after the first follow up at 5.4 years. In total the study design included 4 groups: a control group comprising 100 healthy individuals without prevalent fractures and who did not sustain fractures during the 5.4 year follow-up, a fracture group comprising 172 patients of which 100 had sustained a first incident fracture during the follow up and 72 patients who already had one or more prevalent fractures before sustaining an additional fracture during the follow-up period, a control diabetic group comprising 100 individuals that had been diagnosed with type-2 diabetes but did not have prevalent or sustain incident fractures during the follow up, and a diabetic fracture group consisting of 71 patients of which 35 had sustained a first incident fracture within the 5.4 year follow-up and 36 patients who had prevalent fracture at baseline and one or more additional incident fractures during the follow up period.

In fracture groups, patients with high energy trauma and stressfractures were excluded. Prevalent fractures that had happened 18 months before study visit or less were excluded. Only subjects were included that exhibited kidney functions above 30 ml/min (eGFR), a BMI of >20 kg/m2, no history of longstanding or recent immobilization, no current intake of bone affecting medications and no self-reported or medical record based evidence of kidney disease, liver disease, chronic gastrointestinal disease, hyperparathyroidism, ovariectomy, chornic alcoholism, or idiopathic osteoporosis.

RNA Isolation

For RNA isolation, 200 µl serum were thawed at 37° C., centrifuged at 12,000×g for 5 minutes and homogenized in 1000 µl Qiazol containing synthetic RNA spike-in controls (Exiqon, Denmark) at three different concentrations to monitor the efficiency of small RNA purification. RNA isolation was performed using chloroform extraction and the miRNeasy isolation kit (Qiagen, Germany) for RNA precipitation and purification with the following deviations from the standard protocol: exactly 650 µl aqueous phase after extraction were taken, and 1 µl Glycogen (Ambion, Tex., USA) was added to a final concentration of 50 µg/ml and precipitated with 975 µl 100% Ethanol. Columns were washed three times with RPE buffer and RNA was eluted once in 30 µl nuclease-free water and stored at −80° C.

qPCR Analysis

The qPCR-based high-throughput quantification of miRNAs was performed in 384-well plate using reagents by Exiqon. First, 10 µl of isolated RNA were reverse transcribed in 50 µl reactions using the Universal cDNA Synthesis Kit II. UniSp6 and cel-miR-39-3p were added during this step to monitor the presence of enzyme inhibitors. cDNA samples ere diluted 100-fold prior to qPCR analysis in pre-coated Pick&Mix 384-well plates with custom design. Using an epMotion P5073 liquid handling robot (Eppendorf, Germany), 10 µl of qPCR mix were distributed to each well of the qPCR palte. Each miRNA is assayed once per sample in a 10 µl reaction using the Roche LC 480 Real-Time PCR System (Roche, Germany).

Data Analysis

Melting curve analysis was performed and miRNA PCR reactions with more than one peak were excluded from the analysis. Amplification efficiencies were calculated using algorithms similar to the linreg software package. Efficiencies ranged between 1.8 and 2.1 for most miRNAs. Individual reactions that gave efficiencies <1.6 were excluded from the dataset. Background levels for each miRNA were generated by assaying a "no template" cDNA synthesis control on a full serum/plasma focus panel plate. The majority of miRNA assays did not yield any signal and background Cp was set to 42. The expression data was prefiltered according to the following criteria: i) features with more than 50% empty-values were excluded; ii) features with a p-value of <0.05 in a single-factor ANOVA analysis between any of the 4 groups were selected; iii) features with chi-square test p-value <0.1, indicating unequal distribution of negative signals between fracture and non-fracture samples or diabetes and non-diabetes samples, were selected. The aim of this step was to allow only features with trend towards regulation in any of the 4 groups to be further processed. The Ct-values of the remaining 146 features were corrected for the global mean of spike-in control levels and finally, empty values were replaced by imputed values, based on the assumption of normal distributed values.

Gene-wise linear models were fitted incorporating class information, e.g. fracture vs. no fracture, or diabetic fracture vs diabetic control, by generalized least squares. The p-values of the test whether the class coefficient is different from 0 were adjusted for multiple testing using the method proposed by Benjamini and Hochberg. The limma package from the Bioconductor repository was used. Every single model was evaluated by means of the AUC values and misclassification rates of a 5-fold cross validation using the support vector machine as a base classifier. The smallest model size that obtained an AUC value close to the maximum AUC value was chosen.

The entire procedure was repeated with simulated data that incorporated the same dimensionality and correlation structure as the original data but exhibited no difference in means between classes. The maximal resulting AUC value was used as a reference point characterized by zero reproducibility. All models selected using the two step method described above clearly yielded superior results as compared to the reference point.

Results

For the classification of non-diabetic fracture patients, a combination of 4 microRNAs (Table 5) was identified that yielded an AUC value of 1.0. This combination consisted of miR-188-3p, miR-550a-5p, miR-582-3p, and miR-382-3p. In addition, several other combinations of four microRNAs performed similar well (Table 5, FIG. 3B).

For the classification of diabetic fracture patients, a combination of 4 microRNAs (Table 6) was identified that yielded an AUC value of 0.961. This combination consisted of miR-550a-5p, miR-96-5p, miR-32-3p, and miR-375. In addition, several other combinations of four microRNAs performed similar well (Table 6, FIG. 3A).

Example 3: Analysis of microRNA Function in the Context of Osteogenic Differentiation Human adipose-derived stem cells (ASCs) were obtained from subcutaneous adipose tissue, which was derived from outpatient tumescence liposuction under local anesthesia with patient consent. ASCs were isolated as described before (Wolbank et al., 2007a; Wolbank et al., 2007b; Wolbank et al., 2009a) and cultured in DMEM-low glucose/HAM's F-12 supplemented with 4 mM L-glutamine, 10% fetal calf serum (FCS, PAA) and 1 ng/mL recombinant human basic fibroblast growth factor (rhFGF, R&D Systems) at 37° C., 5% CO2 and 95% air humidity. Cells were passaged once or twice a week at a split ratio of 1:2 according to the growth rate.

Induction of Osteogenic Differentiation in ASCs

All differentiation protocols were carried out in 24 well cell culture plates. For osteogenic differentiation ASCs were seeded at a density of $2 \times 10^3$ cell per well. 72 hours after seeding cells were incubated with osteogenic differentiation medium (DMEM-low glucose, 10% FCS, 4 mM L-glutamine, 10 nM dexamethasone, 150 µM ascorbate-2-phosphat, 10 mM β-glycerolphosphate and 10 nM vitamine-D3) up to 4 weeks.

Alizarin Red S Staining

For Alizarin staining of calcified structures, cells were fixed for 1 hour in 70% ethanol at −20° C. After brief rinsing, cells were stained for 20 minutes with 40 mM Alizarin Red solution (Sigma) and washed with PBS. For quantification Alizarin was extracted for 30 minutes using 200 μl 0.1 M HCL/0.5% SDS solution. The extracted dye was measured at 425 nm.

Transfections

ASCs were transfected using siPORT™ NeoFX™ transfection reagent (Applied Biosystems). Cells were transfected with 10 nM precursor microRNA, or scrambled miRNA control #2 (Ambion) according to the manufacturer's protocol. Three days after transfection, differentiation was started as described above.

Results

Transfections were performed for miR-188-3p, miR-382-3p, and miR-550a-5p in biological triplicates (i.e. three different human donors for adipose tissue derived mesenchymal stem cells). Overexpression was successful and was significant for all three miRNAs (FIG. 5A). Proliferation was analyzed one week after the transfection. A slightly positive effect could be detected for miR-188-3p, while miR-382-3p and miR-550a-5p did not affect cell proliferation (FIG. 5B). All three microRNAs significantly impacted osteogenic differentiation (Figure KID) as indicated by the induction of alkaline phosphatase activity and calcium deposition through miR-188-3p and miR-382-3p, and the inhibition of alkaline phosphatase and Calcium deposition by miR-550a-5p.

Example 4: Circulating microRNA Signatures in Patients with Idiopathic and Postmenopausal Osteoporosis and Fragility Fractures Study Design A case-control study with cross-sectional design was performed. A total of 36 adult female and male patients with idiopathic osteoporosis (mean age 46.6+/−13.0 years) were included in the study: 10 premenopausal women (mean age 39.0+/−8.6), 10 postmenopausal women (mean age 59.0+/−11.4) and 16 men (mean age 43.7+/−11.1) with low-traumatic fractures. Vertebral fractures and peripheral low-traumatic fractures were observed in 61% and 50% of the patients, respectively. Twenty-two percent of patients sustained both vertebral and peripheral fractures. In total, 152 fractures were recorded (mean number of fractures 4.2). Thirty-one percent of patients had received either anticatabolic (bisphosphonates, denosumab, n=13) or osteoanabolic (teriparatide, n=2) drugs within the last year. miRNAs were compared to 39 subjects without low-traumatic fractures (mean age 46.6+/−9.4 years): 12 premenopausal women (mean age 42.5+/−6.8), 11 post-menopausal women (mean age 54.3+/−7.4) and 16 men (mean age 44.4+/−9.6). Patients with osteoporosis and healthy controls had similar age, height, weight and therefore BMI.

microRNA qPCR Analysis

In total 187 miRNAs and 5 controls were analyzed in the entire cohort of 75 individuals over a period of 4 weeks. All miRNAs were selected based on the results from previous studies (Example 1 and 2). The miRNeasy Mini Kit (Qiagen, Germany) was used to perform RNA-Isolation. Frozen serum samples at −80° C. were thawed on ice and centrifuged at 12,000g for 5 minutes. After centrifugation, 200 μl serum were mixed by vortexing with 1000 μl Qiazol, to which a mix of 3 synthetic spike-in controls (UniSp 2,4,5) had been added. After incubation at room temperature for 10 minutes, 200 μl chloroform were added to the homogenized sample, vigorously vortexed and incubated for 3 minutes. After centrifugation at 12 000 g for 15 minutes at 4° C., exactly 650 μl of upper aqueous phase were taken and glycogen (Ambion, USA) was added to a final concentration of 50 g/ml. Samples were then transferred to columns and further processed using the QIA-Cube liquid handling robot. RNA was precipated with 750 μl Ethanol, triple washed with RPE-buffer, followed by RNA-elution in 30 μl nuclease free water and storage at −80° C.

For qPCR analysis, 4 μl of isolated RNA were reversed transcribed using the Universal cDNA Synthesis Kit II (Exiqon, Denmark). Synthetic cel-miR-39-3p was spiked at this step to control for enzyme inhibition. The reaction was incubated at 42° C. for 60 minutes, and then heat inactivated at 95° C. for 5 minutes. cDNA samples were stored at −20° C. Real Time quantitative PCR (RT-qPCR) analysis of 187 circulating miRNAs (see Supporting Data 1) was conducted using custom 384-well panels (Exiqon, Denmark). For RT-qPCR analysis, cDNA samples were diluted 50-fold and 5 μl were used in individual 10 μl PCR reactions using ExiLENT SYBR® Green master mix and LNA-enhanced miRNA primer assays (Exiqon, Denmark). PCR conditions were 95° C. for 10 minutes, 45 cycles of denaturation (95° C., 10 seconds) and annealing/elongation (60° C., 60 seconds), and melting curve analysis on LC 480 Real Time PCR system (Roche, Germany). The second derivative method was used to calculate the cycle of quantification values (Cq-values).

Results 19 miRNAs, which were significantly regulated between patients with low-traumatic fractures and controls in all 3 subgroups (postmenopausal, premenopausal and male patients with fractures). Three out of 19 miRNAs (15%) were commonly up-regulated (miR-152-5p, miR-335-5p, miR-320a), while 16 (85%) were down-regulated. miRNAs have been found to be statistically significant discriminators between patients with low-traumatic fractures and controls. Eight miRNAs (miR-140-5p, miR-152-3p, miR-30e-5p, miR-324-3p, miR-335-3p, miR-19a-3p, miR-19b-3p, miR-550a-3p) had AUCvalues >0.9 for the classification of fracture patients (see Table 7).

Tables

TABLE 1

MicroRNA regulation in serum of postmenopausal women with fracture

| miRNA ID | Fold Change (log2-transformed) | AveExpr | t | P. Value | adj. P. Val |
|---|---|---|---|---|---|
| hsa-miR-188-3p | −1.84 | 36.69 | 3.52 | 0.001 | 0.112 |
| hsa-miR-576-3p | −1.43 | 37.26 | 3.23 | 0.002 | 0.139 |
| hsa-miR-181a-3p | −1.99 | 38.47 | 3.06 | 0.003 | 0.156 |
| hsa-miR-942 | −1.64 | 37.02 | 2.56 | 0.013 | 0.391 |
| hsa-miR-155-5p | −1.11 | 34.42 | 2.55 | 0.013 | 0.391 |
| hsa-miR-378a-5p | −1.15 | 35.37 | 2.41 | 0.019 | 0.406 |
| hsa-miR-582-3p | −1.51 | 35.5 | 2.35 | 0.021 | 0.406 |
| hsa-miR-550a-5p | 2.08 | 39.97 | −2.36 | 0.021 | 0.406 |
| hsa-miR-502-5p | −1.46 | 36.15 | 2.23 | 0.029 | 0.424 |
| hsa-miR-642a-5p | −1.61 | 37.58 | 2.21 | 0.030 | 0.424 |
| hsa-miR-382-3p | −2.11 | 38.8 | 2.12 | 0.037 | 0.471 |
| hsa-miR-342-5p | −1.05 | 35.66 | 2.07 | 0.042 | 0.476 |
| hsa-miR-369-3p | −1.04 | 35.73 | 2.05 | 0.044 | 0.476 |
| hsa-miR-190a | −1.23 | 35.52 | 1.9 | 0.061 | 0.587 |
| hsa-miR-377-3p | −1.05 | 35.23 | 1.84 | 0.070 | 0.624 |
| hsa-miR-495-3p | −1.02 | 33.77 | 1.71 | 0.092 | 0.624 |
| hsa-miR-500a-5p | −1 | 36.19 | 1.68 | 0.097 | 0.624 |
| hsa-miR-181d | 1.52 | 39.21 | −1.65 | 0.103 | 0.624 |
| hsa-miR-330-3p | 1 | 36.37 | −1.65 | 0.104 | 0.624 |
| hsa-miR-127-3p | −1.59 | 36.79 | 1.45 | 0.150 | 0.642 |
| hsa-miR-1908 | −1.12 | 37.55 | 1.27 | 0.208 | 0.666 |
| hsa-miR-542-5p | −1.46 | 36.75 | 1.23 | 0.222 | 0.666 |
| hsa-miR-203a | 1.11 | 37.77 | −1.15 | 0.256 | 0.689 |

TABLE 2

MicroRNA regulation in serum of type-2 diabetic women with fracture

| miRNA ID | Fold Change (log2-transformed) | AveExpr | t | P. Value | adj. P. Val |
|---|---|---|---|---|---|
| hsa-miR-550a-5p | 4.49 | 39.97 | -5.24 | 0.0000 | 0.0002 |
| hsa-miR-96-5p | 1.35 | 34.22 | -3.79 | 0.0003 | 0.0207 |
| hsa-miR-32-3p | 1.11 | 37.2 | -3.69 | 0.0004 | 0.0207 |
| hsa-miR-7-5p | 1.4 | 33.37 | -3.5 | 0.0008 | 0.0207 |
| hsa-miR-942 | 2.16 | 37.02 | -3.48 | 0.0008 | 0.0207 |
| hsa-miR-16-2-3p | 1.03 | 31.04 | -3.42 | 0.0010 | 0.0207 |
| hsa-miR-203a | 3.2 | 37.77 | -3.41 | 0.0010 | 0.0207 |
| hsa-miR-323a-3p | 1.29 | 36.32 | -3.35 | 0.0013 | 0.0207 |
| hsa-let-7i-5p | 0.91 | 28.75 | -3.26 | 0.0017 | 0.0207 |
| hsa-miR-141-3p | 1.27 | 33.62 | -3.25 | 0.0017 | 0.0207 |
| hsa-miR-181c-3p | 1.47 | 35.32 | -3.25 | 0.0017 | 0.0207 |
| hsa-miR-500a-5p | 1.89 | 36.19 | -3.25 | 0.0017 | 0.0207 |
| hsa-miR-19b-1-5p | 2.16 | 37.14 | -3.24 | 0.0018 | 0.0207 |
| hsa-let-7g-5p | 0.99 | 28.08 | -3.18 | 0.0022 | 0.0235 |
| hsa-miR-92a-3p | 0.81 | 25.97 | -3.13 | 0.0025 | 0.0248 |
| hsa-miR-486-5p | 1.04 | 27.12 | -3.12 | 0.0026 | 0.0248 |
| hsa-miR-21-3p | 1.09 | 35.2 | -3.07 | 0.0030 | 0.0269 |
| hsa-miR-375 | 1.3 | 32.7 | -2.95 | 0.0042 | 0.0352 |
| hsa-miR-301b | 1.25 | 35.31 | -2.93 | 0.0045 | 0.0352 |
| hsa-miR-181c-5p | 1.27 | 35.48 | -2.88 | 0.0052 | 0.0352 |
| hsa-let-7b-5p | 0.97 | 28.72 | -2.87 | 0.0053 | 0.0352 |
| hsa-miR-301a-3p | 1.15 | 31.48 | -2.86 | 0.0055 | 0.0352 |
| hsa-miR-191-5p | 0.99 | 29.06 | -2.85 | 0.0057 | 0.0352 |

TABLE 3

| mature ID | SEQ ID | mature Seq | mature Acc | hairpin | SEQ ID | hairpin Seq | hairpin Acc |
|---|---|---|---|---|---|---|---|
| hsa-let-7b-5p | 1 | UGAGGUAGUAGGUUGUGUGGUU | MIMAT0000063 | hsa-let-7b | 24 | CGGGGUGAGGUAGUAGGUUGUGUGGUUUCAGGGCAGUGAUGUUGCCCCUCGGAAGAUAACUAUACAACCUACUGCCUUCCCUG | MI0000063 |
| hsa-let-7g-5p | 2 | UGAGGUAGUAGUUUGUACAGUU | MIMAT0000414 | hsa-let-7g | 25 | AGGCUGAGGUAGUAGUUUGUACAGUUUGAGGGUCUAUGAUACCACCCGGUACAGGAGAUAACUGUACAGGCCACUGCCUUGCCA | MI0000433 |
| hsa-let-7i-5p | 3 | UGAGGUAGUAGUUUGUGCUGUU | MIMAT0000415 | hsa-let-7i | 26 | CUGGCUGAGGUAGUAGUUUGUGCUGUUGGUCGGGUUGUGACAUUGCCCGCUGUGGAGAUAACUGCGCAAGCUACUGCCUUGCUA | MI0000434 |
| hsa-miR-141-3p | 4 | UAACACUGUCUGGUAAAGAUGG | MIMAT0000432 | hsa-mir-141 | 27 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | MI0000457 |
| hsa-miR-16-2-3p | 5 | CCAAUAUUACUGUGCUGCUUUA | MIMAT0004518 | hsa-miR-16-2 | 28 | GUUCCACUCUAGCAGCACGUAAAUAUUGGCGUAGUGAAAUAUAUAUUAAACACCAAUAUUACUGUGCUGCUUUAGUGUGAC | MI0000115 |
| hsa-miR-181c-3p | 6 | AACCAUCGACCGUUGAGUGGAC | MIMAT0004559 | hsa-mir-181c | 29 | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | MI0000271 |
| hsa-miR-181c-5p | 7 | AACAUUCAACCUGUCGGUGAGU | MIMAT0000258 | hsa-mir-181c | 30 | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | MIM0000271 |
| hsa-miR-191-5p | 8 | CAACGGAAUCCCAAAAGCAGCUG | MIMAT0000440 | hsa-mir-191 | 31 | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU | MI0000465 |
| hsa-miR-19b-1-5p | 9 | AGUUUUGCAGGUUUGCAUCCAGC | MIMAT0004491 | hsa-mir-19b-1 | 32 | CACUGUUCUAUGGUUAGUUUUGCAGGUUUGCAUCCAGCUGUGUGAUAUUCUGCUGUGCAAAUCCAUGCAAAACUGACUGUGGUAGUG | MI0000074 |
| hsa-miR-203a | 10 | GUGAAAUGUUUAGGACCACUAG | MIMAT0000264 | hsa-mir-203a | 33 | GUGUUGGGGACUCGCGCGCUGGGUCCAGUGGUUCUUAACAGUUCAACAGUUCUGUAGCGCAAUUGUGAAAUGUUUAGGACCACUAGACCCGGCGGGCGCGGCGACAGCGA | MI0000283 |

TABLE 3-continued

| mature ID | SEQ ID | mature Seq | mature Acc | hairpin | SEQ ID | hairpin Seq | hairpin Acc |
|---|---|---|---|---|---|---|---|
| hsa-miR-21-3p | 11 | CAACACCAGUCGAUGGGCUGU | MIMAT0004494 | hsa-mir-21 | 34 | UGUCGGGUAGCUUAUCAGACUGAUGUUGACUGUUGAAUCUCAUGGCAACACCAGUCGAUGGGCUGUCUGACA | MI0000077 |
| Hsa-miR143-5p | 12 | GGUGCAGUGCUGCAUCUCUGGU | MIMAT0004599 | hsa-mir-143 | 35 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | MI0000459 |
| hsa-miR-500a-5p | 13 | UAAUCCUUGCUACCUGGGUGAGA | MIMAT0004773 | hsa-mir-500a | 36 | GCUCCCCCUCUCUAAUCCUUGCUACCUGGGUGAGAGUGCUGUCUGAAUGCAAUGCACCUGGGCAAGGAUUCUGAGAGCGAGAGC | MI0003184 |
| hsa-miR-323a-3p | 14 | CACAUUACACGGUCGACCUCU | MIMAT0000755 | hsa-mir-323a | 37 | UUGGUACUUGGAGAGAGGUGGUCCGUGGCGCGUUCGCUUUAUUUAUGGCGCACAUUACACGGUCGACCUCUUUUGCAGUAUCUAAUC | MI0000807 |
| hsa-miR-32-3p | 15 | CAAUUUAGUGUGUGUGAUAUUU | MIMAT0004505 | hsa-mir-32 | 38 | GGAGAUAUUGCACAUUACUAAGUUGCAUGUUGUCACGGCCUCAAUGCAAUUUAGUGUGUGUGAUAUUUUC | MI0000090 |
| hsa-miR-375 | 16 | UUUGUUCGUUCGGCUCGCGUGA | MIMAT0000728 | hsa-mir-375 | 39 | CCCCGCGACGAGCCCCUCGCACAAACCGGACCUGAGCGUUUUGUUCGUUCGGCUCGCGUGAGGC | MI0000783 |
| hsa-miR-486-5p | 17 | UCCUGUACUGAGCUGCCCCGAG | MIMAT0002177 | hsa-mir-486 | 40 | GCAUCCUGUACUGAGCUGCCCCGAGGCCCUUGAUGCUGCCCAGCUCGGGGCAGCUCAGUACAGGAUAC | MI0002470 |
| hsa-miR-500a-5p | 18 | UAAUCCUUGCUACCUGGGUGAGA | MIMAT0004773 | hsa-mir-500a | 41 | GCUCCCCCUCUCUAAUCCUUGCUACCUGGGUGAGAGUGCUGUCUGAAUGCAAUGCACCUGGGCAAGGAUUCUGAGAGCGAGAGC | MI0003184 |
| hsa-miR-550a-5p | 19 | AGUGCCUGAGGGAGUAAGAGCCC | MIMAT0004800 | hsa-mir-550a-1 | 42 | UGAUGCUUUGCUGGCUGGUGCAGUGCCUGAGGGAGUAAGAGCCCUGUUGUGUAAGAUAGUGUCUUACUCCCUCAGGCACAUCUCCAACAAGUCUCU | MI0003600 |
| hsa-miR-7-5p | 20 | UGGAAGACUAGUGAUUUUGUUGU | MIMAT0000252 | hsa-mir-7-1 | 43 | UUGGAUGUUGGCCUAGUUCUGUGUGGAAGACUAGUGAUUUUGUUGUUUUUAGAUAACUAAAUCGACAACAAAUCACAGUCUGCCAUAUGGCACAGGCCAUGCCUCUACAG | MI0000263 |
| hsa-miR-92a-3p | 21 | UAUUGCACUUGUCCCGGCCUGU | MIMAT0000092 | hsa-mir-92a-1 | 44 | CUUUCUACACAGGUUGGGAUCGGUUGCAAUGCUGUGUUUCUGUAUGGUAUUGCACUUGUCCCGGCCUGUUGAGUUUGG | MI0000093 |
| hsa-miR-942-5p | 22 | UCUUCUCUGUUUUGGCCAUGUG | MIMAT0004985 | hsa-mir-942 | 45 | AUUAGGAGAUAUCUUCUCUGUUUUGGCCAUGUGUGUACUCACAGCCCCUCACACAUGGCCGAAACAGAGAAGUUACUUUCCUAAU | MI0005767 |
| hsa-miR-96-5p | 23 | UUUGGCACUAGCACAUUUUUGCU | MIMAT0000095 | hsa-mir-96 | 46 | UGGCCGAUUUUGGCACUAGCACAUUUUUGCUUGUGUCUCUCCGCUCUGAGCAAUCAUGUGCAGUGCCAAUAUGGGAAA | MI0000098 |
| Hsa-miR-382-3p | 47 | AAUCAUUCACGGACAACACUU | MIMAT0022697 | hsa-mir-382 | 48 | UACUUGAAGAGAAGUUGUUCGUGGUGGAUUCGCUUUACUUAUGACGAAUCAUUCACGGACAACACUUUUUUCAGUA | MI0000790 |
| hsa-miR-335-5p | 95 | UCAAGAGCAAUAACGAAAAAUGU | MIMAT0000765 | hsa-mir-335 | 101 | UGUUUUGAGCGGGGGUCAAGAGCAAUAACGAAAAAUGUUUGUCAUAAACCGUUUUUCAUUAUUGCUCCUGACCUCCUCUCAUUUGCUAUAUUCA | MI0000816 |
| hsa-miR-29b-3p | 96 | UAGCACCAUUUGAAAUCAGUGUU | MIMAT0000100 | hsa-mir-29b-1 | 102 | CUUCAGGAAGCUGGUUUCAUAUGGUGGUUUAGAUUUAAAUAGUGAUUGUCUAGCACCAUUUGAAAUCAGUGUUCUUGGGGG | MI0000105 |
| hsa-miR-199b-5p | 97 | CCCAGUGUUUAGACUAUCUGUU | MIMAT0000263 | hsa-mir-199b | 103 | CCAGAGGACACCUCCACUCCGUCUACCCAGUGUUUAGACUAUCUGUUCAGGA | MI0000282 |

TABLE 3-continued

| mature ID | SEQ ID | mature Seq | mature Acc | hairpin ID | SEQ ID | hairpin Seq | hairpin Acc |
|---|---|---|---|---|---|---|---|
| | | | | | | CUCCCAAAUUGUACAGUAGUCUGCAC AUUGGUUAGGCUGGGCUGGGUUAGAC CCUCGG | |
| hsa-miR-214-3p | 98 | ACAGCAGGCAC AGACAGGCAGU | MIMAT0000 271 | hsa-mir-214 | 104 | GGCCUGGCUGGACAGAGUUGUCAUGU GUCUGCCUGUCUACACUUGCUGUGCA GAACAUCCGCUCACCUGUACAGCAGG CACAGACAGGCAGUCACAUGACAACC CAGCCU | MI0000290 |
| hsa-miR-144-5p | 99 | GGAUAUCAUCA UAUACUGUAAG | MIMAT0004 600 | hsa-mir-144 | 105 | UGGGGCCCUGGCUGGGAUAUCAUCAU AUACUGUAAGUUUGCGAUGAGACACU ACAGUAUAGAUGAUGUACUAGUCCGG GCACCCC | MI0000460 |
| hsa-miR-31-5p | 100 | AGGCAAGAUGC UGGCAUAGCU | MIMAT0000 089 | hsa-miR-31 | 106 | GGAGAGGAGGCAAGAUGCUGGCAUAG CUGUUGAACUGGGAACCUGCUAUGCC AACAUAUUGCCAUCUUUCC | MI0000089 |

TABLE 4

| mature ID | SEQ ID | mature Seq | mature Acc | hairpin ID | SEQ ID | hairpin Seq | hairpin Acc |
|---|---|---|---|---|---|---|---|
| hsa-miR-127-3p | 49 | UCGGAUCCGUC UGAGCUUGGCU | MIMAT00004 46 | hsa-mir-127 | 72 | UGUGAUCACUGUCUCCAGCCUGCUGA AGCUCAGAGGGCUCUGAUUCAGAAAU AUCAUCGGAUCCGUCUGAGCUUGGCU GGUCGGAAGUCUCAUCAUC | MI0000472 |
| hsa-miR-155-5p | 50 | UUAAUGCUAAU CGUGAUAGGGG U | MIMAT00006 46 | hsa-mir-155 | 73 | CUGUUAAUGCUAAUCGUGAUAGGGGU UUUUGCCUCCAACUGACUCCUACAUA UUAGCAUUAACAG | MI0000681 |
| hsa-miR-181a-3p | 51 | ACCAUCGACCG UUGAUUGUACC | MIMAT00002 70 | hsa-mir-181a-1 | 74 | UGAGUUUUGAGGUUGCUUCAGUGAAC AUUCAACGCUGUCGGUGAGUUUGGAA UUAAAAUCAAAACCAUCGACCGUUGA UUGUACCCUAUGGCUAACCAUCAUCU ACUCCA | MI0000289 |
| hsa-miR-181d | 52 | AACAUUCAUUG UUGUCGGUGGG U | MIMAT00028 21 | hsa-mir-181d | 75 | GUCCCCUCCCCUAGGCCACAGCCGAG GUCACAAUCAACAUUCAUUGUUGUCG GUGGGUUGUGAGGACUGAGGCCAGAC CCACCGGGGAUGAAUGUCACUGUGG CUGGGCCAGACACGGCUUAAGGGGAA UGGGGAC | MI0003139 |
| hsa-miR-188-3p | 53 | CUCCCACAUGC AGGGUUUGCA | MIMAT00046 13 | hsa-mir-188 | 76 | UGCUCCCUCUCUCACAUCCCUUGCAU GGUGGAGGGUGAGCUUUCUGAAAACC CCUCCCACAUGCAGGGUUUGCAGGAU GGCGAGCC | MI0000484 |
| hsa-miR-1908-5p | 54 | CGGCGGGGAC GGCGAUUGGU C | MIMAT00078 81 | hsa-mir-1908 | 77 | CGGGAAUGCCGCGGCGGGGACGGCGA UUGGUCCGUAUGUGUGGUGCCACCGG CCGCCGGCUCCGCCCCGGCCCCCGCC CC | MI0008329 |
| hsa-miR-190a-5p | 55 | UGAUAUGUUUG AUAUAUUAGGU | MIMAT00004 58 | hsa-mir-190a | 78 | UGCAGGCCUCUGUGUGAUAUGUUUGA UAUAUUAGGUUGUUAUUUAAUCCAAC UAUAUAUCAAACAUAUUCCUACAGUG UCUUGCC | MI0000486 |
| hsa-miR-203a | 56 | GUGAAAUGUUU AGGACCACUAG | MIMAT00002 64 | hsa-mir-203a | 79 | GUGUUGGGGACUCGCGCGCUGGGUCC AGUGGUUCUUAACAGUUCAACAGUUC UGUAGCGCAAUUGUGAAAUGUUUAGG ACCACUAGACCCGGCGGGCGCGGCGA CAGCGA | MI0000283 |
| hsa-miR-330-Ep | 57 | GCAAAGCACAC GGCCUGCAGAG A | MIMAT00007 51 | hsa-mir-330 | 80 | CUUUGGCGAUCACUGCCUCUCUGGGC CUGUGUCUUAGGCUCUGCAAGAUCAA CCGAGCAAAGCACACGGCCUGCAGAG AGGCAGCGCUCUGCCC | MI0000803 |
| hsa-miR-342-5p | 58 | AGGGGUGCUAU CUGUGAUUGA | MIMAT00046 94 | hsa-mir-342 | 81 | GAAACUGGGCUCAAGGUGAGGGGUGC UAUCUGUGAUUGAGGGACAUGGUUAA UGGAAUUGUCUCACACAGAAAUCGCA CCCGUCACCUUGGCCUACUUA | MI0000805 |

TABLE 4-continued

| mature ID | SEQ ID | mature Seq | mature Acc | hairpin | SEQ ID | hairpin Seq | hairpin Acc |
|---|---|---|---|---|---|---|---|
| hsa-miR-369-3p | 59 | AAUAAUACAUGGUUGAUCUUU | MIMAT0000721 | hsa-mir-369 | 82 | UUGAAGGGAGAUCGACCGUGUUAUAUUCGCUUUAUUGACUUCGAAUAAUACAUGGUUGAUCUUUUCUCAG | MI0000777 |
| hsa-miR-377-3p | 60 | AUCACACAAAGGCAACUUUUGU | MIMAT0000730 | hsa-mir-377 | 83 | UUGAGCAGAGGUUGCCCUUGGUGAAUUCGCUUUAUUUAUGUUGAAUCACACAAAGGCAACUUUUGUUUG | MI0000785 |
| hsa-miR-378a-5p | 61 | CUCCUGACUCCAGGUCCUGUGU | MIMAT0000731 | hsa-mir-378a | 84 | AGGGCUCCUGACUCCAGGUCCUGUGUGUUACCUAGAAAUAGCACUGGACUUGGAGUCAGAAGGCCU | MI0000786 |
| hsa-miR-382-3p | 62 | AAUCAUUCACGGACAACACUU | MIMAT0022697 | hsa-mir-382 | 85 | UACUUGAAGAGAAGUUGUUCGUGGUGGAUUCGCUUUACUUAUGACGAAUCAUUCACGGACAACACUUUUUUCAGUA | MI0000790 |
| hsa-miR-495-3p | 63 | AAACAAACAUGGUGCACUUCUU | MIMAT0002817 | hsa-mir-495 | 86 | UGGUACCUGAAAAGAAGUUGCCCAUGUUAUUUUCGCUUUAUAUGUGACGAAACAAACAUGGUGCACUUCUUUUUCGGUAUCA | MI0003135 |
| hsa-miR-500a-5p | 64 | UAAUCCUUGCUACCUGGGUGAGA | MIMAT0004773 | hsa-mir-500a | 87 | GCUCCCCCUCUCUAAUCCUUGCUACCUGGGUGAGAGUGCUGUCUGAAUGCAAUGCACCUGGGCAAGGAUUCUGAGAGCGAGAGC | MI0003184 |
| hsa-miR-502-5p | 65 | AUCCUUGCUAUCUGGGUGCUA | MIMAT0002873 | hsa-mir-502 | 88 | UGCUCCCCCUCUCUAAUCCUUGCUAUCUGGGUGCUAGUGCUGGCUCAAUGCAAUGCACCUGGGCAAGGAUUCAGAGAGGGGAGCU | MI0003186 |
| hsa-miR-542-5p | 66 | UCGGGGAUCAUCAUGUCACGAGA | MIMAT0003340 | hsa-mir-542 | 89 | CAGAUCUCAGACAUCUCGGGGAUCAUCAUGUCACGAGAUACCAGUGUGCACUUGUGACAGAUUGAUAACUGAAAGGUCUGGGAGCCACUCAUCUUCA | MI0003686 |
| hsa-miR-550a-5p | 67 | AGUGCCUGAGGGAGUAAGAGCCC | MIMAT0004800 | hsa-mir-550a-1 | 90 | UGAUGCUUUGCUGGCUGGUGCAGUGCCUGAGGGAGUAAGAGCCCUGUUGUUGUAAAGAUAGUGUCUUACUCCCUCAGGCACAUCUCCAACAAGUCUCU | MI0003600 |
| hsa-miR-576-3p | 68 | AAGAUGUGGAAAAAUUGGAAUC | MIMAT0004796 | hsa-mir-576 | 91 | UACAAUCCAACGAGGAUUCUAAUUUCUCCACGUCUUUGGUAAUAAGGUUUGGCAAAGAUGUGGAAAAAUUGGAAUCCCAUUCGAUUGGUUAUAACCA | MI0003583 |
| hsa-miR-582-3p | 69 | UAACUGGUUGAACAACUGAACC | MIMAT0004797 | hsa-mir-582 | 92 | AUCUGUGCUCUUUGAUUACAGUUGUUCAACCAGUUACUAAUCUAACUAAUUGUAACUGGUUGAACAACUGAACCCCAAAGGGUGCAAAGUAGAAACAUU | MI0003589 |
| hsa-miR-642a-5p | 70 | GUCCCUCUCCAAAUGUGUCUUG | MIMAT0003312 | hsa-mir-642a | 93 | AUCUGAUUGGGGAGGGUCCCUCUCCAAAUGUGUCUUGGGGUGGGGAUCAAGACACAUUUGGAGAGGGAACCUCCCAACUCGGCCUCUGCCAUCAUU | MI0003657 |
| hsa-miR-942 | 71 | UCUUCUCUGUUUUGGCCAUGUG | MIMAT0004985 | hsa-mir-942 | 94 | AUUAGGAGAGUAUCUUCUCUGUUUUGGCCAUGUGUGUACUCACAGCCCCUCACACAUGGCCGAAACAGAGAAGUUACUUUCCUAAU | MI0005767 |

TABLE 5

Post-menopausal Fractures: Top 10 Multiparametric Models and AUC values to differentiate fracture patients from controls

| | Feature 1 | Feature 2 | Feature 3 | Feature 4 | Mean AUC (95% CI) |
|---|---|---|---|---|---|
| Model 1 | miR-382-3p | miR-188-3p | miR-582-3p | miR-550a-5p | 1.000 (0.97 to 1.00) |
| Model 2 | miR-382-3p | miR-188-3p | miR-542-5p | miR-550a-5p | 1.000 (0.96 to 1.00) |
| Model 3 | miR-382-3p | miR-188-3p | miR-542-5p | miR-330-3p | 1.000 (0.96 to 1.00) |
| Model 4 | miR-382-3p | miR-188-3p | miR-495-3p | miR-550a-5p | 0.996 (0.95 to 1.00) |
| Model 5 | miR-382-3p | miR-188-3p | miR-500a-5p | miR-550a-5p | 0.996 (0.95 to 1.00) |
| Model 6 | miR-382-3p | miR-188-3p | miR-542-5p | miR-500a-5p | 0.996 (0.94 to 1.00) |

TABLE 5-continued

Post-menopausal Fractures: Top 10 Multiparametric Models and AUC values to differentiate fracture patients from controls

|  | Feature 1 | Feature 2 | Feature 3 | Feature 4 | Mean AUC (95% CI) |
|---|---|---|---|---|---|
| Model 7 | miR-382-3p | miR-188-3p | miR-181d | miR-550a-5p | 0.993 (0.96 to 1.00) |
| Model 8 | miR-382-3p | miR-188-3p | miR-330-3p | miR-550a-5p | 0.990 (0.96 to 1.00) |
| Model 9 | miR-382-3p | miR-188-3p | miR-642a-5p | miR-582-3p | 0.981 (0.91 to 1.00) |
| Model 10 | miR-382-3p | miR-188-3p | miR-495-3p | miR-181d | 0.975 (0.91 to 1.00) |

TABLE 6

Diabetic Fractures: Top 10 Multiparametric Models and AUC values to differentiate diabetic fracture patients from controls

|  | Feature 1 | Feature 2 | Feature 3 | Feature 4 | Mean AUC (95% CI) |
|---|---|---|---|---|---|
| Model 1 | miR-550a-5p | miR-96-5p | miR-32-3p | miR-375 | 0.961 (0.91 to 0.98) |
| Model 2 | miR-550a-5p | miR-96-5p | miR-141-3p | miR-32-3p | 0.939 (0.89 to 0.96) |
| Model 3 | miR-550a-5p | miR-96-5p | miR-375 | miR-181c-5p | 0.928 (0.87 to 0.95) |
| Model 4 | miR-550a-5p | miR-96-5p | miR-141-3p | miR-375 | 0.919 (0.86 to 0.95) |
| Model 5 | miR-550a-5p | miR-96-5p | miR-32-3p | miR-16-2-3p | 0.919 (0.86 to 0.95) |
| Model 6 | miR-550a-5p | miR-7-5p | miR-96-5p | miR-32-3p | 0.914 (0.85 to 0.95) |
| Model 7 | miR-550a-5p | miR-96-5p | miR-141-3p | let-7g-5p | 0.908 (0.84 to 0.94) |
| Model 8 | miR-550a-5p | miR-96-5p | miR-323a-3p | miR-181c-5p | 0.905 (0.85 to 0.94) |
| Model 9 | miR-550a-5p | miR-181c-3p | miR-96-5p | miR-141-3p | 0.903 (0.83 to 0.93) |
| Model 10 | miR-550a-5p | miR-500a-5p | miR-96-5p | miR-181c-5p | 0.894 (0.83 to 0.93) |

TABLE 7

Differential expression characteristics and classification performance of 19 microRNAs between patients with fractures and controls

| miRNA ID | fold change (group mean OPO vs Ctrl) | p-value | adjusted p-value (Bonferroni-Holm) | AUC (95% CI) |
|---|---|---|---|---|
| hsa-miR-152-3p | 1.79 | 1.95E−15 | 3.65E−13 | 0.962 (0.918-0.993) |
| hsa-miR-30e-5p | 0.50 | 3.79E−15 | 7.05E−13 | 0.959 (0.901-0.997) |
| hsa-miR-140-5p | 0.42 | 4.35E−14 | 8.01E−12 | 0.947 (0.900-0.983) |
| hsa-miR-324-3p | 0.61 | 2.43E−14 | 4.50E−12 | 0.950 (0.885-0.994) |
| hsa-miR-19b-3p | 0.43 | 8.81E−14 | 1.61E−11 | 0.944 (0.879-0.997) |
| hsa-miR-335-5p | 2.16 | 2.27E−13 | 4.14E−11 | 0.939 (0.872-0.986) |
| hsa-miR-19a-3p | 0.49 | 1.19E−12 | 2.15E−10 | 0.929 (0.856-0.983) |
| hsa-miR-550a-3p | 0.45 | 2.89E−11 | 5.19E−09 | 0.909 (0.837-0.970) |
| hsa-miR-186-5p | 0.59 | 1.22E−10 | 2.18E−08 | 0.898 (0.821-0.964) |
| hsa-miR-532-5p | 0.53 | 1.34E−10 | 2.39E−08 | 0.898 (0.810-0.968) |
| hsa-miR-93-5p | 0.58 | 1.40E−09 | 2.47E−07 | 0.879 (0.797-0.947) |
| hsa-miR-378a-5p | 0.44 | 3.36E−09 | 5.88E−07 | 0.872 (0.785-0.940) |
| hsa-miR-320a | 1.80 | 4.34E−09 | 7.55E−07 | 0.870 (0.781-0.942) |
| hsa-miR-16-5p | 0.48 | 1.75E−08 | 3.01E−06 | 0.857 (0.761-0.940) |
| hsa-miR-215-5p | 0.58 | 2.80E−08 | 4.76E−06 | 0.853 (0.761-0.930) |
| hsa-let-7b-5p | 0.64 | 3.02E−08 | 5.08E−06 | 0.852 (0.756-0.929) |
| hsa-miR-29b-3p | 0.63 | 1.25E−07 | 2.06E−05 | 0.838 (0.737-0.930) |
| hsa-miR-7-5p | 0.51 | 5.02E−07 | 7.89E−05 | 0.824 (0.720-0.917) |
| hsa-miR-365a-3p | 0.48 | 1.84E−06 | 2.74E−04 | 0.809 (0.707-0.898) |

LITERATURE

Anastas, J. N., & Moon, R. T. (2013). WNT signalling pathways as therapeutic targets in cancer. *Nature Reviews Cancer*, 13(1), 11-26. doi:10.1038/nrc3419

Augustine, M., & Horwitz, J. M. (2013). Parathyroid Hormone and Parathyroid Hormone-related Protein Analogs as Therapies for Osteoporosis. *Current Osteoporosis Reports*, 11(4), 1-11. Bartel, D. P. (2009). MicroRNAs: target recognition and regulatory functions. *Cell*, 136(2), 215-233. doi:10.1016/j.cell.2009.01.002

Boeckel J N, et al., Heparin selectively affects the quantification of microRNAs in human blood samples, 2013, Clin. Chem. 59, 1125-1127

Canalis, E. (2013). Wnt signalling in osteoporosis: mechanisms and novel therapeutic approaches. *Nature Reviews. Endocrinology*, 9(10), 575-83. doi:10.1038/nrendo.2013.154

Cefalu, C. A. (2004). Is bone mineral density predictive of fracture risk reduction? *Current Medical Research and Opinion*, 20(3), 341-349. doi:10.1185/030079903125003062

Chen C., et al., 2008, Characterization of microRNAs in serum: a novel class of biomarkers for diagnosis of cancer and other diseases. cell res. 18, 997-1006

Cheng H H et al., Plasma processing conditions substantially influence circulating microRNA biomarkerlevels. PLos One 8, 1-11

Cosman, F., Crittenden, D. B., Adachi, J. D., Binkley, N., Czerwinski, E., Ferrari, S., . . . Grauer, A. (2016). Romosozumab Treatment in Postmenopausal Women with Osteoporosis. *New England Journal of Medicine*, NEJMoa1607948. http://doi.org/10.1056/NEJMoa1607948

Cummings, S. R., San Martin, J., McClung, M. R., Siris, E. S., Eastell, R., Reid, I. R., . . . Christiansen, C. (2009). Denosumab for prevention of fractures in postmenopausal women with osteoporosis. *The New England Journal of Medicine*, 361(8), 756-65.

Deng, Y., Bi, X., Zhou, H., You, Z., Wang, Y., Gu, P., & Fan, X. (2014). Repair of critical-sized bone defects with anti-miR-31-expressing bone marrow stromal stem cells and poly(glycerol sebacate) scaffolds. *European Cells & Materials*, 27, 13-24; discussion 24-5. Retrieved from http://www.ncbi.nlm.nih.gov/pubmed/24425157

Dong, S., Yang, B., Guo, H., & Kang, F. (2012). MicroRNAs regulate osteogenesis and chondrogenesis. *Biochemical and Biophysical Research Communications*, 418(4), 587-591. doi:10.1016/j.bbrc.2012.01.075

Garcia, M E et al., 2002, Anticoagulants interfere with PCR used to diagnose invasive aspergillosis. J. Clin. Microbiol. 40, 1567-1568

Gronholz, M. J. (2008). Prevention, Diagnosis, and Management of Osteoporosis-Related Fracture: A Multifactoral Osteopathic Approach. *The Journal of the American Osteopathic Association*, 108(10), S4-S85.

Harvey, N., Dennison, E., & Cooper, C. (2010). Osteoporosis: impact on health and economics. *Nature Reviews. Rheumatology*, 6(2), 99-105. Kanis, J. A., McCloskey, E. V, Johansson, H., Cooper, C., Rizzoli, R., Reginster, J.-Y., & Scientific Advisory Board of the European Society for Clinical and Economic Aspects of Osteoporosis and Osteoarthritis (ESCEO) and the Committee of Scientific Advisors of the International Osteoporosis Foundation (IOF). (2013). European guidance for the diagnosis and management of osteoporosis in postmenopausal women. *Osteoporosis International: A Journal Established as Result of Cooperation between the European Foundation for Osteoporosis and the National Osteoporosis Foundation of the USA*, 24(1), 23-57. doi:10.1007/s00198-012-2074-y Kapinas, K., Kessler, C. B., & Delany, A. M. (2009). miR-29 suppression of osteonectin in osteoblasts: regulation during differentiation and by canonical Wnt signaling. *Journal of Cellular Biochemistry*, 108(1), 216-224. doi:10.1002/jcb.22243

Keller, A., Leidinger, P., Bauer, A., Elsharawy, A., Haas, J., Backes, C., . . . Meese, E. (2011). Toward the blood-borne miRNome of human diseases. *Nature Methods*, 8(10), 841-3. doi:10.1038/nmeth.1682

Kim D J et al., 2012, Plasma components affects accuracy of circulating cancer-related microRNA quantitation. J. Mol. Diagn. 14, 71-80

Li, Z., Hassan, M. Q., Volinia, S., van Wijnen, A. J., Stein, J. L., Croce, C. M., . . . Stein, G. S. (2008). A microRNA signature for a BMP2-induced osteoblast lineage commitment program. *Proceedings of the National Academy of Sciences of the United States of America*, 105(37), 13906-13911. doi:10.1073/pnas.0804438105

Rubin, K. H., Abrahamsen, B., Friis-Holmberg, T., Hjelmborg, J. V. B., Bech, M., Hermann, A. P., . . . Brixen, K. (2013). Comparison of different screening tools (FRAX®, OST, ORAI, OSIRIS, SCORE and age alone) to identify women with increased risk of fracture. A population-based prospective study. *Bone*, 56(1), 16-22. doi:10.1016/j.bone.2013.05.002

Seeliger, C., Karpinski, K., Haug, A., Vester, H., Schmitt, A., Bauer, J., & van Griensven, M. (2014). Five Freely Circulating miRNAs and Bone Tissue miRNAs are Associated with Osteoporotic Fractures. *Journal of Bone and Mineral Research: The Official Journal of the American Society for Bone and Mineral Research*. doi:10.1002/jbmr.2175

Trompeter, H.-I., Dreesen, J., Hermann, E., Iwaniuk, K. M., Hafner, M., Renwick, N., . . . Wernet, P. (2013). MicroRNAs miR-26a, miR-26b, and miR-29b accelerate osteogenic differentiation of unrestricted somatic stem cells from human cord blood. *BMC Genomics*, 14(1), 111. doi:10.1186/1471-2164-14-111

Van Wijnen, A. J., van de Peppel, J., van Leeuwen, J. P., Lian, J. B., Stein, G. S., Westendorf, J. J., . . . Kakar, S. (2013). MicroRNA functions in osteogenesis and dysfunctions in osteoporosis. *Current Osteoporosis Reports*, 11(2), 72-82. doi:10.1007/s11914-013-0143-6

Vasikaran, S., Eastell, R., Bruyère, O., Foldes, A. J., Garnero, P., Griesmacher, A., . . . IOF-IFCC Bone Marker Standards Working Group. (2011). Markers of bone turnover for the prediction of fracture risk and monitoring of osteoporosis treatment: a need for international reference standards. *Osteoporosis International: A Journal Established as Result of Cooperation between the European Foundation for Osteoporosis and the National Osteoporosis Foundation of the USA*, 22(2), 391-420. doi:10.1007/s00198-010-1501-1

Weilner, S., Schraml, E., Redl, H., Grillari-Voglauer, R., & Grillari, J. (2013). Secretion of microvesicular miRNAs in cellular and organismal aging. *Experimental Gerontology*, 48(7), 626-633. doi:10.1016/j.exger.2012.11.017

Zhao, X., Xu, D., Li, Y., Zhang, J., Liu, T., Ji, Y., . . . Xie, X. (2013). MicroRNAs regulate bone metabolism. *Journal of Bone and Mineral Metabolism*. doi:10.1007/s00774-013-0537-7

The invention claimed is:

1. An in vitro method of diagnosing osteoporosis or determining the risk of osteoporotic fractures or monitoring of treatment in a subject, comprising the steps of:
   a) providing a sample from said subject,
   b) measuring the level of hsa-miR-203a in combination with the level of at least one miRNA selected from the group consisting of hsa-miR-144-3p, hsa-miR-188-3p, hsa-miR-382-3p, hsa-miR-127-3p, hsa-miR-155-5p, hsa-miR-181a-3p, hsa-miR-1908, hsa-miR-190a, hsa-miR-199b-5p, hsa-miR-214-3p, hsa-miR-29b-3p, hsa-miR-330-3p, hsa-miR-335-5p, hsa-miR-31-5p, hsa-miR-342-5p, hsa-miR-369-3p, hsa-miR-377-3p, hsa-miR-378a-5p, hsa-miR-495-3p, hsa-miR-500a-5p, hsa-miR-502-5p, hsa-miR-542-5p, hsa-miR-550a-5p, hsa-miR-576-3p, hsa-miR-582-3p, hsa-miR-642a-5p, hsa-miR-942, hsa-let-7b-5p and hsa-miR-181d or isoforms or variants thereof,
   c) comparing the level of said miRNAs to a reference level, wherein the reference level is the average level of corresponding miRNAs in subjects not suffering from osteoporosis, and
   wherein a magnitude of difference of more than one standard deviation in said level of the miRNAs when compared to the reference level is indicative of osteoporosis or the risk of fractures, and
   d) treating the subject with an anti-resorptive treatment to stabilize bone mass or with an anabolic treatment to increase bone mass when said magnitude of difference is more than one standard deviation.

2. The method according to claim 1, wherein the level of all of hsa-miR-203a, hsa-miR-330-3p, hsa-miR-188-3p, hsa-miR-550a-5p, hsa-miR-335-5p, hsa-miR-29b-3p, hsa-miR-214-3p and hsa-miR-31-5p is measured.

3. The method according to claim 1, wherein the subject is a post menopausal female, a type 2 diabetes mellitus patient, an osteoporosis patient, or an osteopenia patient, suffering from or at risk of developing bone fractures.

4. The method according to claim 1, wherein the level of at least 3, at least 4, at least 5, or up to 30 miRNAs is measured.

5. The method according to claim 1, wherein the level of said miRNAs is compared with the average level of corresponding miRNAs in healthy subjects, wherein a difference by more than one standard deviations is indicative of osteoporosis with increased risk of future fractures.

6. The method according to claim 1, wherein the level of all of the miRNAs is measured.

7. The method according to claim 1, wherein the difference in miRNA levels is determined by quantitative or digital PCR, sequencing, microarray, Luminex nucleic acid assays, or other hybridization-based techniques.

8. The method according to claim 1, wherein the anti-resorptive treatment comprises the administration of bisphosphonates or monoclonal antibodies against RANKL to the subject.

9. The method according to claim 1, wherein the anabolic treatment comprises the administration of parathyroid hormone or monoclonal antibodies against Sclerostin to the subject.

* * * * *

SEQUENCE LISTING

<160> NUMBER OF SEQ ID NOS: 106

<210> SEQ ID NO 1
<211> LENGTH: 22
<212> TYPE: RNA
<213> ORGANISM: Homo sapiens
<220> FEATURE:
<223> OTHER INFORMATION: hsa-let-7b-5p

<400> SEQUENCE: 1
ugagguagua gguugugugg uu                     22

```
<210> SEQ ID NO 2
<211> LENGTH: 22
<212> TYPE: RNA
<213> ORGANISM: Homo sapiens
<220> FEATURE:
<223> OTHER INFORMATION: hsa-let-7g-5p

<400> SEQUENCE: 2
ugagguagua guuuguacag uu                                           22

<210> SEQ ID NO 3
<211> LENGTH: 22
<212> TYPE: RNA
<213> ORGANISM: Homo sapiens
<220> FEATURE:
<223> OTHER INFORMATION: hsa-let-7i-5p

<400> SEQUENCE: 3
ugagguagua guuugugcug uu                                           22

<210> SEQ ID NO 4
<211> LENGTH: 22
<212> TYPE: RNA
<213> ORGANISM: Homo sapiens
<220> FEATURE:
<223> OTHER INFORMATION: hsa-miR-141-3p

<400> SEQUENCE: 4
uaacacuguc ugguaaagau gg                                           22

<210> SEQ ID NO 5
<211> LENGTH: 22
<212> TYPE: RNA
<213> ORGANISM: Homo sapiens
<220> FEATURE:
<223> OTHER INFORMATION: hsa-miR-16-2-3p

<400> SEQUENCE: 5
ccaauauuac ugugcugcuu ua                                           22

<210> SEQ ID NO 6
<211> LENGTH: 22
<212> TYPE: RNA
<213> ORGANISM: Homo sapiens
<220> FEATURE:
<223> OTHER INFORMATION: hsa-miR-181c-3p

<400> SEQUENCE: 6
aaccaucgac cguugagugg ac                                           22

<210> SEQ ID NO 7
<211> LENGTH: 22
<212> TYPE: RNA
<213> ORGANISM: Homo sapiens
<220> FEATURE:
<223> OTHER INFORMATION: hsa-miR-181c-5p

<400> SEQUENCE: 7
aacauucaac cugucggug a gu                                          22

<210> SEQ ID NO 8
<211> LENGTH: 23
<212> TYPE: RNA
<213> ORGANISM: Homo sapiens
<220> FEATURE:
<223> OTHER INFORMATION: hsa-miR-191-5p
```

```
<400> SEQUENCE: 8
caacggaauc ccaaaagcag cug                                          23

<210> SEQ ID NO 9
<211> LENGTH: 23
<212> TYPE: RNA
<213> ORGANISM: Homo sapiens
<220> FEATURE:
<223> OTHER INFORMATION: hsa-miR-19b-1-5p

<400> SEQUENCE: 9
aguuuugcag guuugcaucc agc                                          23

<210> SEQ ID NO 10
<211> LENGTH: 22
<212> TYPE: RNA
<213> ORGANISM: Homo sapiens
<220> FEATURE:
<223> OTHER INFORMATION: hsa-miR-203a

<400> SEQUENCE: 10
gugaaauguu uaggaccacu ag                                           22

<210> SEQ ID NO 11
<211> LENGTH: 21
<212> TYPE: RNA
<213> ORGANISM: Homo sapiens
<220> FEATURE:
<223> OTHER INFORMATION: hsa-miR-21-3p

<400> SEQUENCE: 11
caacaccagu cgaugggcug u                                            21

<210> SEQ ID NO 12
<211> LENGTH: 22
<212> TYPE: RNA
<213> ORGANISM: Homo sapiens
<220> FEATURE:
<223> OTHER INFORMATION: hsa-miR143-5p

<400> SEQUENCE: 12
ggugcagugc ugcaucucug gu                                           22

<210> SEQ ID NO 13
<211> LENGTH: 23
<212> TYPE: RNA
<213> ORGANISM: Homo sapiens
<220> FEATURE:
<223> OTHER INFORMATION: hsa-miR-500a-5p

<400> SEQUENCE: 13
uaauccuugc uaccugggug aga                                          23

<210> SEQ ID NO 14
<211> LENGTH: 21
<212> TYPE: RNA
<213> ORGANISM: Homo sapiens
<220> FEATURE:
<223> OTHER INFORMATION: hsa-miR-323a-3p

<400> SEQUENCE: 14
cacauuacac ggucgaccuc u                                            21

<210> SEQ ID NO 15
```

<211> LENGTH: 22
<212> TYPE: RNA
<213> ORGANISM: Homo sapiens
<220> FEATURE:
<223> OTHER INFORMATION: hsa-miR-32-3p

<400> SEQUENCE: 15
caauuuagug ugugugauau uu                                              22

<210> SEQ ID NO 16
<211> LENGTH: 22
<212> TYPE: RNA
<213> ORGANISM: Homo sapiens
<220> FEATURE:
<223> OTHER INFORMATION: hsa-miR-375

<400> SEQUENCE: 16
uuuguucguu cggcucgcgu ga                                              22

<210> SEQ ID NO 17
<211> LENGTH: 22
<212> TYPE: RNA
<213> ORGANISM: Homo sapiens
<220> FEATURE:
<223> OTHER INFORMATION: hsa-miR-486-5p

<400> SEQUENCE: 17
uccuguacug agcugccccg ag                                              22

<210> SEQ ID NO 18
<211> LENGTH: 23
<212> TYPE: RNA
<213> ORGANISM: Homo sapiens
<220> FEATURE:
<223> OTHER INFORMATION: hsa-miR-500a-5p

<400> SEQUENCE: 18
uaauccuugc uaccugggug aga                                             23

<210> SEQ ID NO 19
<211> LENGTH: 23
<212> TYPE: RNA
<213> ORGANISM: Homo sapiens
<220> FEATURE:
<223> OTHER INFORMATION: hsa-miR-550a-5p

<400> SEQUENCE: 19
agugccugag ggaguaagag ccc                                             23

<210> SEQ ID NO 20
<211> LENGTH: 23
<212> TYPE: RNA
<213> ORGANISM: Homo sapiens
<220> FEATURE:
<223> OTHER INFORMATION: hsa-miR-7-5p

<400> SEQUENCE: 20
uggaagacua gugauuuugu ugu                                             23

<210> SEQ ID NO 21
<211> LENGTH: 22
<212> TYPE: RNA
<213> ORGANISM: Homo sapiens
<220> FEATURE:
<223> OTHER INFORMATION: hsa-miR-92a-3p

<400> SEQUENCE: 21

```
uauugcacuu gucccggccu gu                                              22

<210> SEQ ID NO 22
<211> LENGTH: 22
<212> TYPE: RNA
<213> ORGANISM: Homo sapiens
<220> FEATURE:
<223> OTHER INFORMATION: hsa-miR-942-5p

<400> SEQUENCE: 22
ucuucucugu uuuggccaug ug                                              22

<210> SEQ ID NO 23
<211> LENGTH: 23
<212> TYPE: RNA
<213> ORGANISM: Homo sapiens
<220> FEATURE:
<223> OTHER INFORMATION: hsa-miR-96-5p

<400> SEQUENCE: 23
uuuggcacua gcacauuuuu gcu                                             23

<210> SEQ ID NO 24
<211> LENGTH: 83
<212> TYPE: RNA
<213> ORGANISM: Homo sapiens
<220> FEATURE:
<223> OTHER INFORMATION: hsa-let-7b

<400> SEQUENCE: 24
cggggugagg uaguagguug ugugguuuca gggcagugau guugcccuc ggaagauaac      60 uauacaaccu acugccuucc cug                                             83

<210> SEQ ID NO 25
<211> LENGTH: 84
<212> TYPE: RNA
<213> ORGANISM: Homo sapiens
<220> FEATURE:
<223> OTHER INFORMATION: hsa-let-7g

<400> SEQUENCE: 25
aggcugaggu aguaguuugu acaguuugag ggucuaugau accacccggu acaggagaua    60
acuguacagg ccacugccuu gcca                                            84

<210> SEQ ID NO 26
<211> LENGTH: 84
<212> TYPE: RNA
<213> ORGANISM: Homo sapiens
<220> FEATURE:
<223> OTHER INFORMATION: hsa-let-7i

<400> SEQUENCE: 26
cuggcugagg uaguaguuug ugcuguuggu cgguuguga cauugcccgc uguggagaua     60
acugcgcaag cuacugccuu gcua                                            84

<210> SEQ ID NO 27
<211> LENGTH: 95
<212> TYPE: RNA
<213> ORGANISM: Homo sapiens
<220> FEATURE:
<223> OTHER INFORMATION: hsa-mir-141

<400> SEQUENCE: 27
```
cggccggccc uggguccauc uuccaguaca guguuggaug gucuaauugu gaagcuccua        60
acacugucug guaaagaugg cucccgggug gguuc                                   95

<210> SEQ ID NO 28
<211> LENGTH: 81
<212> TYPE: RNA
<213> ORGANISM: Homo sapiens
<220> FEATURE:
<223> OTHER INFORMATION: hsa-mir-16-2

<400> SEQUENCE: 28
guuccacucu agcagcacgu aaauauuggc guagugaaau auauauuaaa caccaauauu        60
acugugcugc uuuaguguga c                                                  81

<210> SEQ ID NO 29
<211> LENGTH: 110
<212> TYPE: RNA
<213> ORGANISM: Homo sapiens
<220> FEATURE:
<223> OTHER INFORMATION: hsa-mir-181c

<400> SEQUENCE: 29
cggaaaauuu gccaaggguu uggggaaca uucaaccugu cggugaguuu gggcagcuca        60
ggcaaaccau cgaccguuga guggacccug aggccuggaa uugccauccu                  110

<210> SEQ ID NO 30
<211> LENGTH: 110
<212> TYPE: RNA
<213> ORGANISM: Homo sapiens
<220> FEATURE:
<223> OTHER INFORMATION: hsa-mir-181c

<400> SEQUENCE: 30
cggaaaauuu gccaaggguu uggggaaca uucaaccugu cggugaguuu gggcagcuca        60
ggcaaaccau cgaccguuga guggacccug aggccuggaa uugccauccu                  110

<210> SEQ ID NO 31
<211> LENGTH: 92
<212> TYPE: RNA
<213> ORGANISM: Homo sapiens
<220> FEATURE:
<223> OTHER INFORMATION: hsa-mir-191

<400> SEQUENCE: 31
cggcuggaca gcgggcaacg gaaucccaaa agcagcuguu gucuccagag cauuccagcu       60
gcgcuuggau uucgucucccu gcucuccugc cu                                    92

<210> SEQ ID NO 32
<211> LENGTH: 87
<212> TYPE: RNA
<213> ORGANISM: Homo sapiens
<220> FEATURE:
<223> OTHER INFORMATION: hsa-mir-19b-1

<400> SEQUENCE: 32
cacuguucua ugguuaguuu ugcagguuug cauccagcug ugugauauuc ugcugugcaa       60
auccaugcaa aacugacugu gguagug                                           87

<210> SEQ ID NO 33
<211> LENGTH: 110
<212> TYPE: RNA
<213> ORGANISM: Homo sapiens

```
<220> FEATURE:
<223> OTHER INFORMATION: hsa-mir-203a

<400> SEQUENCE: 33
guguugggga cucgcgcgcu ggguccagug guucuuaaca guucaacagu ucuguagcgc    60
aauugugaaa uguuuaggac cacuagaccc ggcgggcgcg gcgacagcga               110

<210> SEQ ID NO 34
<211> LENGTH: 72
<212> TYPE: RNA
<213> ORGANISM: Homo sapiens
<220> FEATURE:
<223> OTHER INFORMATION: hsa-mir-21

<400> SEQUENCE: 34
ugucggguag cuuaucagac ugauguugac uguugaaucu cauggcaaca ccagucgaug    60
ggcugucuga ca                                                        72

<210> SEQ ID NO 35
<211> LENGTH: 106
<212> TYPE: RNA
<213> ORGANISM: Homo sapiens
<220> FEATURE:
<223> OTHER INFORMATION: hsa-mir-143

<400> SEQUENCE: 35
gcgcagcgcc cugucuccca gccugaggug cagugcugca ucucggucga guugggaguc    60
ugagaugaag cacuguagcu caggaagaga gaaguuguuc ugcagc                   106

<210> SEQ ID NO 36
<211> LENGTH: 84
<212> TYPE: RNA
<213> ORGANISM: Homo sapiens
<220> FEATURE:
<223> OTHER INFORMATION: hsa-mir-500a

<400> SEQUENCE: 36 gcuccccuc ucuaauccuu gcuaccuggg ugagagugcu gucugaaugc aaugcaccug     60
ggcaaggauu cugagagcga gagc                                           84

<210> SEQ ID NO 37
<211> LENGTH: 86
<212> TYPE: RNA
<213> ORGANISM: Homo sapiens
<220> FEATURE:
<223> OTHER INFORMATION: hsa-mir-323a

<400> SEQUENCE: 37
uugguacuug gagagaggug guccguggcg cguucgcuuu auuuauggcg cacauuacac    60
ggucgaccuc uuugcaguau cuaauc                                         86

<210> SEQ ID NO 38
<211> LENGTH: 70
<212> TYPE: RNA
<213> ORGANISM: Homo sapiens
<220> FEATURE:
<223> OTHER INFORMATION: hsa-mir-32

<400> SEQUENCE: 38
ggagauauug cacauuacua aguugcaugu ugcacggcc ucaaugcaau uuagugugug     60
ugauauuuuc                                                           70
```

```
<210> SEQ ID NO 39
<211> LENGTH: 64
<212> TYPE: RNA
<213> ORGANISM: Homo sapiens
<220> FEATURE:
<223> OTHER INFORMATION: hsa-mir-375

<400> SEQUENCE: 39
ccccgcgacg agccccucgc acaaaccgga ccugagcguu uuguucguuc ggcucgcgug      60
aggc                                                                  64

<210> SEQ ID NO 40
<211> LENGTH: 68
<212> TYPE: RNA
<213> ORGANISM: Homo sapiens
<220> FEATURE:
<223> OTHER INFORMATION: hsa-mir-486

<400> SEQUENCE: 40
gcauccugua cugagcugcc ccgaggcccu ucaugcugcc cagcucgggg cagcucagua      60
caggauac                                                              68

<210> SEQ ID NO 41
<211> LENGTH: 84
<212> TYPE: RNA
<213> ORGANISM: Homo sapiens
<220> FEATURE:
<223> OTHER INFORMATION: hsa-mir-500a

<400> SEQUENCE: 41 gcuccccuc ucuaauccuu gcuaccuggg ugagagugcu gucugaaugc aaugcaccug       60
ggcaaggauu cugagagcga gagc                                            84

<210> SEQ ID NO 42
<211> LENGTH: 97
<212> TYPE: RNA
<213> ORGANISM: Homo sapiens
<220> FEATURE:
<223> OTHER INFORMATION: hsa-mir-550a-1

<400> SEQUENCE: 42
ugaugcuuug cuggcuggug cagugccuga gggaguaaga gcccuguugu uguaagauag      60
ugucuuacuc ccucaggcac aucccaaca agucucu                               97

<210> SEQ ID NO 43
<211> LENGTH: 110
<212> TYPE: RNA
<213> ORGANISM: Homo sapiens
<220> FEATURE:
<223> OTHER INFORMATION: hsa-mir-7-1

<400> SEQUENCE: 43
uuggauguug gccuaguucu gugugaaga cuagugauuu uguuguuuuu agauaacuaa       60
aucgacaaca aaucacaguc ugccauaugg cacaggccau gccucuacag                110

<210> SEQ ID NO 44
<211> LENGTH: 78
<212> TYPE: RNA
<213> ORGANISM: Homo sapiens
<220> FEATURE:
<223> OTHER INFORMATION: hsa-mir-92a-1

<400> SEQUENCE: 44
```

```
cuuucuacac agguugggau cgguugcaau gcuguguuuc uguaugguau ugcacuuguc    60
ccggccuguu gaguuugg                                                  78

<210> SEQ ID NO 45
<211> LENGTH: 86
<212> TYPE: RNA
<213> ORGANISM: Homo sapiens
<220> FEATURE:
<223> OTHER INFORMATION: hsa-mir-942

<400> SEQUENCE: 45
auuaggagag uaucuucucu guuuuggcca uguguguacu cacagccccu cacacauggc    60
cgaaacagag aaguuacuuu ccuaau                                         86

<210> SEQ ID NO 46
<211> LENGTH: 78
<212> TYPE: RNA
<213> ORGANISM: Homo sapiens
<220> FEATURE:
<223> OTHER INFORMATION: hsa-mir-96

<400> SEQUENCE: 46
uggccgauuu uggcacuagc acauuuuugc uugugucucu ccgcucugag caaucaugug    60
cagugccaau augggaaa                                                  78

<210> SEQ ID NO 47
<211> LENGTH: 21
<212> TYPE: RNA
<213> ORGANISM: Homo sapiens
<220> FEATURE:
<223> OTHER INFORMATION: hsa-miR-382-3p

<400> SEQUENCE: 47
aaucauucac ggacaacacu u                                              21

<210> SEQ ID NO 48
<211> LENGTH: 76
<212> TYPE: RNA
<213> ORGANISM: Homo sapiens
<220> FEATURE:
<223> OTHER INFORMATION: hsa-mir-382

<400> SEQUENCE: 48
uacuugaaga gaaguuguuc gugguggauu cgcuuuacuu augacgaauc auucacggac    60
aacacuuuuu ucagua                                                    76

<210> SEQ ID NO 49
<211> LENGTH: 22
<212> TYPE: RNA
<213> ORGANISM: Homo sapiens
<220> FEATURE:
<223> OTHER INFORMATION: hsa-miR-127-3p

<400> SEQUENCE: 49
ucggauccgu cugagcuugg cu                                             22

<210> SEQ ID NO 50
<211> LENGTH: 23
<212> TYPE: RNA
<213> ORGANISM: Homo sapiens
<220> FEATURE:
<223> OTHER INFORMATION: hsa-miR-155-5p
```

```
<400> SEQUENCE: 50
uuaaugcuaa ucgugauagg ggu                                              23

<210> SEQ ID NO 51
<211> LENGTH: 22
<212> TYPE: RNA
<213> ORGANISM: Homo sapiens
<220> FEATURE:
<223> OTHER INFORMATION: hsa-miR-181a-3p

<400> SEQUENCE: 51
accaucgacc guugauugua cc                                               22

<210> SEQ ID NO 52
<211> LENGTH: 23
<212> TYPE: RNA
<213> ORGANISM: Homo sapiens
<220> FEATURE:
<223> OTHER INFORMATION: hsa-miR-181d

<400> SEQUENCE: 52
aacauucauu guguucggug ggu                                              23

<210> SEQ ID NO 53
<211> LENGTH: 21
<212> TYPE: RNA
<213> ORGANISM: Homo sapiens
<220> FEATURE:
<223> OTHER INFORMATION: hsa-miR-188-3p

<400> SEQUENCE: 53
cucccacaug caggguuugc a                                                21

<210> SEQ ID NO 54
<211> LENGTH: 21
<212> TYPE: RNA
<213> ORGANISM: Homo sapiens
<220> FEATURE:
<223> OTHER INFORMATION: hsa-miR-1908-5p

<400> SEQUENCE: 54
cggcggggac ggcgauuggu c                                                21

<210> SEQ ID NO 55
<211> LENGTH: 22
<212> TYPE: RNA
<213> ORGANISM: Homo sapiens
<220> FEATURE:
<223> OTHER INFORMATION: hsa-miR-190a-5p

<400> SEQUENCE: 55
ugauauguuu gauauauuag gu                                               22

<210> SEQ ID NO 56
<211> LENGTH: 22
<212> TYPE: RNA
<213> ORGANISM: Homo sapiens
<220> FEATURE:
<223> OTHER INFORMATION: hsa-miR-203a

<400> SEQUENCE: 56
gugaaauguu uaggaccacu ag                                               22

<210> SEQ ID NO 57
<211> LENGTH: 23
```

```
<212> TYPE: RNA
<213> ORGANISM: Homo sapiens
<220> FEATURE:
<223> OTHER INFORMATION: hsa-miR-330-3p

<400> SEQUENCE: 57
gcaaagcaca cggccugcag aga                                        23

<210> SEQ ID NO 58
<211> LENGTH: 21
<212> TYPE: RNA
<213> ORGANISM: Homo sapiens
<220> FEATURE:
<223> OTHER INFORMATION: hsa-miR-342-5p

<400> SEQUENCE: 58
aggggugcua ucugugauug a                                          21

<210> SEQ ID NO 59
<211> LENGTH: 21
<212> TYPE: RNA
<213> ORGANISM: Homo sapiens
<220> FEATURE:
<223> OTHER INFORMATION: hsa-miR-369-3p

<400> SEQUENCE: 59
aauaauacau gguugaucuu u                                          21

<210> SEQ ID NO 60
<211> LENGTH: 22
<212> TYPE: RNA
<213> ORGANISM: Homo sapiens
<220> FEATURE:
<223> OTHER INFORMATION: hsa-miR-377-3p

<400> SEQUENCE: 60
aucacacaaa ggcaacuuuu gu                                         22

<210> SEQ ID NO 61
<211> LENGTH: 22
<212> TYPE: RNA
<213> ORGANISM: Homo sapiens
<220> FEATURE:
<223> OTHER INFORMATION: hsa-miR-378a-5p

<400> SEQUENCE: 61
cuccugacuc cagguccugu gu                                         22

<210> SEQ ID NO 62
<211> LENGTH: 21
<212> TYPE: RNA
<213> ORGANISM: Homo sapiens
<220> FEATURE:
<223> OTHER INFORMATION: hsa-miR-382-3p

<400> SEQUENCE: 62
aaucauucac ggacaacacu u                                          21

<210> SEQ ID NO 63
<211> LENGTH: 22
<212> TYPE: RNA
<213> ORGANISM: Homo sapiens
<220> FEATURE:
<223> OTHER INFORMATION: hsa-miR-495-3p

<400> SEQUENCE: 63
```
aaacaaacau ggugcacuuc uu                    22

<210> SEQ ID NO 64
<211> LENGTH: 23
<212> TYPE: RNA
<213> ORGANISM: Homo sapiens
<220> FEATURE:
<223> OTHER INFORMATION: hsa-miR-500a-5p

<400> SEQUENCE: 64
uaauccuugc uaccuggguga aga                  23

<210> SEQ ID NO 65
<211> LENGTH: 21
<212> TYPE: RNA
<213> ORGANISM: Homo sapiens
<220> FEATURE:
<223> OTHER INFORMATION: hsa-miR-502-5p

<400> SEQUENCE: 65
auccuugcua ucugggugcu a                     21

<210> SEQ ID NO 66
<211> LENGTH: 23
<212> TYPE: RNA
<213> ORGANISM: Homo sapiens
<220> FEATURE:
<223> OTHER INFORMATION: hsa-miR-542-5p

<400> SEQUENCE: 66
ucggggauca ucaugucacg aga                   23

<210> SEQ ID NO 67
<211> LENGTH: 23
<212> TYPE: RNA
<213> ORGANISM: Homo sapiens
<220> FEATURE:
<223> OTHER INFORMATION: hsa-miR-550a-5p

<400> SEQUENCE: 67
agugccugag ggaguaagag ccc                   23

<210> SEQ ID NO 68
<211> LENGTH: 22
<212> TYPE: RNA
<213> ORGANISM: Homo sapiens
<220> FEATURE:
<223> OTHER INFORMATION: hsa-miR-576-3p

<400> SEQUENCE: 68
aagaugugga aaaauuggaa uc                    22

<210> SEQ ID NO 69
<211> LENGTH: 22
<212> TYPE: RNA
<213> ORGANISM: Homo sapiens
<220> FEATURE:
<223> OTHER INFORMATION: hsa-miR-582-3p

<400> SEQUENCE: 69
uaacugguug aacaacugaa cc                    22

<210> SEQ ID NO 70
<211> LENGTH: 22
<212> TYPE: RNA
<213> ORGANISM: Homo sapiens -continued

```
<220> FEATURE:
<223> OTHER INFORMATION: hsa-miR-642a-5p

<400> SEQUENCE: 70
gucccucucc aaaugugucu ug                                              22

<210> SEQ ID NO 71
<211> LENGTH: 22
<212> TYPE: RNA
<213> ORGANISM: Homo sapiens
<220> FEATURE:
<223> OTHER INFORMATION: hsa-miR-942

<400> SEQUENCE: 71
ucuucucugu uuuggccaug ug                                              22

<210> SEQ ID NO 72
<211> LENGTH: 97
<212> TYPE: RNA
<213> ORGANISM: Homo sapiens
<220> FEATURE:
<223> OTHER INFORMATION: hsa-mir-127

<400> SEQUENCE: 72
ugugaucacu gucuccagcc ugcugaagcu cagagggcuc ugauucagaa agaucaucgg     60
auccgucuga gcuuggcugg ucggaagucu caucauc                             97

<210> SEQ ID NO 73
<211> LENGTH: 65
<212> TYPE: RNA
<213> ORGANISM: Homo sapiens
<220> FEATURE:
<223> OTHER INFORMATION: hsa-mir-155

<400> SEQUENCE: 73
cuguuaaugc uaaucgugau agggguuuuu gccuccaacu gacuccuaca uauuagcauu     60
aacag                                                                65

<210> SEQ ID NO 74
<211> LENGTH: 110
<212> TYPE: RNA
<213> ORGANISM: Homo sapiens
<220> FEATURE:
<223> OTHER INFORMATION: hsa-mir-181a-1

<400> SEQUENCE: 74
ugaguuuuga gguugcuuca gugaacauuc aacgcugucg gugaguuugg aauuaaaauc     60
aaaaccaucg accguugauu guacccuaug gcuaaccauc aucuacucca               110

<210> SEQ ID NO 75
<211> LENGTH: 137
<212> TYPE: RNA
<213> ORGANISM: Homo sapiens
<220> FEATURE:
<223> OTHER INFORMATION: hsa-mir-181d

<400> SEQUENCE: 75
gucccucccc cuaggccaca gccgagguca caaucaacau ucauuguugu cgguggguug     60
ugaggacuga ggccagaccc accggggau gaaugucacu guggcugggc cagacacggc    120
uuaaggggaa uggggac                                                  137

<210> SEQ ID NO 76
```

```
<211> LENGTH: 86
<212> TYPE: RNA
<213> ORGANISM: Homo sapiens
<220> FEATURE:
<223> OTHER INFORMATION: hsa-mir-188

<400> SEQUENCE: 76
ugcucccucu cucacauccc uugcauggug gagggugagc uuucugaaaa ccccucccac      60
augcagggnu ugcaggaugg cgagcc                                          86

<210> SEQ ID NO 77
<211> LENGTH: 80
<212> TYPE: RNA
<213> ORGANISM: Homo sapiens
<220> FEATURE:
<223> OTHER INFORMATION: hsa-mir-1908

<400> SEQUENCE: 77
cgggaaugcc gcggcgggga cggcgauugg uccguaugug ggugccacc ggccgccggc      60 uccgccccgg cccccgcccc                                                 80

<210> SEQ ID NO 78
<211> LENGTH: 85
<212> TYPE: RNA
<213> ORGANISM: Homo sapiens
<220> FEATURE:
<223> OTHER INFORMATION: hsa-mir-190a

<400> SEQUENCE: 78
ugcaggccuc ugugugauau guuugauaua uuagguuguu auuuaaucca acuauauauc      60
aaacauauuc cuacaguguc uugcc                                           85

<210> SEQ ID NO 79
<211> LENGTH: 110
<212> TYPE: RNA
<213> ORGANISM: Homo sapiens
<220> FEATURE:
<223> OTHER INFORMATION: hsa-mir-203a

<400> SEQUENCE: 79 guguuggga cucgcgcgcu ggguccagug guucuuaaca guucaacagu ucuguagcgc       60 aaugugaaa uguuuaggac cacuagaccc ggcgggcgcg gcgacagcga                 110

<210> SEQ ID NO 80
<211> LENGTH: 94
<212> TYPE: RNA
<213> ORGANISM: Homo sapiens
<220> FEATURE:
<223> OTHER INFORMATION: hsa-mir-330

<400> SEQUENCE: 80
cuuuggcgau cacugccucu cugggccugu gucuuaggcu cugcaagauc aaccgagcaa     60
agcacacggc cugcagagag gcagcgcucu gccc                                 94

<210> SEQ ID NO 81
<211> LENGTH: 99
<212> TYPE: RNA
<213> ORGANISM: Homo sapiens
<220> FEATURE:
<223> OTHER INFORMATION: hsa-mir-342

<400> SEQUENCE: 81
gaaacugggc ucaaggugag gggugcuauc ugugauugag ggacaugguu aauggaauug     60
```

```
ucucacacag aaaucgcacc cgucaccuug gccuacuua                            99
```

<210> SEQ ID NO 82
<211> LENGTH: 70
<212> TYPE: RNA
<213> ORGANISM: Homo sapiens
<220> FEATURE:
<223> OTHER INFORMATION: hsa-mir-369

<400> SEQUENCE: 82

```
uugaagggag aucgaccgug uuauauucgc uuuauugacu ucgaauaaua caugguugau    60
cuuuucucag                                                          70
```

<210> SEQ ID NO 83
<211> LENGTH: 69
<212> TYPE: RNA
<213> ORGANISM: Homo sapiens
<220> FEATURE:
<223> OTHER INFORMATION: hsa-mir-377

<400> SEQUENCE: 83

```
uugagcagag guugcccuug gugaauucgc uuuauuuaug uugaaucaca caaaggcaac    60
uuuuguuug                                                           69
```

<210> SEQ ID NO 84
<211> LENGTH: 66
<212> TYPE: RNA
<213> ORGANISM: Homo sapiens
<220> FEATURE:
<223> OTHER INFORMATION: hsa-mir-378a

<400> SEQUENCE: 84

```
agggcuccug acuccagguc cuguguguua ccuagaaaua gcacuggacu uggagucaga    60
aggccu                                                              66
```

<210> SEQ ID NO 85
<211> LENGTH: 76
<212> TYPE: RNA
<213> ORGANISM: Homo sapiens
<220> FEATURE:
<223> OTHER INFORMATION: hsa-mir-382

<400> SEQUENCE: 85

```
uacuugaaga gaaguuguuc gugguggauu cgcuuuacuu augacgaauc auucacggac    60
aacacuuuuu ucagua                                                   76
```

<210> SEQ ID NO 86
<211> LENGTH: 82
<212> TYPE: RNA
<213> ORGANISM: Homo sapiens
<220> FEATURE:
<223> OTHER INFORMATION: hsa-mir-495

<400> SEQUENCE: 86

```
ugguaccuga aaagaaguug cccauguuau uuucgcuuua uaugugacga aacaaacaug    60
gugcacuucu uuuucgguau ca                                            82
```

<210> SEQ ID NO 87
<211> LENGTH: 84
<212> TYPE: RNA
<213> ORGANISM: Homo sapiens
<220> FEATURE:

<223> OTHER INFORMATION: hsa-mir-500a

<400> SEQUENCE: 87 gcuccccuc ucuaauccuu gcuaccuggg ugagagugcu gucugaaugc aaugcaccug       60
ggcaaggauu cugagagcga gagc                                            84

<210> SEQ ID NO 88
<211> LENGTH: 86
<212> TYPE: RNA
<213> ORGANISM: Homo sapiens
<220> FEATURE:
<223> OTHER INFORMATION: hsa-mir-502

<400> SEQUENCE: 88 ugcuccccu cucuaauccu ugcuaucugg gugcuagugc uggcucaaug caaugcaccu       60
gggcaaggau ucagagaggg ggagcu                                          86

<210> SEQ ID NO 89
<211> LENGTH: 97
<212> TYPE: RNA
<213> ORGANISM: Homo sapiens
<220> FEATURE:
<223> OTHER INFORMATION: hsa-mir-542

<400> SEQUENCE: 89
cagaucucag acaucucggg gaucaucaug ucacgagaua ccagugugca cuugugacag      60
auugauaacu gaaaggucug ggagccacuc aucuuca                              97

<210> SEQ ID NO 90
<211> LENGTH: 97
<212> TYPE: RNA
<213> ORGANISM: Homo sapiens
<220> FEATURE:
<223> OTHER INFORMATION: hsa-mir-550a-1

<400> SEQUENCE: 90
ugaugcuuug cuggcuggug cagugccuga gggaguaaga gcccuguugu uguaagauag      60
ugucuuacuc ccucaggcac aucccaaca agucucu                               97

<210> SEQ ID NO 91
<211> LENGTH: 98
<212> TYPE: RNA
<213> ORGANISM: Homo sapiens
<220> FEATURE:
<223> OTHER INFORMATION: hsa-mir-576

<400> SEQUENCE: 91
uacaauccaa cgaggauucu aauuucucca cgucuuuggu aauaagguuu ggcaaagaug      60
uggaaaaauu ggaauccuca uucgauuggu uauaacca                             98

<210> SEQ ID NO 92
<211> LENGTH: 98
<212> TYPE: RNA
<213> ORGANISM: Homo sapiens
<220> FEATURE:
<223> OTHER INFORMATION: hsa-mir-582

<400> SEQUENCE: 92
aucugugcuc uuugauuaca guugucaac caguuacuaa ucuaacuaau uguaacuggu       60
ugaacaacug aacccaaagg gugcaaagua gaaacauu                             98

```
<210> SEQ ID NO 93
<211> LENGTH: 97
<212> TYPE: RNA
<213> ORGANISM: Homo sapiens
<220> FEATURE:
<223> OTHER INFORMATION: hsa-mir-642a

<400> SEQUENCE: 93
aucugaguug ggaggguccc ucuccaaaug ugucuugggg uggggauca agacacauuu    60 ggagagggaa ccucccaacu cggccucugc caucauu                            97

<210> SEQ ID NO 94
<211> LENGTH: 86
<212> TYPE: RNA
<213> ORGANISM: Homo sapiens
<220> FEATURE:
<223> OTHER INFORMATION: hsa-mir-942

<400> SEQUENCE: 94
auuaggagag uaucuucucu guuuuggcca uguguguacu cacagccccu cacacauggc    60
cgaaacagag aaguuacuuu ccuaau                                        86

<210> SEQ ID NO 95
<211> LENGTH: 23
<212> TYPE: RNA
<213> ORGANISM: Homo sapiens
<220> FEATURE:
<223> OTHER INFORMATION: hsa-miR-335-5p

<400> SEQUENCE: 95
ucaagagcaa uaacgaaaaa ugu                                           23

<210> SEQ ID NO 96
<211> LENGTH: 23
<212> TYPE: RNA
<213> ORGANISM: Homo sapiens
<220> FEATURE:
<223> OTHER INFORMATION: hsa-miR-29b-3p

<400> SEQUENCE: 96
uagcaccauu ugaaaucagu guu                                           23

<210> SEQ ID NO 97
<211> LENGTH: 23
<212> TYPE: RNA
<213> ORGANISM: Homo sapiens
<220> FEATURE:
<223> OTHER INFORMATION: hsa-miR-199b-5p

<400> SEQUENCE: 97
cccaguguuu agacuaucug uuc                                           23

<210> SEQ ID NO 98
<211> LENGTH: 22
<212> TYPE: RNA
<213> ORGANISM: Homo sapiens
<220> FEATURE:
<223> OTHER INFORMATION: hsa-miR-214-3p

<400> SEQUENCE: 98
acagcaggca cagacaggca gu                                            22

<210> SEQ ID NO 99
<211> LENGTH: 22
<212> TYPE: RNA
```

<213> ORGANISM: Homo sapiens
<220> FEATURE:
<223> OTHER INFORMATION: hsa-miR-144-5p

<400> SEQUENCE: 99
ggauaucauc auauacugua ag                                      22

<210> SEQ ID NO 100
<211> LENGTH: 21
<212> TYPE: RNA
<213> ORGANISM: Homo sapiens
<220> FEATURE:
<223> OTHER INFORMATION: hsa-miR-31-5p

<400> SEQUENCE: 100
aggcaagaug cuggcauagc u                                       21

<210> SEQ ID NO 101
<211> LENGTH: 94
<212> TYPE: RNA
<213> ORGANISM: Homo sapiens
<220> FEATURE:
<223> OTHER INFORMATION: hsa-mir-335

<400> SEQUENCE: 101 uguuugagc gggggucaag agcaauaacg aaaaauguuu gucauaaacc guuuucauu    60 auugcuccug accuccucuc auuugcuaua uuca                             94

<210> SEQ ID NO 102
<211> LENGTH: 81
<212> TYPE: RNA
<213> ORGANISM: Homo sapiens
<220> FEATURE:
<223> OTHER INFORMATION: hsa-mir-29b-1

<400> SEQUENCE: 102
cuucaggaag cugguuucau auggugguuu agauuuaaau agugauuguc uagcaccauu  60
ugaaaucagu guucuugggg g                                           81

<210> SEQ ID NO 103
<211> LENGTH: 110
<212> TYPE: RNA
<213> ORGANISM: Homo sapiens
<220> FEATURE:
<223> OTHER INFORMATION: hsa-mir-199b

<400> SEQUENCE: 103
ccagaggaca ccuccacucc gucucccag uguuuagacu aucguucag gacucccaaa   60 uuguacagua gucugcacau ugguuaggcu gggcugggu agacccucgg           110

<210> SEQ ID NO 104
<211> LENGTH: 110
<212> TYPE: RNA
<213> ORGANISM: Homo sapiens
<220> FEATURE:
<223> OTHER INFORMATION: hsa-mir-214

<400> SEQUENCE: 104
ggccuggcug gacagaguug ucaugugucu gccugucuac acuugcugug cagaacaucc  60
gcucaccugu acagcaggca cagacaggca gucacaugac aacccagccu            110

<210> SEQ ID NO 105
<211> LENGTH: 86

```
<212> TYPE: RNA
<213> ORGANISM: Homo sapiens
<220> FEATURE:
<223> OTHER INFORMATION: hsa-mir-144

<400> SEQUENCE: 105
uggggcccug gcugggauau caucauauac uguaaguuug cgaugagaca cuacaguaua        60
gaugauguac uaguccgggc acccccc                                           86

<210> SEQ ID NO 106
<211> LENGTH: 71
<212> TYPE: RNA
<213> ORGANISM: Homo sapiens
<220> FEATURE:
<223> OTHER INFORMATION: hsa-miR-31

<400> SEQUENCE: 106
ggagaggagg caagaugcug gcauagcugu ugaacuggga accugcuaug ccaacauauu        60
gccaucuuuc c                                                            71
```